US012735385B2

(12) United States Patent
Toscano et al.

(10) Patent No.: US 12,735,385 B2
(45) Date of Patent: Sep. 15, 2026

(54) ALKYLSULFENYL THIOCARBONATES: PRECURSORS TO HYDROPERSULFIDES POTENTLY ATTENUATE OXIDATIVE STRESS

(71) Applicant: The Johns Hopkins University, Baltimore, MD (US)

(72) Inventors: John Pasquale Toscano, Glen Arm, MD (US); Vinayak S. Khodade, Baltimore, MD (US); Sahil Aggarwal, Baltimore, MD (US); Nazareno Paolocci, Baltimore, MD (US); Blaze Pharoah, Baltimore, MD (US); Gizem Keceli, Baltimore, MD (US); Kelsey Zhang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 343 days.

(21) Appl. No.: 18/557,612

(22) PCT Filed: Apr. 29, 2022

(86) PCT No.: PCT/US2022/027101

§ 371 (c)(1), (2) Date: Oct. 27, 2023

(87) PCT Pub. No.: WO2022/232622

PCT Pub. Date: Nov. 3, 2022

(65) Prior Publication Data

US 2025/0282720 A1 Sep. 11, 2025

Related U.S. Application Data

(60) Provisional application No. 63/181,758, filed on Apr. 29, 2021.

(51) Int. Cl.

| | |
|---|---|
| ***C07C 329/04*** | (2006.01) |
| ***A61K 31/265*** | (2006.01) |
| ***A61P 9/04*** | (2006.01) |
| ***A61P 25/28*** | (2006.01) |
| ***A61P 31/14*** | (2006.01) |

(52) U.S. Cl.

CPC .......... *C07C 329/04* (2013.01); *A61K 31/265* (2013.01); *A61P 9/04* (2018.01); *A61P 25/28* (2018.01); *A61P 31/14* (2018.01)

(58) Field of Classification Search

CPC ........ C07C 329/04; A61P 25/28; A61P 31/14; A61P 9/04; A61K 31/265

See application file for complete search history.

(56) References Cited

U.S. PATENT DOCUMENTS 4,798,824 A 1/1989 Belzer et al.

FOREIGN PATENT DOCUMENTS

WO WO 2022/186926 9/2022

OTHER PUBLICATIONS

International Search Report and Written Opinion for PCT/US22/27101. Mailed Jul. 27, 2022. 11 pages.

Abeti et al., Novel Nrf2-Inducer Prevents Mitochondrial Defects and Oxidative Stress in Friedreich's Ataxia Models. Front Cell Neurosci. Jul. 17, 2018:12:188. 10 pages.

Agrimi et al., Obese mice exposed to psychosocial stress display cardiac and hippocampal dysfunction associated with local brain-derived neurotrophic factor depletion. EBioMedicine. Sep. 2019:47:384-401.

Ahsan et al, Redox regulation of cell survival by the thioredoxin superfamily: an implication of redox gene therapy in the heart. Antioxid Redox Signal. Nov. 2009;11(11):2741-58.

Akaike et al., Cysteinyl-tRNA synthetase governs cysteine polysulfidation and mitochondrial bioenergetics. Nat Commun. Oct. 27, 2017;8(1):1177. 15 pages.

Alisik et al., A colorimetric method to measure oxidized, reduced and total glutathione levels in erythrocytes. J. Lab. Med. 2019, 43 (5), 269-277.

Alvarez et al., Chemical Biology of Hydropersulfides and Related Species: Possible Roles in Cellular Protection and Redox Signaling. Antioxid Redox Signal. Oct. 1, 2017;27(10):622-633.

Amgalan et al., A small-molecule allosteric inhibitor of BAX protects against doxorubicin-induced cardiomyopathy. Nat Cancer. Mar. 2020;1(3):315-328.

Apple et al., Inhibitory effect of DL-2-mercapto-3-hydroxypropanal on growth of transplantable cancers in mice. Cancer Chemother Rep. Jun. 1969;53(3):195-8.

Arkat et al., Mitochondrial Peroxiredoxin-3 protects against hyperglycemia induced myocardial damage in Diabetic cardiomyopathy. Free Radic Biol Med. Aug. 2016:97:489-500.

Artaud et al., A persulfide analogue of the nitrosothiol SNAP: formation, characterization and reactivity. Chembiochem. Nov. 3, 2014;15(16):2361-4.

Baldwin et al., Photoaffinity labelling of isopenicillin N synthetase by laser-flash photolysis. Biochem J. Jul. 1, 1989;261(1):197-204.

Barr et al., Discoveries of hydrogen sulfide as a novel cardiovascular therapeutic. Circ J. 2014;78(9):2111-8.

(Continued)

*Primary Examiner* — Rebecca L Anderson

(74) *Attorney, Agent, or Firm* — Casimir Jones, SC; Jeffrey W. Childers

(57) ABSTRACT

Alkylsulfenyl thiocarbonates capable of releasing hydropersulfides (RSSH) and carbonyl sulfide (COS) under physiological conditions and their use for treating or preventing disorders, diseases, or conditions associated with oxidative stress, impaired Fe—S cluster biosynthesis, including Friedreich's Ataxia, and anthracycline-induced cardiotoxicity, including cardiomyopathy and heart failure, are described.

28 Claims, 18 Drawing Sheets

(56) References Cited

OTHER PUBLICATIONS

Bechoam et al., Acidity and nucleophilic reactivity of glutathione persulfide. J Biol Chem. Nov. 13, 2020;295(46):15466-15481.
Benchoam et al., Hydrogen Sulfide and Persulfides Oxidation by Biologically Relevant Oxidizing Species. Antioxidants (Basel). Feb. 22, 2019;8(2):48. 23 pages.
Berge et al., Pharmaceutical salts. J Pharm Sci. Jan. 1977;66(1):1-19.
Bianco et al., The reaction of hydrogen sulfide with disulfides: formation of a stable trisulfide and implications for biological systems. Br J Pharmacol. Feb. 2019;176(4):671-683.
Bora et al., A Vinyl-Boronate Ester-Based Persulfide Donor Controllable by Hydrogen Peroxide, a Reactive Oxygen Species (ROS). Org Lett. Dec. 21, 2018;20(24):7916-7920.
Brois et al., New synthetic concepts in organosulfur chemistry. I. New pathway to unsymmetrical disulfides. The thiol-induced fragmentation of sulfenyl thiocarbonates. J. Am. Chem. Soc. 1970, 92(26), 7629-7631.
Cadeddu Dessalvi et al., Antioxidant Approach as a Cardioprotective Strategy in Chemotherapy-Induced Cardiotoxicity. Antioxid Redox Signal. Mar. 1, 2021;34(7):572-588.
Cai et al., Human Mitochondrial Ferredoxin 1 (FDX1) and Ferredoxin 2 (FDX2) Both Bind Cysteine Desulfurase and Donate Electrons for Iron-Sulfur Cluster Biosynthesis. Biochemistry. Jan. 24, 2017;56(3):487-499.
Campuzano et al., Friedreich's ataxia: autosomal recessive disease caused by an intronic GAA triplet repeat expansion. Science. Mar. 8, 1996;271(5254):1423-7.
Chaudhuri et al., One- and Two-Photon-Activated Cysteine Persulfide Donors for Biological Targeting. J Org Chem. Sep. 20, 2019;84(18):11441-11449.
Chauvin et al., Hydropersulfides: H-Atom Transfer Agents Par Excellence. J Am Chem Soc. May 10, 2017;139(18):6484-6493.
Chelko et al., Exercise triggers CAPN1-mediated AIF truncation, inducing myocyte cell death in arrhythmogenic cardiomyopathy. Sci Transl Med. Feb. 17, 2021;13(581):eabf0891. 46 pages.
Chen et al., Activation of Nrf2/ARE pathway protects endothelial cells from oxidant injury and inhibits inflammatory gene expression. Am J Physiol Heart Circ Physiol. May 2006;290(5):H1862-70.
Chen et al., New fluorescent probes for sulfane sulfurs and the application in bioimaging. Chem Sci. May 9, 2013;4(7):2892-2896.
Chengelis et al., Studies of carbonyl sulfide toxicity: Metabolism by carbonic anhydrase. Toxicol Appl Pharmacol. Aug. 1980;55(1):198-202.
Citi et al., Anti-inflammatory and antiviral roles of hydrogen sulfide: Rationale for considering H2 S donors in COVID-19 therapy. Br J Pharmacol. Nov. 2020;177(21):4931-4941.
Classen et al., Structure of the topoisomerase II ATPase region and its mechanism of inhibition by the chemotherapeutic agent ICRF-187. Proc Natl Acad Sci U S A. Sep. 16, 2003;100(19):10629-34.
Cline et al., Detection of nitroxyl (HNO) by membrane inlet mass spectrometry. Free Radic Biol Med. May 15, 2011;50(10):1274-9.
Cuevasanta et al., Reaction of Hydrogen Sulfide with Disulfide and Sulfenic Acid to Form the Strongly Nucleophilic Persulfide. J Biol Chem. Nov. 6, 2015;290(45):26866-26880.
Dallons et al., New Insights About Doxorubicin-Induced Toxicity to Cardiomyoblast-Derived H9C2 Cells and Dexrazoxane Cytoprotective Effect: Contribution of In Vitro 1H-NMR Metabonomics. Front Pharmacol. Feb. 20, 2020:11:79. 14 pages.
Dhalla et al., Role of oxidative stress in cardiovascular diseases. J Hypertens. Jun. 2000;18(6):655-73.
Dhanasekaran et al., Emerging insights into mitochondria-specific targeting and drug delivering strategies: Recent milestones and therapeutic implications. Saudi J Biol Sci. Dec. 2020;27(12):3581-3592.
Di Prospero et al., Neurological effects of high-dose idebenone in patients with Friedreich's ataxia: a randomised, placebo-controlled trial. Lancet Neurol. Oct. 2007;6(10):878-86.
Dikalov et al., Tobacco smoking induces cardiovascular mitochondrial oxidative stress, promotes endothelial dysfunction, and enhances hypertension. Am J Physiol Heart Circ Physiol. Mar. 1, 2019;316(3):H639-H646.
Dillon et al., A Review of Chemical Tools for Studying Small Molecule Persulfides: Detection and Delivery. ACS Chem Biol. Jul. 16, 2021;16(7):1128-1141.
Dillon et al., Polymeric persulfide prodrugs: Mitigating oxidative stress through controlled delivery of reactive sulfur species. ACS Macro Lett. Apr. 21, 2020;9(4):606-612.
Dinkova-Kostova et al., NAD(P)H:quinone acceptor oxidoreductase 1 (NQO1), a multifunctional antioxidant enzyme and exceptionally versatile cytoprotector. Arch Biochem Biophys. Sep. 1, 2010;501(1):116-23.
Dixon et al., Ferroptosis: an iron-dependent form of nonapoptotic cell death. Cell. May 25, 2012;149(5):1060-72.
Doka et al., A novel persulfide detection method reveals protein persulfide- and polysulfide-reducing functions of thioredoxin and glutathione systems. Sci Adv. Jan. 22, 2016;2(1):e1500968. 14 pages.
Doka et al., Control of protein function through oxidation and reduction of persulfidated states. Sci Adv. Jan. 1, 2020;6(1):eaax8358. 20 pages.
D'Oria et al., The Role of Oxidative Stress in Cardiac Disease: From Physiological Response to Injury Factor. Oxid Med Cell Longev. May 14, 2020:2020:5732956. 29 pages.
Du et al., Protective Mechanism of Hydrogen Sulfide against Chemotherapy-Induced Cardiotoxicity. Front Pharmacol. Jan. 26, 2018:9:32. 8 pages.
Durr et al., Clinical and genetic abnormalities in patients with Friedreich's ataxia. N Engl J Med. Oct. 17, 1996;335(16):1169-75.
Erdelyi et al., Reprogrammed transsulfuration promotes basal-like breast tumor progression via realigning cellular cysteine persulfidation. Proc Natl Acad Sci U S A. Nov. 9, 2021;118(45):e2100050118. 12 pages.
Everett et al., Free-radical repair by a novel perthiol: reversible hydrogen transfer and perthiyl radical formation. Free Radic Res. Jun. 1994;20(6):387-400.
Feng et al., Constitutive BDNF/TrkB signaling is required for normal cardiac contraction and relaxation. Proc Natl Acad Sci U S A. Feb. 10, 2015;112(6):1880-5.
Feng et al., Transferrin Receptor Is a Specific Ferroptosis Marker. Cell Rep. Mar. 10, 2020;30(10):3411-3423.e7.
Filipovic et al., Chemical Biology of H2S Signaling through Persulfidation. Chem Rev. Feb. 14, 2018;118(3):1253-1337.
Freibert et al., N-terminal tyrosine of ISCU2 triggers [2Fe-2S] cluster synthesis by ISCU2 dimerization. Nat Commun. Nov. 25, 2021;12(1):6902. 15 pages.
Fukuto et al., A comparison of the chemical biology of hydropersulfides (RSSH) with other protective biological antioxidants and nucleophiles. Nitric Oxide. Feb. 1, 2021:107:46-57.
Fukuto et al., Biological hydropersulfides and related polysulfides—a new concept and perspective in redox biology. FEBS Lett. Jun. 2018;592(12):2140-2152.
Fukuto et al., Predicting the Possible Physiological/Biological Utility of the Hydropersulfide Functional Group Based on Its Chemistry: Similarities Between Hydropersulfides and Selenols. Antioxid Redox Signal. Dec. 20, 2020;33(18):1295-1307.
Gadalla et al., Hydrogen sulfide as a gasotransmitter. J Neurochem. Apr. 2010;113(1):14-26.
Gammella et al., The role of iron in anthracycline cardiotoxicity. Front Pharmacol. Feb. 26, 2014:5:25. 6 pages.
Gao et al., 5'-AMP-activated protein kinase attenuates adriamycin-induced oxidative podocyte injury through thioredoxin-mediated suppression of the apoptosis signal-regulating kinase 1-P38 signaling pathway. Mol Pharmacol. Mar. 2014;85(3):460-71.
Gervason et al., Physiologically relevant reconstitution of iron-sulfur cluster biosynthesis uncovers persulfide-processing functions of ferredoxin-2 and frataxin. Nat Commun. Aug. 8, 2019;10(1):3566. 12 pages.
Gottesfeld. Small molecules affecting transcription in Friedreich ataxia. Pharmacol Ther. Nov. 2007;116(2):236-48.

(56) References Cited

OTHER PUBLICATIONS

Greiner et al., Polysulfides link H2S to protein thiol oxidation. Antioxid Redox Signal. Nov. 20, 2013;19(15):1749-65.
Gureev et al., Regulation of Mitochondrial Biogenesis as a Way for Active Longevity: Interaction Between the Nrf2 and PGC-1α Signaling Pathways. Front Genet. May 14, 2019:10:435. 12 pages.
Harpp et al., Cyclic trisulfides by alkoxide decomposition of bis-(sulfenyl) thiocarbonates. J. Org. Chem., 1979, 44, 4144-4148.
Harpp et al., Organic sulfur chemistry. XXI. Trisulfide formation by alkoxide decomposition of sulfenylthiocarbonates. Tetrahedron Lett., 1976, 17, 3001-3004.
Hart et al., Antioxidant treatment of patients with Friedreich ataxia: four-year follow-up. Arch Neurol. Apr. 2005;62(4):621-6.
Hayden et al., Sodium thiosulfate: new hope for the treatment of calciphylaxis. Semin Dial. May-Jun. 2010;23(3):258-62.
Hoch et al., A mass spectrometer inlet system for sampling gases dissolved in liquid phases. Arch Biochem Biophys. Apr. 1963:101:160-70.
Hofgaard et al., Protection by 6-aminonicotinamide against oxidative stress in cardiac cells. Pharmacol Res. Oct. 2006;54(4):303-10.
Hortobagyi. Anthracyclines in the treatment of cancer. An overview. Drugs. 1997:54 Suppl 4:1-7.
Hull et al., Heme oxygenase-1 regulates mitochondrial quality control in the heart. JCI Insight. 2016;1(2):e85817. 18 pages.
Hybertson et al., Oxidative stress in health and disease: the therapeutic potential of Nrf2 activation. Mol Aspects Med. Aug. 2011;32(4-6):234-46.
Ibrahim et al., Established and Emerging Roles of Biomarkers in Heart Failure. Circ Res. Aug. 17, 2018;123(5):614-629.
Iciek et al., Sulfane sulfur—new findings on an old topic. Acta Biochim Pol. Dec. 28, 2019;66(4):533-544.
Ida et al., Reactive cysteine persulfides and S-polythiolation regulate oxidative stress and redox signaling. Proc Natl Acad Sci U S A. May 27, 2014;111(21):7606-11.
Ishiyama et al., A highly water-soluble disulfonated tetrazolium salt as a chromogenic indicator for NADH as well as cell viability. Talanta. Jul. 1997;44(7):1299-305.
Jiang et al., Peroxiredoxin-1 Overexpression Attenuates Doxorubicin-Induced Cardiotoxicity by Inhibiting Oxidative Stress and Cardiomyocyte Apoptosis. Oxid Med Cell Longev. Jul. 29, 2020:2020:2405135. 11 pages.
Johnson et al., Structure, function, and formation of biological iron-sulfur clusters. Annu Rev Biochem. 2005:74:247-81.
Jones et al., Fluorescence microplate-based assay for tumor necrosis factor activity using SYTOX Green stain. Anal Biochem. Jun. 1, 2001;293(1):8-15.
Kaludercic et al., Monoamine oxidase B prompts mitochondrial and cardiac dysfunction in pressure overloaded hearts. Antioxid Redox Signal. Jan. 10, 2014;20(2):267-80.
Kang et al., O→S Relay Deprotection: A General Approach to Controllable Donors of Reactive Sulfur Species. Angew Chem Int Ed Engl. May 14, 2018;57(20):5893-5897.
Kasamatsu et al., Redox Signaling Regulated by Cysteine Persulfide and Protein Polysulfidation. Molecules. Dec. 15, 2016;21(12):1721. 10 pages.
Kaspar et al., Nrf2:INrf2 (Keap1) signaling in oxidative stress. Free Radic Biol Med. Nov. 1, 2009;47(9):1304-9.
Khodade et al., Alkylamine-Substituted Perthiocarbamates: Dual Precursors to Hydropersulfide and Carbonyl Sulfide with Cardioprotective Actions. Chem Sci. May 14, 2021;12(23):8252-8259.
Khodade et al., Alkylamine-Substituted Perthiocarbamates: Dual Precursors to Hydropersulfide and Carbonyl Sulfide with Cardioprotective Actions. J Am Chem Soc. Mar. 4, 2020;142(9):4309-4316.
Khodade et al., Development of Hydropersulfide Donors to Study Their Chemical Biology. Antioxid Redox Signal. Feb. 2022;36(4-6):309-326.
Khodade et al., Development of S-Substituted Thioisothioureas as Efficient Hydropersulfide Precursors. J Am Chem Soc. Dec. 19, 2018;140(50):17333-17337.
Kimura. Hydrogen sulfide and polysulfides as biological mediators. Molecules. Oct. 9, 2014;19(10):16146-57.
Koike et al., Cysteine persulfides and polysulfides produced by exchange reactions with H2S protect SH-SY5Y cells from methylglyoxal-induced toxicity through Nrf2 activation. Redox Biol. Aug. 2017:12:530-539.
Kolluru et al., Reactive Sulfur Species: A New Redox Player in Cardiovascular Pathophysiology. Arterioscler Thromb Vasc Biol. Apr. 2020;40(4):874-884.
Kull et al., Mixturs of quaternary ammonium compounds and long-chain fatty acids as antifungal agents. Appl Microbiol. Nov. 1961;9(6):538-41.
Kulkarni et al., A Novel Triphenylphosphonium Carrier to Target Mitochondria without Uncoupling Oxidative Phosphorylation. J Med Chem. Jan. 14, 2021;64(1):662-676.
Kunikata et al., Metabolomic profiling of reactive persulfides and polysulfides in the aqueous and vitreous humors. Sci Rep. Feb. 7, 2017:7:41984.
Kurdi et al., Depletion of cellular glutathione modulates LIF-induced JAK1-STAT3 signaling in cardiac myocytes. Int J Biochem Cell Biol. Dec. 2012;44(12):2106-15.
Lagoa et al., The decrease of NAD(P)H:quinone oxidoreductase 1 activity and increase of ROS production by NADPH oxidases are early biomarkers in doxorubicin cardiotoxicity. Biomarkers. Mar. 2014;19(2):142-53.
Langer. Dexrazoxane for the treatment of chemotherapy-related side effects. Cancer Manag Res. Sep. 15, 2014:6:357-63.
Lazo et al., The association of liver enzymes with biomarkers of subclinical myocardial damage and structural heart disease. J Hepatol. Apr. 2015;62(4):841-7.
Leininger et al., The mechanism of the rhodanese-catalyzed thiosulfate-cyanide reaction. Thermodynamic and activation parameters. J Biol Chem. Apr. 25, 1968;243(8):1892-9.
Li et al., The interaction of estrogen and CSE/H2S pathway in the development of atherosclerosis. Am J Physiol Heart Circ Physiol. Mar. 1, 2017;312(3):H406-H414.
Li et al., Therapeutic potential of endogenous hydrogen sulfide inhibition in breast cancer (Review). Oncol Rep. May 2021;45(5):68. 9 pages.
Libiad et al., Organization of the human mitochondrial hydrogen sulfide oxidation pathway. J Biol Chem. Nov. 7, 2014;289(45):30901-10.
Libiad et al., Polymorphic Variants of Human Rhodanese Exhibit Differences in Thermal Stability and Sulfur Transfer Kinetics. J Biol Chem. Sep. 25, 2015;290(39):23579-88.
Lill et al., Maturation of iron-sulfur proteins in eukaryotes: mechanisms, connected processes, and diseases. Annu Rev Biochem. 2008:77:669-700.
Liu et al., Formation of 4-hydroxynonenal from cardiolipin oxidation: Intramolecular peroxyl radical addition and decomposition. Free Radic Biol Med. Jan. 1, 2011;50(1):166-78.
Liu et al., Isotope dilution mass spectrometry for the quantification of sulfane sulfurs. Free Radic Biol Med. Nov. 2014:76:200-7.
Longen et al., Quantitative Persulfide Site Identification (qPerS-SID) Reveals Protein Targets of H2S Releasing Donors in Mammalian Cells. Sci Rep. Jul. 14, 2016:6:29808. 12 pages.
Lupoli et al., The role of oxidative stress in Friedreich's ataxia. FEBS Lett. Mar. 2018;592(5):718-727.
Manford et al., A Cellular Mechanism to Detect and Alleviate Reductive Stress. Cell. Oct. 1, 2020;183(1):46-61.e21.
Manford et al., Structural basis and regulation of the reductive stress response. Cell. Oct. 14, 2021;184(21):5375-5390.e16.
Martinez et al., Detection of Ferroptosis by BODIPYTM 581/591 C11. in Immune Mediators in Cancer: Methods and Protocols (Vancurova, I., and Zhu, Y. eds), Springer US, New York, NY, 2020. 125-130.
Marutani et al., Cytoprotective effects of hydrogen sulfide-releasing N-methyl-D-aspartate receptor antagonists are mediated by intracellular sulfane sulfur. Medchemcomm. Oct. 1, 2014;5(10):1577-1583.
Meiners et al., Clinical and preclinical evidence of sex-related differences in anthracycline-induced cardiotoxicity. Biol Sex Differ. Aug. 29, 2018;9(1):38.

(56) References Cited

OTHER PUBLICATIONS

Miller et al., Cancer treatment and survivorship statistics, 2019. CA Cancer J Clin. Sep. 2019;69(5):363-385.
Mizuta et al., Sodium thiosulfate prevents doxorubicin-induced DNA damage and apoptosis in cardiomyocytes in mice. Life Sci. Sep. 15, 2020:257:118074. 9 pages.
Monti et al., Protective effect of the nitroxide tempol against the cardiotoxicity of adriamycin. Free Radic Biol Med. 1996;21(4):463-70.
Moris et al., The role of reactive oxygen species in myocardial redox signaling and regulation. Ann Transl Med. Aug. 2017;5(16):324. 8 pages.
Murphy et al., Hydrogen sulfide signaling in mitochondria and disease. FASEB J. Dec. 2019;33(12):13098-13125.
Murphy et al., Mitochondria as a therapeutic target for common pathologies. Nat Rev Drug Discov. Dec. 2018;17(12):865-886.
Murphy et al., Targeting antioxidants to mitochondria by conjugation to lipophilic cations. Annu Rev Pharmacol Toxicol. 2007:47:629-56.
Murphy. Targeting lipophilic cations to mitochondria. Biochim Biophys Acta. Jul.-Aug. 2008;1777(7-8):1028-31.
Mustafa et al., H2S signals through protein S-sulfhydration. Sci Signal. Nov. 10, 2009;2(96):ra72. 9 pages.
Ocana-Santero et al., Future Prospects of Gene Therapy for Friedreich's Ataxia. Int J Mol Sci. Feb. 11, 2021;22(4):1815. 17 pages.
Ohwada et al., Distinct intra-mitochondrial localizations of pro-survival kinases and regulation of their functions by DUSP5 and PHLPP-1. Biochim Biophys Acta Mol Basis Dis. Oct. 1, 2020;1866(10):165851. 11 pages.
Ordonez et al., Sulforaphane exhibits antiviral activity against pandemic SARS-CoV-2 and seasonal HCoV-OC43 coronaviruses in vitro and in mice. Commun Biol. Mar. 18, 2022;5(1):242. 11 pages.
Pan et al., Persulfide reactivity in the detection of protein s-sulfhydration. ACS Chem Biol. 2013;8(6):1110-6.
Pandey et al., Frataxin directly stimulates mitochondrial cysteine desulfurase by exposing substrate-binding sites, and a mutant Fe—S cluster scaffold protein with frataxin-bypassing ability acts similarly. J Biol Chem. Dec. 27, 2013;288(52):36773-86.
Pandolfo. Friedreich ataxia: the clinical picture. J Neurol. Mar. 2009:256 Suppl 1:3-8.
Pandolfo. Friedreich's ataxia: clinical aspects and pathogenesis. Semin Neurol. 1999;19(3):311-21.
Paradies et al., Role of Cardiolipin in Mitochondrial Function and Dynamics in Health and Disease: Molecular and Pharmacological Aspects. Cells. Jul. 16, 2019;8(7):728. 21 pages.
Park et al., Persulfides: current knowledge and challenges in chemistry and chemical biology. Mol Biosyst. Jul. 2015;11(7):1775-85.
Park et al., ROS-mediated autophagy increases intracellular iron levels and ferroptosis by ferritin and transferrin receptor regulation. Cell Death Dis. Oct. 28, 2019;10(11):822. 10 pages.
Park et al., Use of the "tag-switch" method for the detection of protein S-sulfhydration. Methods Enzymol. 2015:555:39-56.
Patra et al., Mechanism of activation of the human cysteine desulfurase complex by frataxin. Proc Natl Acad Sci U S A. Sep. 24, 2019;116(39):19421-19430.
Pereira et al., Cardiac cytochrome c and cardiolipin depletion during anthracycline-induced chronic depression of mitochondrial function. Mitochondrion. Sep. 2016:30:95-104.
Perez et al., Evaluating prodrug strategies for esterase-triggered release of alcohols. ChemMedChem. Oct. 2013;8(10):1662-7.
Powell et al., A Persulfide Donor Responsive to Reactive Oxygen Species: Insights into Reactivity and Therapeutic Potential. Angew Chem Int Ed Engl. May 22, 2018;57(21):6324-6328.
PubChem-SID-104477302. Modify Date: Feb. 18, 2011. 7 pages.
Puglisi et al., The role of chaperones in iron-sulfur cluster biogenesis. FEBS Lett. Dec. 2018;592(24):4011-4019.
Ravindran et al., Sodium Thiosulfate Preconditioning Ameliorates Ischemia/Reperfusion Injury in Rat Hearts Via Reduction of Oxidative Stress and Apoptosis. Cardiovasc Drugs Ther. Dec. 2017;31(5-6):511-524.
Reichardt et al., Risk-benefit of dexrazoxane for preventing anthracycline-related cardiotoxicity: re-evaluating the European labeling. Future Oncol. Oct. 2018;14(25):2663-2676.
Rocha et al., Protective effects of mito-TEMPO against doxorubicin cardiotoxicity in mice. Cancer Chemother Pharmacol. Mar. 2016;77(3):659-62.
Rotig et al., Aconitase and mitochondrial iron-sulphur protein deficiency in Friedreich ataxia. Nat Genet. Oct. 1997;17(2):215-7.
Rouault et al., Biogenesis and functions of mammalian iron-sulfur proteins in the regulation of iron homeostasis and pivotal metabolic pathways. J Biol Chem. Aug. 4, 2017;292(31):12744-12753.
Rouault et al., Iron-sulfur cluster biogenesis and human disease. Trends Genet. Aug. 2008;24(8):398-407.
Rouault. The indispensable role of mammalian iron sulfur proteins in function and regulation of multiple diverse metabolic pathways. Biometals. Jun. 2019;32(3):343-353.
Sawyer. Anthracyclines and heart failure. N Engl J Med. Mar. 21, 2013;368(12):1154-6.
Shi et al., Both human ferredoxins 1 and 2 and ferredoxin reductase are important for iron-sulfur cluster biogenesis. Biochim Biophys Acta. Feb. 2012;1823(2):484-92.
Shi et al., Mitochondria-Targeting Small Molecules Effectively Prevent Cardiotoxicity Induced by Doxorubicin. Molecules. Jun. 19, 2018;23(6):1486.
Shioji et al., Overexpression of thioredoxin-1 in transgenic mice attenuates adriamycin-induced cardiotoxicity. Circulation. Sep. 10, 2002;106(11):1403-9.
Siegel et al., Cancer Statistics, 2021. CA Cancer J Clin. Jan. 2021;71(1):7-33.
Singal et al., Doxorubicin-induced cardiomyopathy. N Engl J Med. Sep. 24, 1998;339(13):900-5.
Sivakumaran et al., HNO enhances SERCA2a activity and cardiomyocyte function by promoting redox-dependent phospholamban oligomerization. Antioxid Redox Signal. Oct. 10, 2013;19(11):1185-97.
Sourris et al., Ubiquinone (coenzyme Q10) prevents renal mitochondrial dysfunction in an experimental model of type 2 diabetes. Free Radic Biol Med. Feb. 1, 2012;52(3):716-723.
Sterba et al., Oxidative stress, redox signaling, and metal chelation in anthracycline cardiotoxicity and pharmacological cardioprotection. Antioxid Redox Signal. Mar. 10, 2013;18(8):899-929.
Sui et al., The role of Nrf2 in astragaloside IV-mediated antioxidative protection on heart failure. Pharm Biol. 2020, 58 (1), 1201-1207.
Tocchetti et al., GSH or palmitate preserves mitochondrial energetic/redox balance, preventing mechanical dysfunction in metabolically challenged myocytes/hearts from type 2 diabetic mice. Diabetes. Dec. 2012;61(12):3094-105.
Tominaga et al., A water-soluble tetrazolium salt useful for colorimetric cell viability assay. Anal. Commun., 1999, 36, 47-50.
Torres-Gonzalez et al., Mitochondrial 8-oxoguanine glycosylase decreases mitochondrial fragmentation and improves mitochondrial function in H9C2 cells under oxidative stress conditions. Am J Physiol Cell Physiol. Feb. 1, 2014;306(3):C221-9.
Untereiner et al., Decreased Gluconeogenesis in the Absence of Cystathionine Gamma-Lyase and the Underlying Mechanisms. Antioxid Redox Signal. Jan. 20, 2016;24(3):129-40.
Untereiner et al., Stimulatory effect of CSE-generated H2S on hepatic mitochondrial biogenesis and the underlying mechanisms. Nitric Oxide. Aug. 31, 2016:58:67-76.
Ventura-Clapier et al., Transcriptional control of mitochondrial biogenesis: the central role of PGC-1alpha. Cardiovasc Res. Jul. 15, 2008;79(2):208-17.
Vile et al., dl-N,N'-dicarboxamidomethyl-N,N'-dicarboxymethyl-1,2-diaminopropane (ICRF-198) and d-1,2-bis(3,5-dioxopiperazine-1-yl)propane (ICRF-187) inhibition of Fe3+ reduction, lipid peroxidation, and CaATPase inactivation in heart microsomes exposed to adriamycin. Cancer Res. Apr. 15, 1990;50(8):2307-10.
Vincent et al., The role of antioxidants in the era of cardio-oncology. Cancer Chemother Pharmacol. Dec. 2013;72(6):1157-68.

(56) References Cited

OTHER PUBLICATIONS

Wakabayashi et al., Protection against electrophile and oxidant stress by induction of the phase 2 response: fate of cysteines of the Keap1 sensor modified by inducers. Proc Natl Acad Sci U S A. Feb. 17, 2004;101(7):2040-5.
Wallace et al., Hydrogen sulfide-based therapeutics: exploiting a unique but ubiquitous gasotransmitter. Nat Rev Drug Discov. May 2015;14(5):329-45.
Wallace et al., Mitochondrial Determinants of Doxorubicin-Induced Cardiomyopathy. Circ Res. Mar. 27, 2020;126(7):926-941.
Wang et al., Alleviating Cellular Oxidative Stress through Treatment with Superoxide-Triggered Persulfide Prodrugs. Angew Chem Int Ed Engl. Sep. 14, 2020;59(38):16698-16704.
Wang et al., Recent Advances in Chemical Biology of Mitochondria Targeting. Front Chem. May 3, 2021:9:683220. 17 pages.
Westley. Rhodanese. Adv Enzymol Relat Areas Mol Biol. 1973:39:327-68.
Wu et al., Mitochondrial-Targeted Therapy for Doxorubicin-Induced Cardiotoxicity. Int J Mol Sci. Feb. 9, 2022;23(3):1912. 28 pages.
Xiao et al., Metabolic Responses to Reductive Stress. Antioxid Redox Signal. Jun. 2020;32(18):1330-1347.
Yadav et al., Biosynthesis and Reactivity of Cysteine Persulfides in Signaling. J Am Chem Soc. Jan. 13, 2016;138(1):289-99.
Yang et al., Effects of PPARα/PGC-1α on the energy metabolism remodeling and apoptosis in the doxorubicin induced mice cardiomyocytes in vitro. Int J Clin Exp Pathol. Oct. 1, 2015;8(10):12216-24.
Yang et al., S-Persulfidation: Chemistry, Chemical Biology, and Significance in Health and Disease. Antioxid Redox Signal. Nov. 20, 2020;33(15):1092-1114.
Yeh et al., Cardiovascular complications of cancer therapy: incidence, pathogenesis, diagnosis, and management. J Am Coll Cardiol. Jun. 16, 2009;53(24):2231-47.
Youness et al., Targeting hydrogen sulphide signaling in breast cancer. J Adv Res. Jul. 16, 2020:27:177-190.
Yuan et al., Esterase-Sensitive Glutathione Persulfide Donor. Org Lett. Oct. 19, 2018;20(20):6364-6367.
Zarenkiewicz et al., Reaction of Nitroxyl (HNO) with Hydrogen Sulfide and Hydropersulfides. J Org Chem. Jan. 1, 2021;86(1):868-877.
Zhang et al., Hydrogen Sulfide (H2S)-Releasing Compounds: Therapeutic Potential in Cardiovascular Diseases. Front Pharmacol. Sep. 21, 2018:9:1066. 17 pages.
Zhang et al., Identification of the molecular basis of doxorubicin-induced cardiotoxicity. Nat Med. Nov. 2012;18(11):1639-42.
Zhang et al., Reductive stress in cancer. Adv Cancer Res. 2021:152:383-413.
Zhao et al., Fluorogenic hydrogen sulfide (H2S) donors based on sulfenyl thiocarbonates enable H2S tracking and quantification. Chem Sci. Dec. 10, 2018;10(6):1873-1878.
Zhao et al., Protective effects of berberine on doxorubicin-induced hepatotoxicity in mice. Biol Pharm Bull. 2012;35(5):796-800.
Zheng et al., An Esterase-Sensitive Prodrug Approach for Controllable Delivery of Persulfide Species. Angew Chem Int Ed Engl. Sep. 18, 2017;56(39):11749-11753.
Zheng et al., Esterase-Sensitive Prodrugs with Tunable Release Rates and Direct Generation of Hydrogen Sulfide. Angew Chem Int Ed Engl. Mar. 24, 2016;55(14):4514-8.
Zhu et al., A mouse model for juvenile doxorubicin-induced cardiac dysfunction.Pediatr Res. Nov. 2008;64(5):488-94.
Zhu et al., Dysfunction of the PGC-1α-mitochondria axis confers adriamycin-induced podocyte injury. Am J Physiol Renal Physiol. Jun. 15, 2014;306(12):F1410-7.
Zielonka et al., Mitochondria-Targeted Triphenylphosphonium-Based Compounds: Syntheses, Mechanisms of Action, and Therapeutic and Diagnostic Applications. Chem Rev. Aug. 9, 2017;117(15):10043-10120.

ALKYLSULFENYL THIOCARBONATES: PRECURSORS TO HYDROPERSULFIDES POTENTLY ATTENUATE OXIDATIVE STRESS

RELATED APPLICATION INFORMATION

This application is a national stage application under 35 U.S.C. § 371 of PCT/US2022/027101, filed Apr. 29, 2022, which claims priority to U.S. Application No. 63/181,758 filed on Apr. 29, 2021.

STATEMENT OF GOVERNMENTAL INTEREST

This invention was made with government support under grant CHE-1900285 awarded by the National Science Foundation. The government has certain rights in the invention.

BACKGROUND

Hydrogen sulfide ($H_2S$) has been recently reported to exert several favorable physiological effects including vasorelaxation, inhibition of myocardial ischemia-reperfusion injury, and slowing the development of atherosclerosis. Zhang et al., 2018; Kimura, 2014; Barr and Calvert, 2014. Many of the biological effects of $H_2S$ have been attributed to the formation of hydropersulfide (RSSH) species. Fukuto et al., 2018; Filipovic et al., 2018; Mustafa et al., 2009. Indeed, recent studies have demonstrated that RSSH species, such as cysteine hydropersulfide (Cys-SSH) and glutathione hydropersulfide (GSSH), are endogenously produced at significant levels in various organisms, including mammals. Ida et al., 2014; Kunikata et al., 2017.

Further, cysteine residues in a variety of proteins and enzymes have been reported to be modified to the corresponding hydropersulfides. Dóka et al., 2016; Longen et al., 2016. The chemical properties and abundance of these species suggest that RSSH play important roles in various physiological processes. Fukuto et al., 2020. CysSSH can be generated via the enzymes cystathionine γ-lyase (CSE) and cystathionine β-synthase (CBS), both of which utilize cystine (CysSSCys) as a substrate. Ida et al., 2014; Yadav et al., 2016. In addition, recently it has been reported that CysSSH can be synthesized by cysteinyl-tRNA synthetases (CARSs) utilizing CysSH as a substrate. Akaike et al., 2017. The reaction of $H_2S$ with oxidized thiols, such as disulfides (RSSR) and sulfenic acids (RSOH), also can generate RSSH. Cuevasanta et al., 2015. Despite these findings, the physiological functions of RSSH remain poorly understood.

RSSH species possess unique chemical properties that are not found in other biologically relevant sulfur species. For instance, RSSH are significantly more nucleophilic than their thiol (RSH) counterparts, likely due to the alpha effect. Cuevasanta et al., 2015; Benchoam et al., 2020; Zarenkiewicz et al., 2021. Additionally, RSSH have been proposed to behave as potent antioxidants and may play an important role in maintaining the cellular redox balance. Álvarez et al., 2017. The high nucleophilicity of RSSH can result in the efficient scavenging of reactive electrophiles. Recently, Fukuto and co-workers have reported that increased levels of intracellular RSSH exhibit enhanced resistance to electrophilic stress in HEK293T cells. Bianco et al., 2019. Furthermore, Akaike and co-workers demonstrated that CSE overexpression leads to increased intracellular levels of RSSH species in A549 cells, which confers resistance toward hydrogen peroxide ($H_2O_2$)-mediated oxidative stress. Ida et al., 2014.

Interestingly, unlike RSH, RSSH in the protonated state are electrophilic and can react with nucleophiles, including RSH. The electrophilic properties of RSSH may result in nucleophilic attack by protein thiols (PSH) giving rise to generation of protein hydropersulfides (PSSH). In fact, this transformation has been proposed to protect protein thiols from irreversible modification during oxidative and/or electrophilic insult. Fukuto et al., 2020. Consistent with this hypothesis, Greiner and co-workers demonstrated that the phosphatase and tensin homolog (PTEN) is protected from irreversible $H_2O_2$-mediated inhibition when the protein is in the PSSH form. Greiner et al., 2013. Accumulating evidence suggests that the electrophilic nature of RSSH serves to regulate redox signaling and contribute to various cellular functions. Kasamatsu et al., 2016. For example, RSSH can activate the transcription factor, nuclear factor erythroid 2-related factor 2 (Nrf2) by reacting with the thiol group on Kelch-like ECH-associated protein 1 (KEAP1), which leads to cellular protection by expressing antioxidant response element (ARE)-dependent genes. Koike et al., 2017.

Thus, the chemical properties of RSSH are distinct and far more diverse than thiols. Due to the dichotomy of their nucleophilic and electrophilic character, however, RSSH are intrinsically unstable and subject to rapid disproportionation reactions to produce multiple species including polysulfides, $H_2S$, and sulfur ($S_8$). The metastable nature of RSSH remains a bottleneck in developing RSSH-based therapeutics.

One approach employed to address the intrinsic instability of RSSH relies on donor molecules capable of releasing RSSH in situ. To date, various donors have been developed in which the terminal sulfhydryl group is masked with a suitable protecting group. In the presence of specific stimuli such as cellular thiols, Yang et al., 2019, reactive oxygen species (ROS), Bora et al., 2018; Wang et al., 2020; Powell et al., 2018; pH, Kang et al., 2018; Artaud and Galardon, 2014; Khodade and Toscano, 2018; Khodade et al., 2020; light, Chaudhuri et al., 2019, or esterase, Zheng et al., 2017; Yuan et al., 2018, these donors release RSSH. Notably, many of these precursors exhibit cytoprotective and cardioprotective effects, suggesting their potential application as reactive sulfur species-based therapeutics. Although several RSSH donor molecules have been developed, a significant limitation of current precursors is the lack of controllable RSSH release rates. In addition, some RSSH donors produce electrophilic byproducts that can complicate biological studies. Accessing RSSH donors with varying release kinetics under physiological conditions is necessary to evaluate the impact on potential therapeutic applications.

SUMMARY

The presently disclosed subject matter provides alkylsulfenyl thiocarbonates as a new class of RSSH precursors that efficiently release RSSH under physiologically relevant conditions.

More particularly, in some aspects, the presently disclosed subject matter provides a compound of formula (I):

(I)

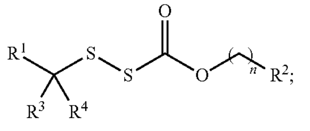

wherein: n is 0 or 1;

$R^1$ is

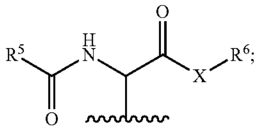

wherein $R^5$ and $R^6$ are each independently $C_1$-$C_4$ substituted or unsubstituted alkyl, and substituted or unsubstituted aryl; X is O or NH; $R^2$ is substituted or unsubstituted aryl; $R^3$ and $R^4$ are each independently H or $C_1$-$C_4$ substituted or unsubstituted alkyl; and pharmaceutically acceptable salts thereof.

In certain aspects, the compound of formula (I) is:

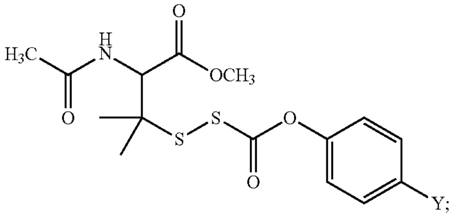

wherein Y is selected from the group consisting of H, $C_1$-$C_4$ alkyl, $C_1$-$C_4$ alkoxyl, NRR' where R and R' are each independently H or $C_1$-$C_4$ substituted or unsubstituted alkyl, —$CF_3$, halogen, and cyano.

In particular aspects, the compound of formula (I) is selected from the group consisting of:

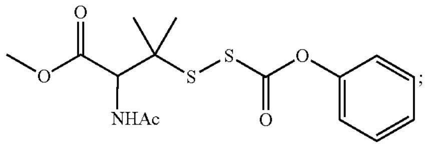

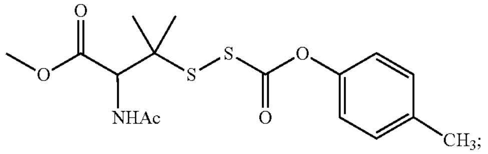

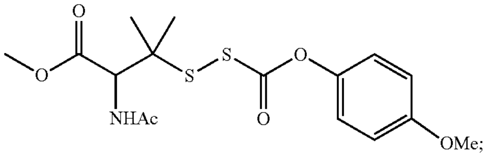

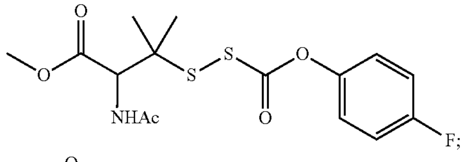

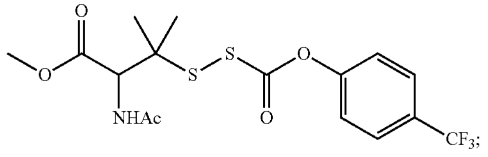

-continued

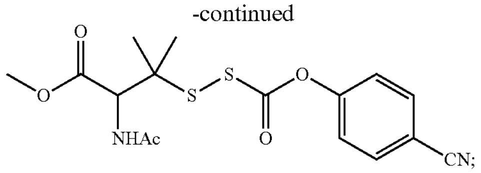

In other aspects, the compound of formula (I) is:

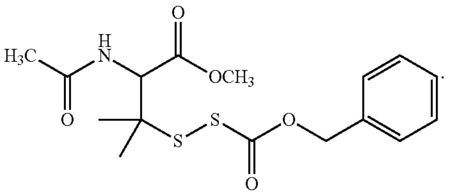 [SMILES: COC(=O)C(NC(C)=O)C(C)(C)SSC(=O)OCc1ccccc1]

In some aspects, the presently disclosed subject matter provides a pharmaceutical composition comprising a compound of formula (I) and a pharmaceutically acceptable carrier.

The presently disclosed subject matter further provides kits comprising one or more compounds of formula (I) as described herein.

In yet other aspects, the presently disclosed subject matter provides a method for treating a disorder, disease, or condition associated with oxidative stress in a subject in need of treatment thereof, the method comprising administering to the subject a therapeutically effective amount of a compound of formula (I) or a pharmaceutical composition thereof.

In particular aspects, the disorder, disease, or condition associated with oxidative stress comprises ischemia/reperfusion injury. In yet more particular aspects, the treating comprises preventing, reducing the occurrence of or severity of, or protecting against ischemia/reperfusion injury. In certain aspects, the ischemia/reperfusion injury comprises myocardial ischemia/reperfusion injury.

In other aspects, the presently disclosed subject matter provides a method for preventing or reducing ischemia/reperfusion injury to an organ to be transplanted, the method comprising administering to or contacting the organ with a therapeutically effective amount of a compound of formula (I) or a pharmaceutical composition thereof.

In other aspects, the presently disclosed subject matter provides a method for treating a disorder, disease, or condition associated with impaired Fe—S cluster biosynthesis, the method comprising administering to a subject in need of treatment thereof, a therapeutically effective amount of a compound of formula (I). In certain aspects, the disorder, disease, or condition associated with impaired Fe—S cluster biosynthesis is selected from Friedreich's Ataxia, sideroblastic anemia, and myopathy. In particular aspects, the disorder, disease, or condition associated with impaired Fe—S cluster biosynthesis comprises Friedreich's Ataxia.

In other aspects, the presently disclosed subject matter provides a method for treating anthracycline-induced cardiotoxicity in a subject in need of treatment thereof, the method comprising administering to the subject a therapeutically effective amount of a compound of formula (I). In certain aspects, the subject is being treated with, has been treated with, or is expected to being treating with one or more anthracyclines. In more certain aspects, the subject is administered a compound of formula (I) before beginning treatment with an anthracycline, during treatment with an anthracycline, or after treatment with an anthracycline. In particular aspects, the one or more anthracyclines are selected from daunorubicin, doxorubicin, epirubicin, idarubicin, mitoxantrone, valrubicin, and combinations thereof.

In certain aspects, the subject is being treated for cancer. In more certain aspects, the cancer is selected from acute lymphocytic leukemia, acute myelogenous leukemia, Hodgkin's lymphoma, non-Hodgkin's lymphoma, bladder cancer, breast cancer, metastatic breast cancer, ovarian cancer, osteogenic sarcoma, Ewing sarcoma, soft tissue sarcoma, thyroid cancer, neuroblastoma, Wilms' tumor, small cell lung cancer, advanced endometrial carcinoma, metastatic hepatocellular cancer, multiple myeloma, advanced renal cell carcinoma, thymomas and thymic malignancies, uterine sarcoma, and Waldenstrom macroglobulinemia.

In certain aspects, the subject is afflicted with or at risk of developing cardiomyopathy and/or heart failure.

In other aspects, the presently disclosed subject matter provides a method for treating COVID-19, the method comprising administering to a subject in need of treatment thereof a therapeutically effective amount of a compound of formula (I).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
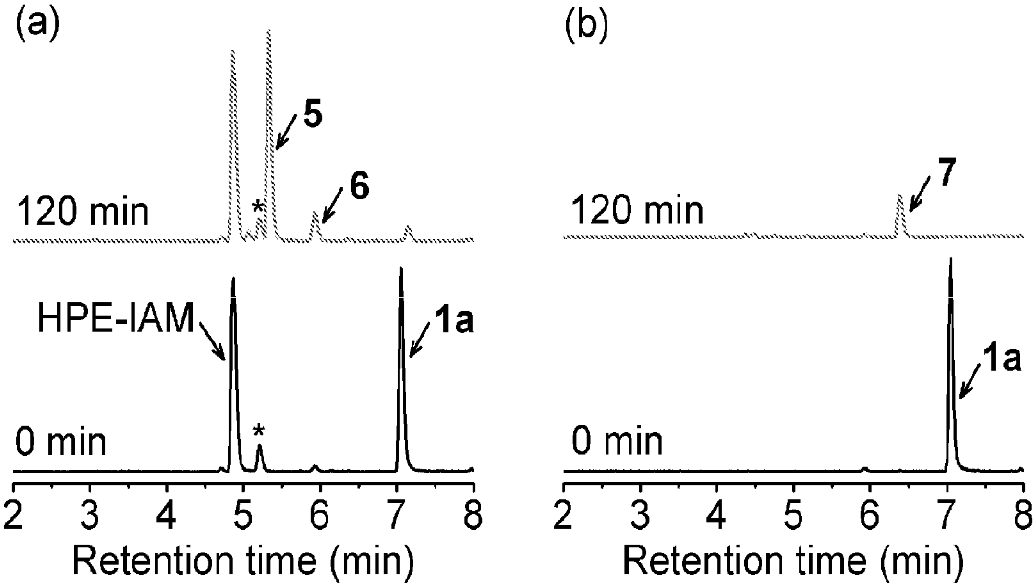
Figure 3:
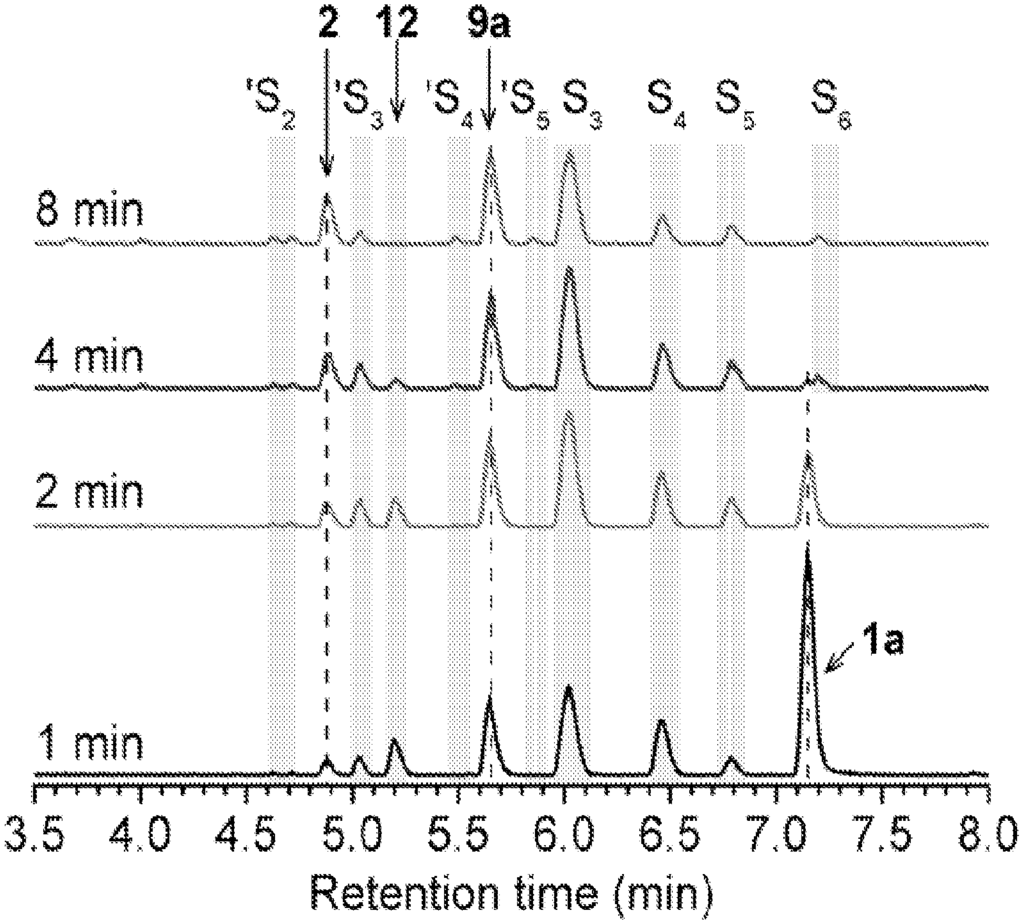
Figure 4:
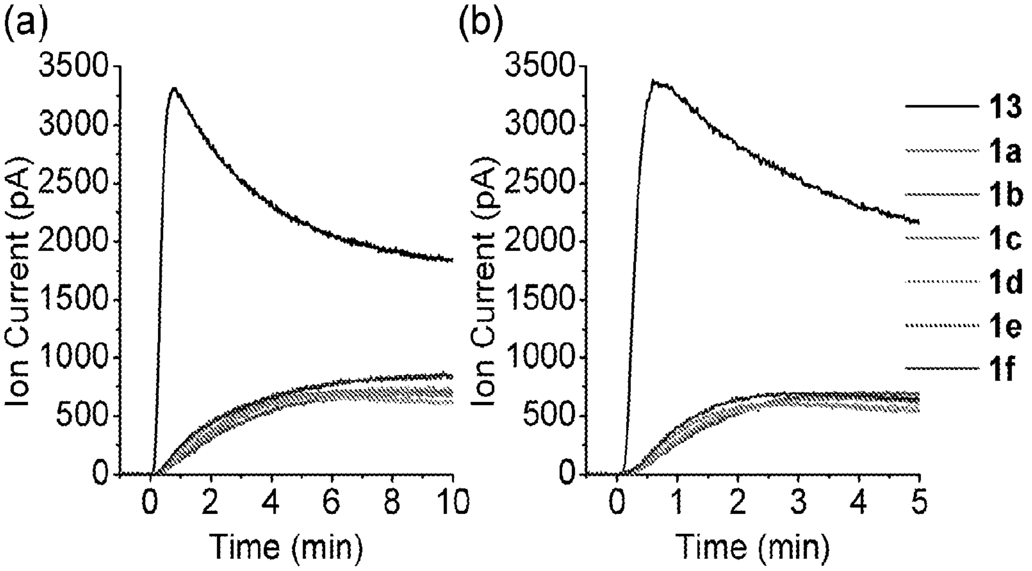
Figure 5:
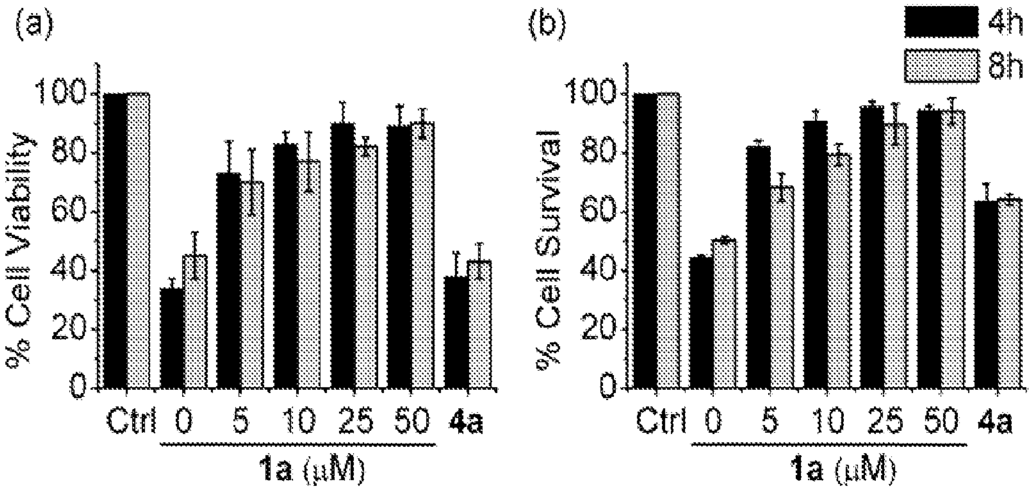
Figure 6:
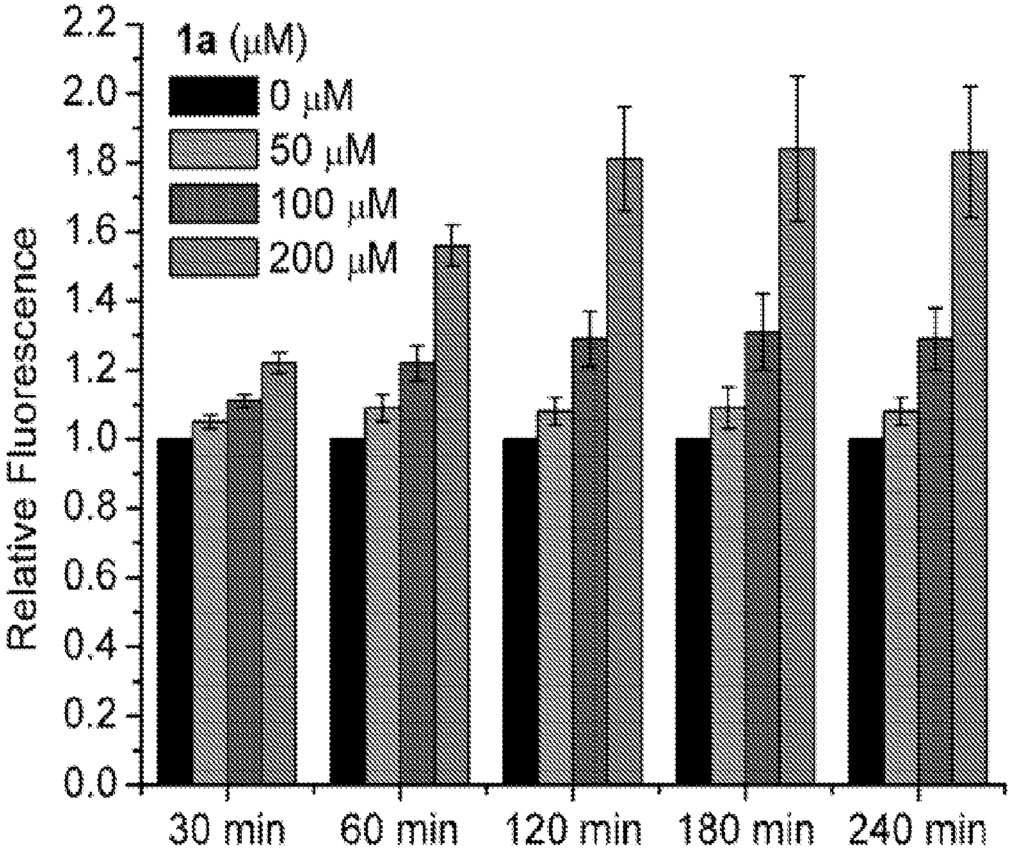
Figure 7:
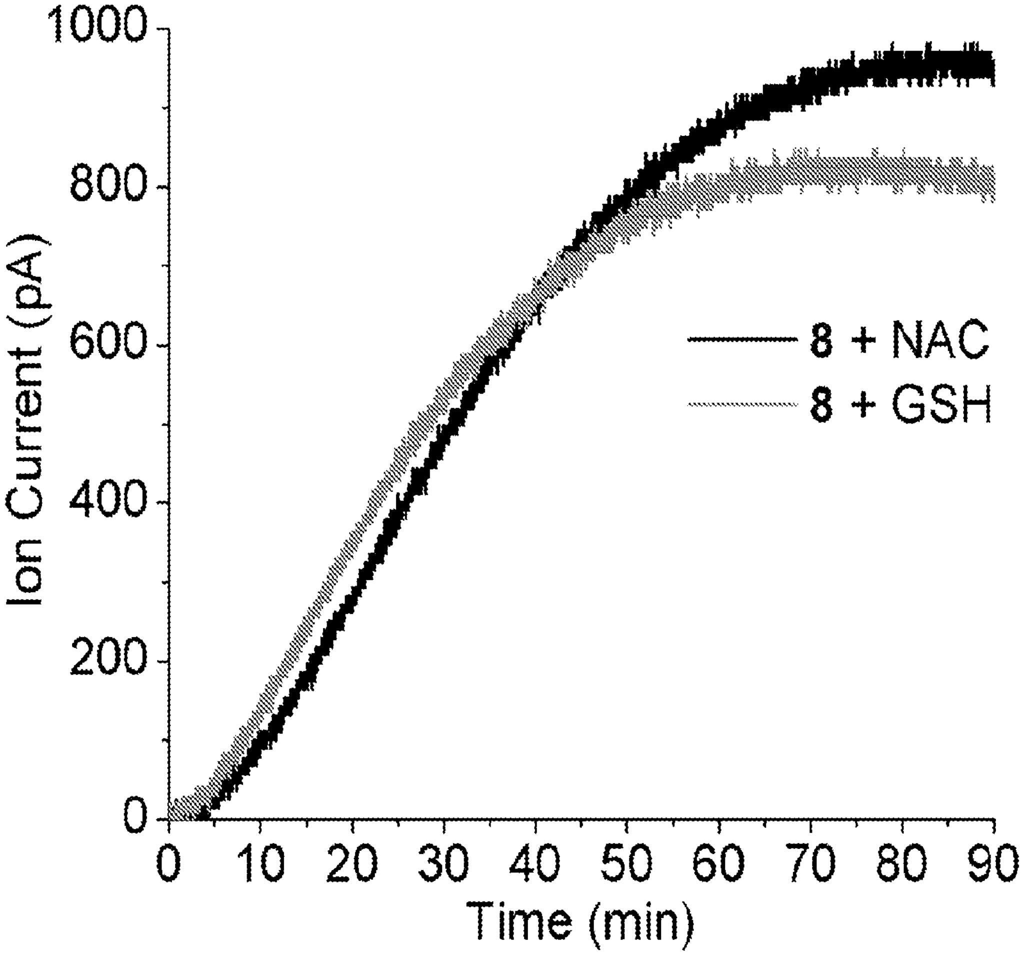
Figure 8:
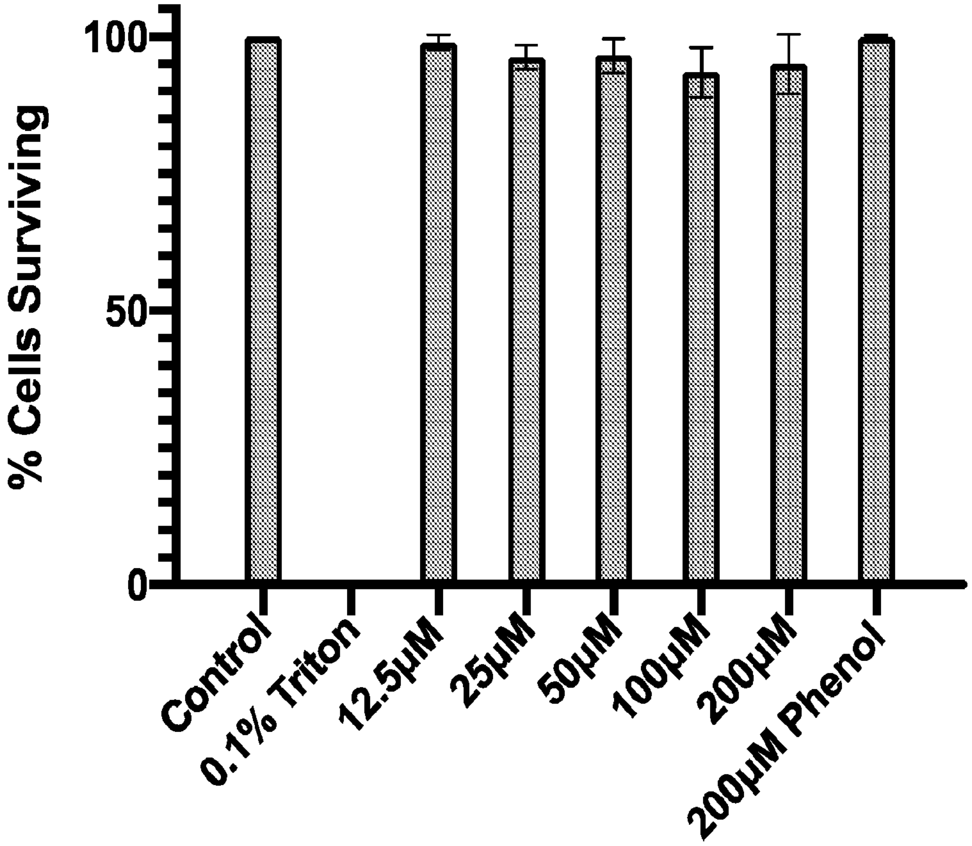
Figure 10:
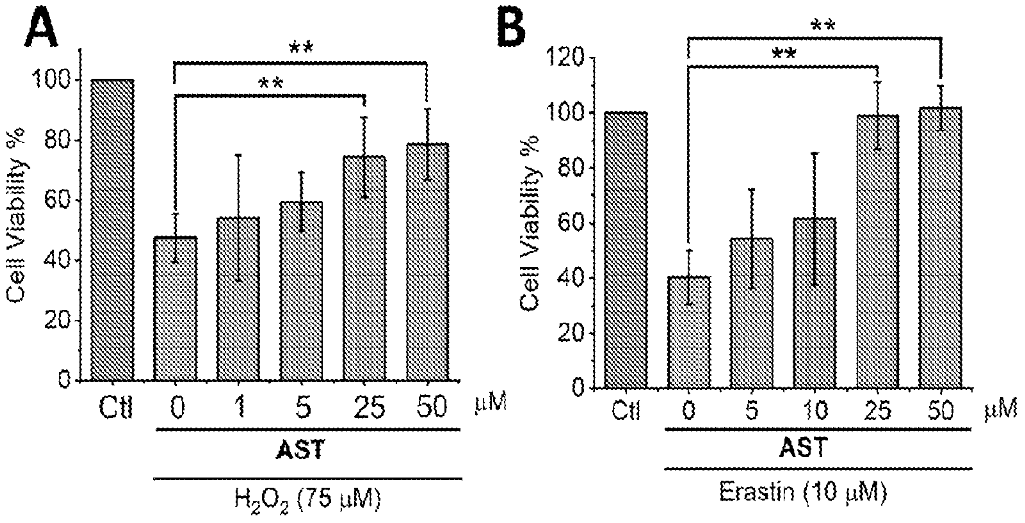
Figure 11:
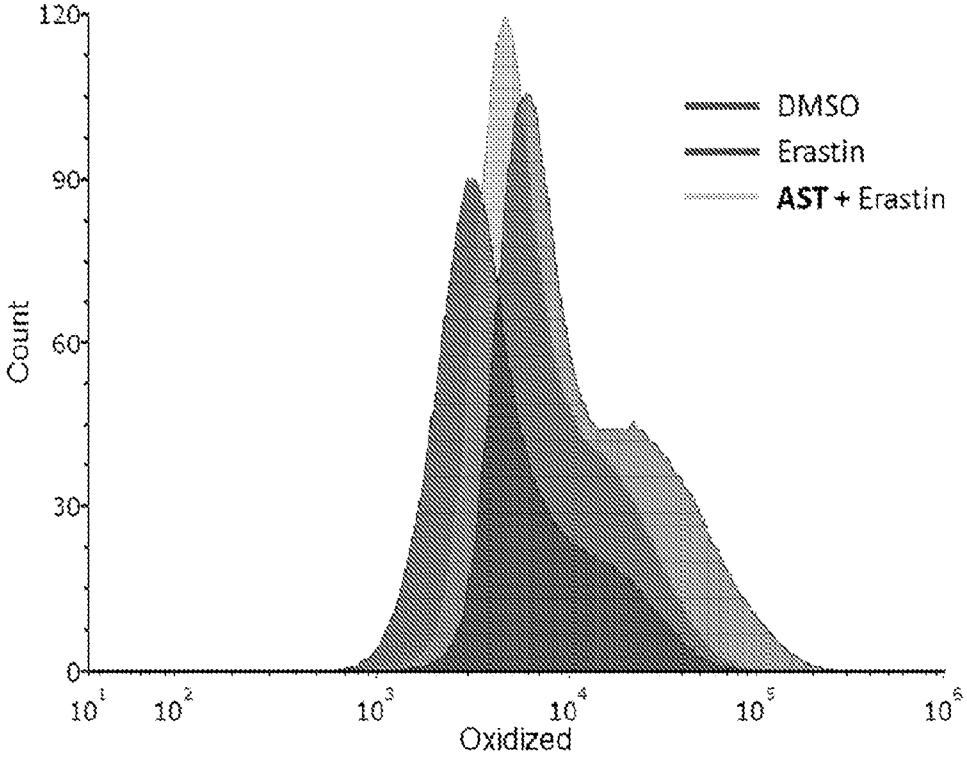
Figure 12:
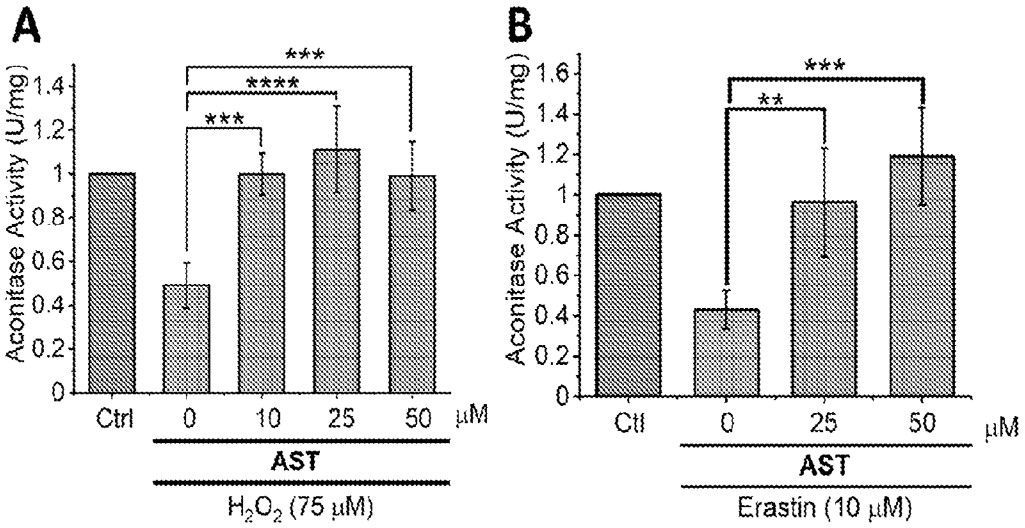
Figure 13:
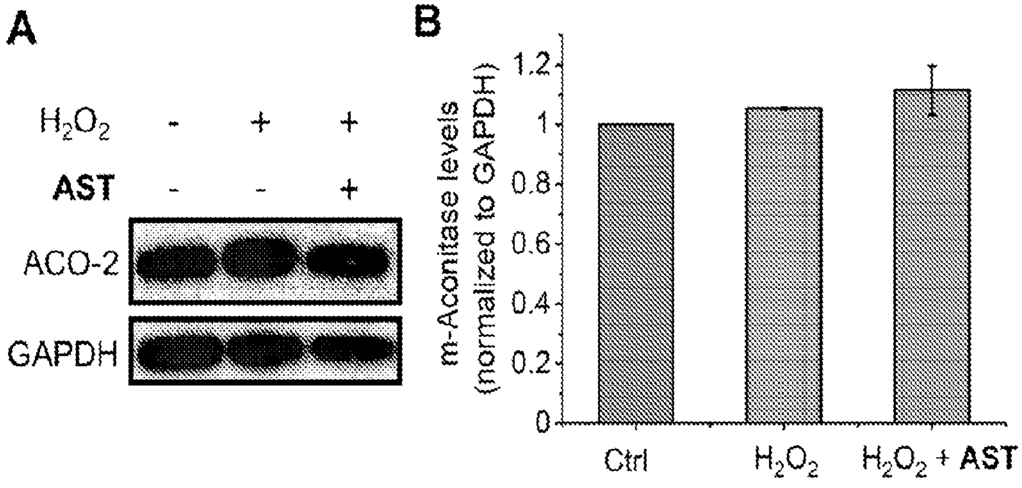
Figure 14:
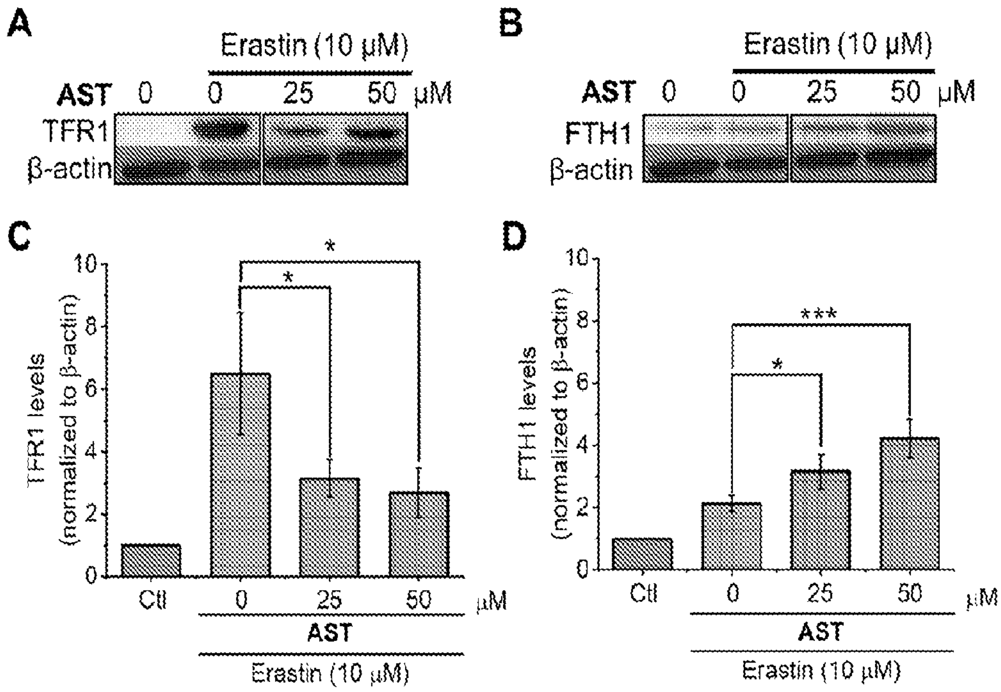
Figure 15:
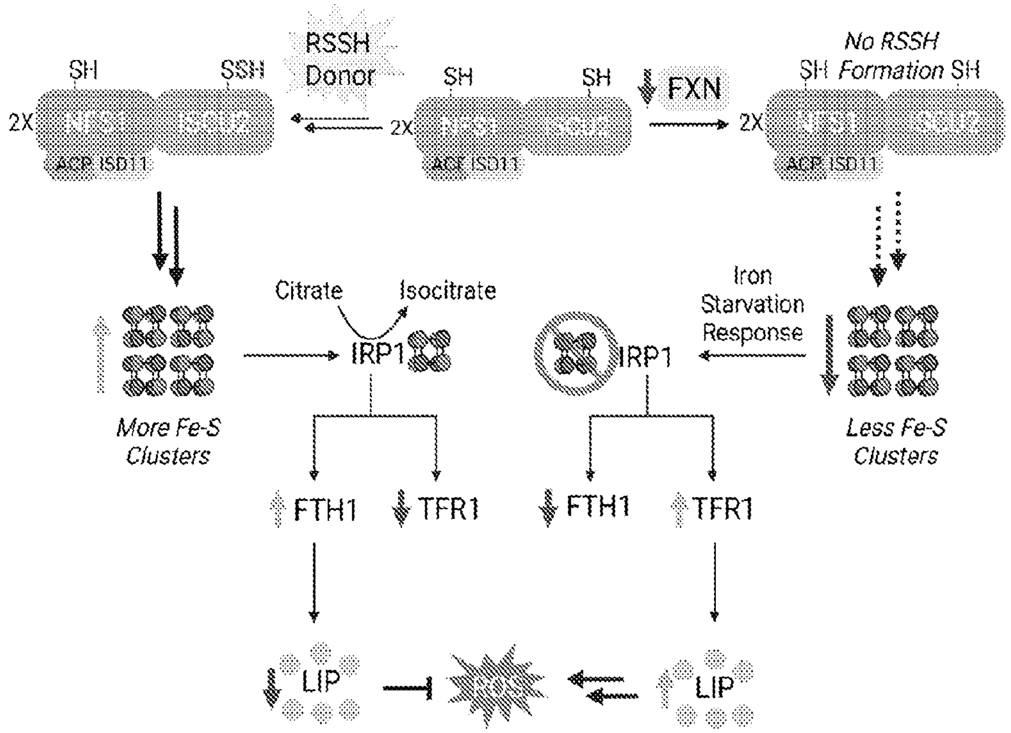
Figure 16:
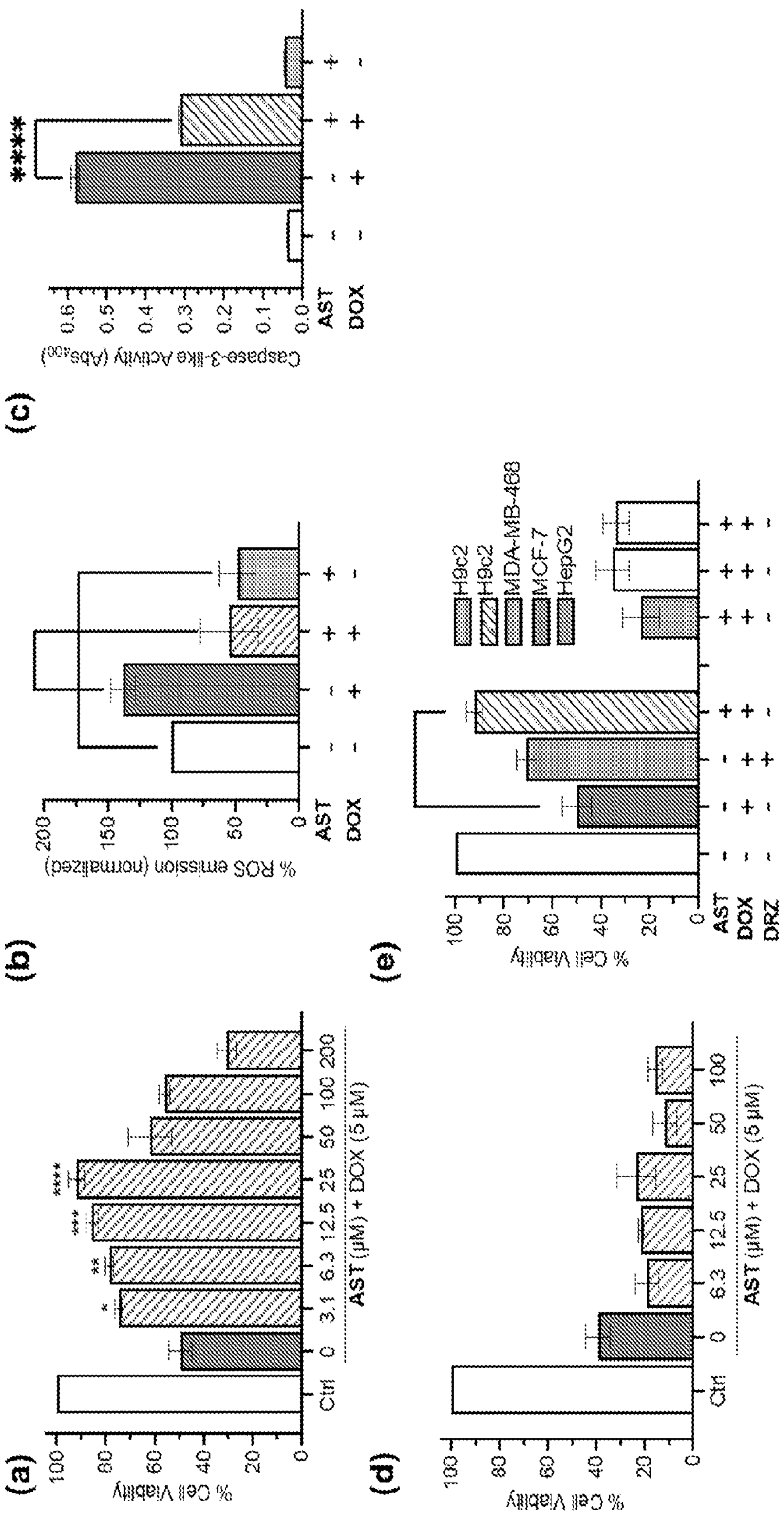
Figure 17:
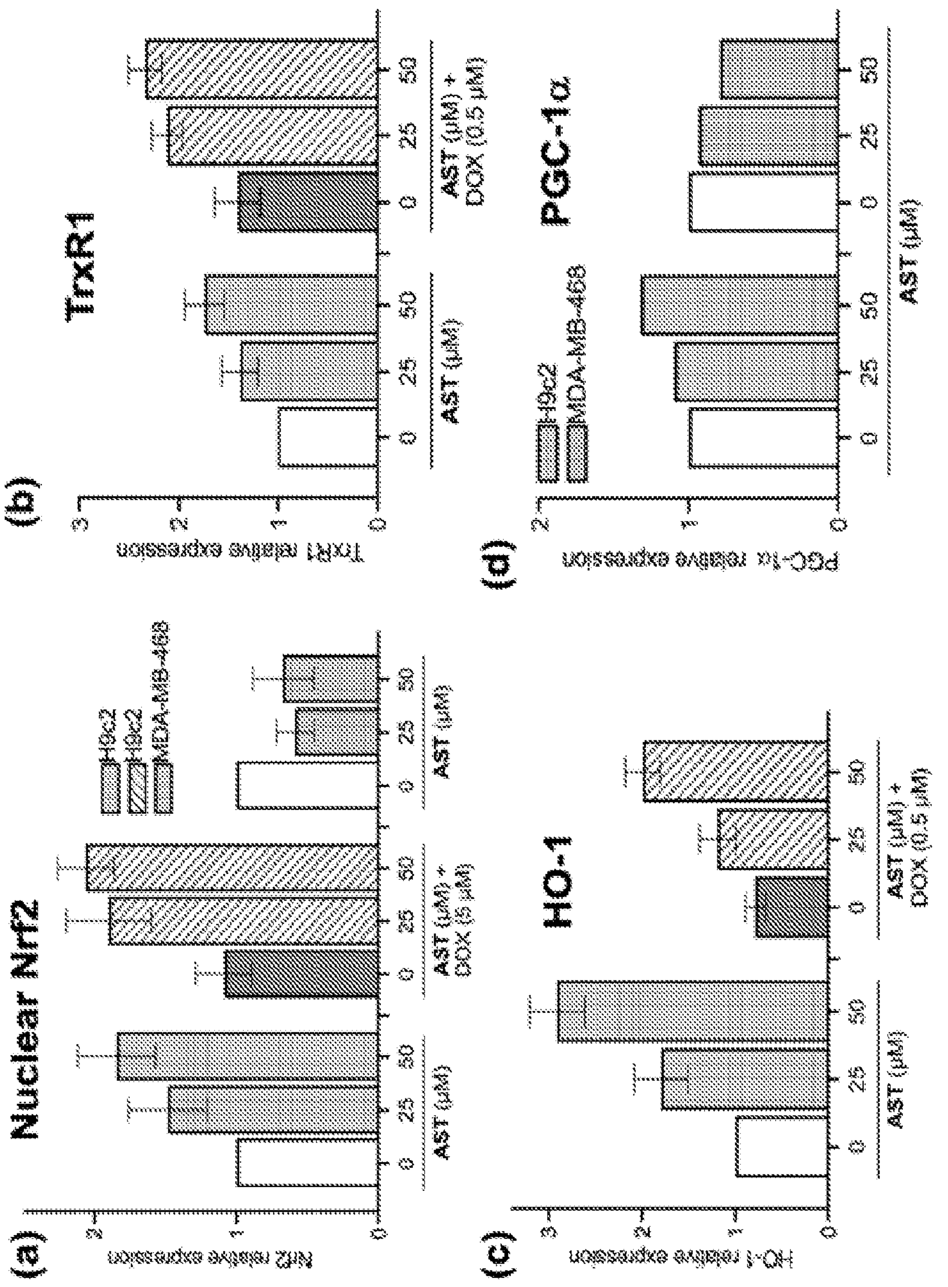
Figure 18:
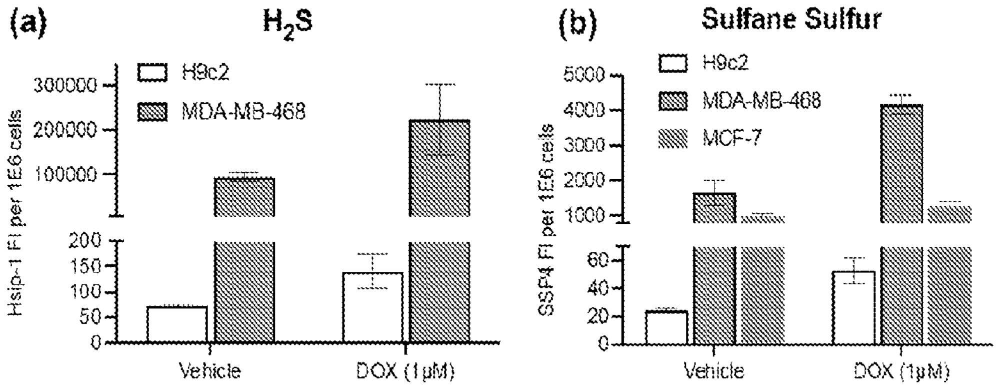

Having thus described the presently disclosed subject matter in general terms, reference will now be made to the accompanying Figures, which are not necessarily drawn to scale, and wherein:

FIG. 1A and FIG. 1B are UPLC-MS traces showing RSSH generation from 1a (100 μM) in the presence of (FIG. 1A) HPE-IAM (1 mM), and (FIG. 1B) MMTS (1 mM) in ammonium bicarbonate buffer (pH 7.4, 50 mM) containing the metal chelator diethylenetriaminepentaacetic acid (DTPA) (100 μM) at 37° C. Asterisk indicates the presence of an impurity in the commercial HPE-IAM sample;

FIG. 2A and FIG. 2B are (FIG. 2A) HPLC traces showing hydrolysis of 1a (100 μM) in the presence of MMTS (1 mM) in PBS (pH 7.4, 100 mM) containing the metal chelator DTPA (100 μM) at 37° C. An aliquot of the reaction mixture was withdrawn at the specified time and quenched with 0.1% formic acid. The decay of 1a was monitored at 240 nm and formation of phenol 4a at 275 nm. (FIG. 2B) Kinetics of 1a decomposition and phenol 4a formation. Data represent the average of three experiments. The curve is the calculated best fit to a single-exponential function;

FIG. 3 shows UPLC-MS chromatograms of RSSH generation from 1a (100 μM) in the presence of NAC (500 μM) in pH 7.4 ammonium bicarbonate (50 mM) containing the metal chelator DTPA (100 μM) at 37° C. Aliquots taken at various times were quenched with 1% formic acid, and analyzed by UPLC-MS. RSSH-derived symmetrical dialkyl polysulfide, labeled as $S_3$ to $S_6$ ($R^1SS_nSR^1$, n=1-4, cyan highlight), and unsymmetrical dialkyl polysulfides labeled as '$S_2$ to '$S_5$ ($R^1SS_nSR^2$, n=0-3, pink highlight) formation is evident. A peak at 5.65 min attributed to thiocarbonate 10 also is observed;

FIG. 4A and FIG. 4B show COS MIMS signals at m/z 60 observed following the reaction of control compound 9 (50 μM) and RSSH precursors 1a-f (50 μM) with (FIG. 4A) NAC, and (FIG. 4B) GSH (0.25 mM, 5 equiv) in PBS (pH 7.4, 10 mM) with DTPA (100 μM) at 37° C.;

FIG. 5A and FIG. 5B show cell viability of H9c2 cardiac myoblasts pretreated with RSSH precursor 1a at 0, 5, 10, 25, and 50 μM and the byproduct phenol 4a at 50 μM for 4 and 8 h followed by exposure to $H_2O_2$ (200 μM) for 2 h. (FIG. 5A) Quantification of viability was carried out using Cell Counting Kit-8 (CCK-8). Results are expressed as the mean±SEM (n=5 for each treatment group) with three independent experiments. (FIG. 5B) Quantification of cytotoxicity was carried out using Sytox Green nucleic acid stain. Results are expressed as the mean±SEM (n=5 for each treatment group) with five independent experiments;

FIG. 6 shows the intracellular RSSH release in H9c2 cardiac myoblasts. H9c2 cells were pre-treated with SSP4 (20 μM) and CTAB (500 μM) for 20 min, followed by incubation with RSSH precursor 1a at 0, 50, 100, and 200 μM. Fluorescence intensity was measured at the indicated times. Results are normalized to the 0 μM value at each time point and expressed as the mean±SEM (n=3 for each treatment group) with three independent experiments;

FIG. 7 shows the COS measurement using MIMS generated from the RSSH precursor 8 (50 μM) with NAC, and GSH (0.25 mM, 5 equiv.) in PBS (pH 7.4, 10 mM) with DTPA (100 μM) at 37° C.;

FIG. 8 is a cell viability assay conducted on H9c2 cells with Precursor 1a (12.5, 50, 100 and 200 μM) and byproduct phenol (4a) (200 μM) using Sytox Green nucleic acid stain. Results are expressed as the mean±SEM (n=5 for each treatment group) with 3 independent experiments;

FIG. 9A and FIG. 9B show: (FIG. 9A) Mechanism of de novo Fe—S cluster synthesis involving initial desulfuration of cysteine via NFS1 followed by sulfane sulfur transfer to ISCU2. Both steps are facilitated by FXN. (FIG. 9B) Regulation of iron metabolism via Fe—S cluster biosynthesis and consequences of downregulation of FXN. (LIP=labile iron pool);

FIG. 10A and FIG. 10B demonstrate that RSSH protect FA fibroblasts against $H_2O_2$— and erastin-induced cytotoxicity. FIG. 10A, pretreatment of AST with varying concentrations in FA fibroblasts (GM04078, Coriell Institute) for 4 h followed by 4 h treatment with $H_2O_2$. Viability was measured using CCK8 assay. FIG. 10B, pretreatment of AST with varying concentrations in FA fibroblasts for 4 h followed by treatment with erastin for 24 h. Results are expressed as SEM with n≥3 for all concentrations. **P<0.005, for comparisons with the erastin group. Group comparisons are determined by a one-way analysis of variance (ANOVA) with Dunnet's correction post-hoc test using GraphPad Prism 8;

FIG. 11 demonstrates that RSSH inhibits lipid peroxidation. FA fibroblasts were pretreated with AST (50 μM) for 4 h followed by 24 h treatment with erastin (10 μM). The histogram shows the rate in % of the ratiometric dye, BODIBY C-11 (581/591), which is a marker for lipid peroxidation. Blue represents DMSO-treated cells, red represents erastin treated cells, and green represents reduction of lipid peroxidation in live cells pretreated with AST;

FIG. 12A and FIG. 12B shows that: FIG. 12A, pretreatment of AST with varying concentrations in FA fibroblasts for 12 h followed by 12 h treatment with $H_2O_2$ (75 mM). Aconitase activity was measured as a result of formation of NADH and normalized to citrate synthase activity. FIG. 12B, pretreatment of AST with varying concentrations in FA fibroblasts for 4 h followed by 24 h treatment with erastin (10 mM). Assays were conducted on enriched-mitochondrial pellets. Results are the means±SEM of n≥3 for all concentrations. *$P<0.05$, $P<0.005$, *$P<0.0005$, ****$P<0.0001$ for comparisons with the $H_2O_2$ group. Group comparisons are determined by a one-way analysis of variance (ANOVA) with Dunnet's correction post-hoc test using GraphPad Prism 8;

FIG. 13 shows pretreatment of AST (25 μM) in FA fibroblasts for 12 h followed by 12 h treatment with $H_2O_2$. Mitochondrial aconitase levels are unaffected by treatment of AST and $H_2O_2$. Immunoblot analysis was conducted utilizing enriched-mitochondrial pellets. Results are expressed as SEM with n≥3 for all concentrations;

FIG. 14A, FIG. 14B, FIG. 14C, and FIG. 14D show: FIG. 14A and FIG. 14B pretreatment of AST (25 and 50 μM) for 4 h followed by 24 h treatment with erastin (10 mM) immunoblots for indicated proteins of lysates derived from FA fibroblasts. FIG. 14C and FIG. 14D, relative abundance of TFR1 and FTH1 proteins normalized to β-actin loading control. Results are the means+SEM of n=3 for all concentrations. *$P<0.05$, **$P<0.005$, comparisons with the erastin group. Group comparisons are determined by a one-way analysis of variance (ANOVA) with Dunnet's correction post-hoc test using GraphPad Prism 8. Samples were run on the same gel for SDS-Page gel electrophoresis in nonconsecutive lanes;

FIG. 15 is a scheme of a proposed mechanism of intervention of RSSH donors. RSSH makes up for lack of FXN protein by providing sulfane sulfur source directly to ISCU2. (LIP=labile iron pool);

FIG. 16*a*, FIG. 16*b*, FIG. 16*c*, FIG. 16*d*, and FIG. 16*e* show general conditions: 4 h pre-treatment with RSSH donor or DRZ (25 mM if concentration not indicated) followed by 24 h incubation with DOX (5 mM if concentration not indicated). (FIG. 16*a*) Cell viability of H9c2 cardiac cells measured by CCK-8. (FIG. 16*b*) ROS emission in H9c2 cells measured by EPR spectroscopy. (FIG. 16*c*) Caspase activation in H9c2 cells measured by colorimetric assay. (FIG. 16*d*) Cell viability of MDA-MB-468 cells measured by MTT. And (FIG. 16*e*) Comparison of cell viabilities in DOX-challenged H9c2, MDA-MB-468, MCF-7, and HepG2 cells. Results are expressed as the mean±SEM (n=5 for each treatment group) with at least three independent experiments. *$P<0.05$, $P<0.01$, *$P<0.001$, ****$P<0.0001$ for comparisons with the DOX treatment group. Group comparisons are determined by a one-way analysis of variance (ANOVA) with Dunnett's correction post-hoc test using GraphPad Prism 9;

FIG. 17*a* and FIG. 17*b* show the general conditions for western blot analyses: 24 h pre-treatment with RSSH donor followed by 24 h incubation with DOX; and FIG. 18*a* and FIG. 18*b* are: (FIG. 18*a*) $H_2S$ sensitive probe Hsip-1 DA and (FIG. 18*b*) sulfane sulfur sensitive probe SSP4 fluorescence intensity per 1,000,000 cells following treatment with vehicle or DOX for 24 h.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides alkylsulfenyl thiocarbonates as a new class of RSSH precursors that efficiently release RSSH under physiologically relevant conditions. RSSH release kinetics from these precursors are tunable through electronic modification of the thiocarbonate carbonyl group's electrophilicity.

As used herein, the term "alkylsufenyl thiocarbonate" includes compounds of the general formula: $R^1S—SC(CO)OR^2$.

In some embodiments, the presently disclosed subject matter provides a compound of formula (I):

(I)

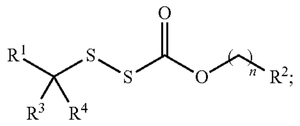

wherein: n is 0 or 1;

$R^1$ is

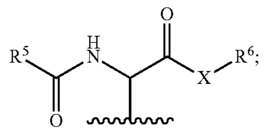

wherein $R^5$ and $R^6$ are each independently $C_1$-$C_4$ substituted or unsubstituted alkyl and substituted or unsubstituted aryl; X is O or NH; $R^2$ is substituted or unsubstituted aryl; $R^3$ and $R^4$ are each independently H or $C_1$-$C_4$ substituted or unsubstituted alkyl; and pharmaceutically acceptable salts thereof.

As used herein, the term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_{1-10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, cyano, and mercapto.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below.

In certain embodiments, the $C_1$-$C_4$ alkyl includes $C_1$, $C_2$, $C_3$, and $C_4$ alkyl, such as methyl, ethyl, n-propyl, isopropyl ($(CH_3)_2CH—$), n-butyl, iso-butyl ($(CH_3)_2—CH—CH_2—$), sec-butyl ($CH_3—CH_2—CH(CH_3)—$), and tert-butyl ($(CH_3)_3—C—$). In particular embodiments, the $C_1$-$C_4$ alkyl is methyl.

In certain embodiments, the compound of formula (I) is:

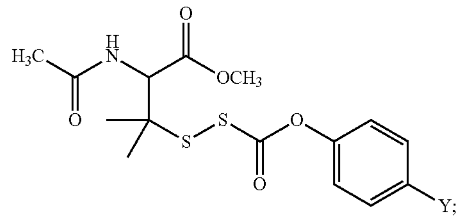

wherein Y is selected from the group consisting of H, $C_1$-$C_4$ alkyl, $C_1$-$C_4$ alkoxyl, NRR' where R and R' are each independently H or $C_1$-$C_4$ substituted or unsubstituted alkyl, $—CF_3$, halogen, and cyano.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The terms "halo," "halide," or "halogen" as used herein refer to fluoro, chloro, bromo, and iodo groups.

The term "cyano" refers to the —C≡N group.

In particular embodiments, the compound of formula (I) is selected from the group consisting of:

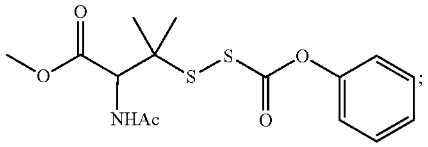

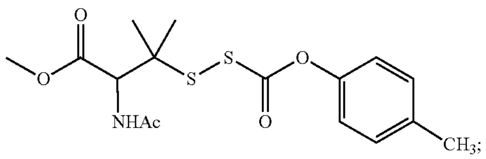

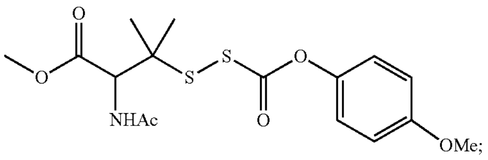

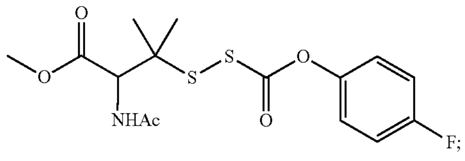

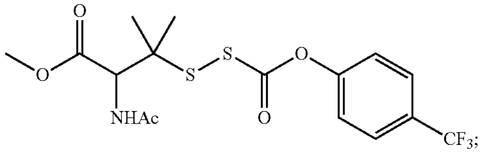
and

-continued

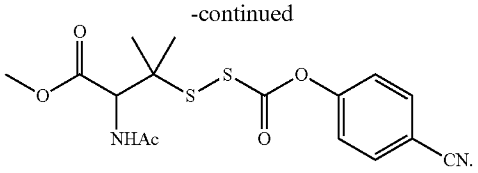

In other embodiments, the compound of formula (I) is:

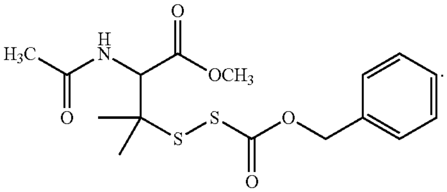 [SMILES: COC(=O)C(NC(C)=O)C(C)(C)SSC(=O)OCc1ccccc1]

In some embodiments, the presently disclosed subject matter provides a pharmaceutical composition comprising a compound of formula (I) and a pharmaceutically acceptable carrier.

The presently disclosed subject matter further provides kits comprising one or more compounds of formula (I) as described herein. The kits may employ any of the compounds disclosed herein and instructions for use. The compound may be formulated in any acceptable form. The kits may be used for any one or more of the uses described herein, and, accordingly, may contain instructions for any one or more of the stated uses (e.g., treating and/or preventing and/or delaying the onset and/or ischemia/reperfusion injury).

Kits generally comprise suitable packaging. The kits may comprise one or more containers comprising any compound described herein. Each component (if there is more than one component) can be packaged in separate containers or some components can be combined in one container where cross-reactivity and shelf-life permit.

The kits may optionally include a set of instructions, generally written instructions, although electronic storage media (e.g., magnetic diskette or optical disk) containing instructions also are acceptable, relating to the use of component(s) of the methods of the presently disclosed subject matter (e.g., treating, preventing and/or delaying the onset and/or the development of heart disease or ischemia/reperfusion injury). The instructions included with the kit generally include information as to the components and their administration to a subject.

B. Method for Treating a Disorder, Disease, or Condition Associated with Oxidative Stress, Including Ischemia/Reperfusion Injury In some embodiments, the presently disclosed subject matter provides a method for treating a disorder, disease, or condition associated with oxidative stress in a subject in need of treatment thereof, the method comprising administering to the subject a therapeutically effective amount of a compound of formula (I) or a pharmaceutical composition thereof.

Generally, oxidative stress is an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

Several disorders, diseases, and conditions are associate with oxidative stress including, but not limited to, a mitochondrial disorder; an inherited mitochondrial disease; Alpers Disease; Barth syndrome; a Beta-oxidation Defect; Carnitine-Acyl-Carnitine Deficiency; Carnitine Deficiency; a Creatine Deficiency Syndrome; Co-Enzyme Q10 Deficiency; Complex I Deficiency; Complex II Deficiency; Complex III Deficiency; Complex IV Deficiency; Complex V Deficiency; COX Deficiency; chronic progressive external ophthalmoplegia (CPEO); CPT I Deficiency; CPT II Deficiency; Friedreich's Ataxia (FA); Glutaric Aciduria Type II; Kearns-Sayre Syndrome (KSS); Lactic Acidosis; Long-Chain Acyl-CoA Dehydrogenase Deficiency (LCAD); LCHAD; Leigh Syndrome; Leigh-like Syndrome; Leber's Hereditary Optic Neuropathy (LHON); Lethal Infantile Cardiomyopathy (LIC); Luft Disease; Multiple Acyl-CoA Dehydrogenase Deficiency (MAD); Medium-Chain Acyl-CoA Dehydrogenase Deficiency (MCAD); Mitochondrial Myopathy, Encephalopathy, Lactacidosis, Stroke (MELAS); Myoclonic Epilepsy with Ragged Red Fibers (MERRF); Mitochondrial Recessive Ataxia Syndrome (MIRAS); Mitochondrial Cytopathy, Mitochondrial DNA Depletion; Mitochondrial Encephalopathy; Mitochondrial Myopathy; Myoneurogastrointestinal Disorder and Encephalopathy (MNGIE); Neuropathy, Ataxia, and Retinitis Pigmentosa (NARP); Pearson Syndrome; Pyruvate Carboxylase Deficiency; Pyruvate Dehydrogenase Deficiency; a POLG Mutation; a Respiratory Chain Disorder; Short-Chain Acyl-CoA Dehydrogenase Deficiency (SCAD); SCHAD; Very Long-Chain Acyl-CoA Dehydrogenase Deficiency (VLCAD); a myopathy; cardiomyopathy; encephalomyopathy; Parkinson's disease; amyotrophic lateral sclerosis (ALS); a motor neuron disease; epilepsy; macular degeneration; metabolic syndrome; brain cancer; Huntington's Disease; a mood disorder; schizophrenia; bipolar disorder; a pervasive developmental disorder; autistic disorder; Asperger's syndrome; childhood disintegrative disorder (CDD); Rett's disorder; PDD—not otherwise specified (PDD-NOS); a cerebrovascular accident; stroke; a vision impairment; optic neuropathy; dominant inherited juvenile optic atrophy; optic neuropathy caused by a toxic agent; glaucoma; Stargardt's macular dystrophy; diabetic retinopathy; diabetic maculopathy; retinopathy of prematurity; ischemic reperfusion-related retinal injury; oxygen poisoning; a haemoglobinopathy; thalassemia; sickle cell anemia; seizures; ischemia; renal tubular acidosis; attention deficit/hyperactivity disorder (ADHD); a neurodegenerative disorder resulting in hearing or balance impairment; Dominant Optic Atrophy (DOA); Maternally inherited diabetes and deafness (MIDD); chronic fatigue; contrast-induced kidney damage; contrast-induced retinopathy damage; Abetalipoproteinemia; retinitis pigmentosum; Wolfram's disease; Tourette syndrome; cobalamin c defect; methylmalonic aciduria; glioblastoma; Down's syndrome; acute tubular necrosis; a muscular dystrophy; a leukodystrophy; Progressive Supranuclear Palsy; spinal muscular atrophy; hearing loss; noise induced hearing loss; traumatic brain injury; Juvenile Huntington's Disease; Multiple Sclerosis; NGLY1; Multisystem atrophy; Adrenoleukodystrophy; and Adrenomyeloneuropathy.

In particular embodiments, the disorder, disease, or condition associated with oxidative stress comprises ischemia/reperfusion injury. Accordingly, in some embodiments, the presently disclosed compounds of formula (I) are cardioprotective, for example, against ischemia/reperfusion injury, including myocardial ischemia/reperfusion injury. In certain embodiments, the treating comprises preventing, reducing the occurrence of or severity of, or protecting against ischemia/reperfusion injury.

Ischemia is a condition characterized by an interruption or inadequate supply of blood to a cell, tissue, or organ, which causes oxygen deprivation in the affected cell, tissue, or organ. Accordingly, as used herein the term "ischemic injury," or derivations thereof, refers to an injury to a cell, tissue, and/or organ caused by ischemia, i.e., a reduction or insufficient supply of blood (and therefore oxygen) to a cell, tissue, and/or organ, e.g., due to a blocked artery and the like, resulting in damage or dysfunction of the cell, tissue, and/or organ.

Representative ischemic injuries include, but are not limited to, injuries caused by cardiovascular ischemia, cerebrovascular ischemia, renal ischemia, hepatic ischemia, ischemic cardiomyopathy, cutaneous ischemia, bowel ischemia, intestinal ischemia, gastric ischemia, pulmonary ischemia, pancreatic ischemia, skeletal muscle ischemia, abdominal muscle ischemia, limb ischemia, ischemic colitis, mesenteric ischemia, and silent ischemia. An ischemic injury can affect, for example, a heart, kidney, liver, brain, muscle, intestine, stomach, lung, and/or skin.

In a particular embodiment, the ischemic injury is the result of a myocardial ischemia. Myocardial ischemia is a condition caused by a blockage or constriction of one or more of the coronary arteries, such as can occur with atherosclerotic plaque occlusion or rupture. The blockade or constriction causes oxygen deprivation of the non-perfused tissue, which can cause tissue damage. An injury resulting from a myocardial ischemia can result from, for example, a myocardial infarction (e.g., an acute myocardial infarction) in a subject. In another embodiment, the ischemic injury is an injury resulting from cerebral ischemia (e.g., a stroke) in a subject.

Upon reperfusion with subsequent reoxygenation of the cell, tissue, or organ, i.e., when blood is able to flow again or the oxygen demand of the cell, tissue, or organ subsides, additional injury can be caused by oxidative stress. As used herein, the term "ischemia-reperfusion injury" refers to an injury resulting from the restoration of blood flow to an area of a cell, tissue, and/or organ that had previously experienced deficient blood flow due to an ischemic event. Oxidative stresses associated with reperfusion may cause damage to the affected cells, tissues, and/or organs. Ischemia-reperfusion injury is characterized biochemically by a depletion of oxygen during an ischemic event followed by reoxygenation and the concomitant generation of reactive oxygen species during reperfusion.

An ischemia-reperfusion injury can be caused, for example, by a natural event (e.g., restoration of blood flow following a myocardial infarction), a trauma, or by one or more surgical procedures or other therapeutic interventions that restore blood flow to a cell, tissue, and/or organ that has been subjected to a diminished supply of blood. Such surgical procedures include, for example, coronary artery bypass graft surgery, coronary angioplasty, organ transplant surgery and the like. The effects of ischemia/reperfusion injury can be fatal, particularly when the injury occurs in a critical organ, such as the heart or brain.

Accordingly, in some embodiments, the presently disclosed subject matter provides a method for treating, preventing, reducing, or protecting against ischemia/reperfusion injury in a subject who is afflicted with or is at risk of an ischemia/reperfusion injury or an ischemic event. Thus, provided herein is a method of treating, preventing, reducing, or protecting against injury associated with ischemia/reperfusion by administering to a subject in need of treatment thereof, a therapeutically effective amount of at least one compound of formula (I).

In some embodiments, a compound of formula (I) is administered to the subject prior to the onset of ischemia. Presently disclosed compounds of formula (I) can thus be used in methods of preventing or reducing injury associated with future ischemia/reperfusion. For example, administration of a compound of formula (I) prior to the onset of ischemia may reduce tissue necrosis (the size of infarct) in at-risk tissues.

In some embodiments, a compound of formula (I) is administered to the subject after ischemia. In some embodiments, a compound of formula (I) is administered to the subject after ischemia, but before reperfusion. In other embodiments, a compound of formula (I) is administered to the subject after ischemia/reperfusion, where the administration protects against further injury. In some embodiments, a compound of formula (I) is administered to a subject thought to be or is demonstrated to be at risk for an ischemic event. In some embodiments, a compound of formula (I) is administered to or contacted with an organ that is to be transplanted in an amount effective to reduce ischemia/reperfusion injury to the organ upon reperfusion in the recipient of the transplanted organ.

For the treatment of ischemic and ischemia-reperfusion injuries caused by therapeutic interventions, such as surgical procedures, it is preferable that a compound of formula (I) be administered to a subject undergoing treatment prior to the therapeutic intervention (e.g., cardiac surgery, organ transplant). For example, a compound of formula (I) can be administered to a subject undergoing treatment, e.g., about 5 minutes, about 10 minutes, about 15 minutes, about 20 minutes, about 30 minutes or about 45 minutes, about 1 hour, about 2 hours, about 3 hours, about 4 hours, about 5 hours, about 12 hours, about 24 hours, or about 48 hours prior to the therapeutic intervention.

Alternatively, or in addition, a compound of formula (I) can be administered to a subject undergoing treatment at the time of, or during, the therapeutic intervention. For example, the compound can be administered one or more times during the course of a therapeutic intervention in intervals (e.g., 15-minute intervals). Alternatively, a compound of formula (I) can be administered continuously throughout the duration of a therapeutic intervention.

Furthermore, a compound of formula (I) can be administered to a subject undergoing treatment after a therapeutic intervention. For example, a compound of formula (I) can be administered to a subject undergoing treatment, e.g., about 5 minutes, about 10 minutes, about 15 minutes, about 20 minutes, about 30 minutes or about 45 minutes, about 1 hour, about 2 hours, about 3 hours, about 4 hours, about 5 hours, about 12 hours, about 24 hours, or about 48 hours after the therapeutic intervention.

A compound of formula (I) also can be used to prevent, inhibit, or reduce the occurrence of an ischemia or ischemia-reperfusion injury to a cell, tissue, and/or organ, ex vivo, prior to a therapeutic intervention (e.g., a tissue employed in a graft procedure, an organ employed in an organ transplant surgery). For example, prior to transplant of an organ into a host individual (e.g., during storage or transport of the organ in a sterile environment), the organ can be contacted with a compound of formula (I) to prevent, inhibit, or reduce the occurrence of an ischemia or ischemia-reperfusion injury.

As described herein, conditions resulting from ischemia, and injuries caused by ischemia or ischemia-reperfusion, can induce apoptotic cell death in an affected cell, tissue, and/or organ, leading to damage and dysfunction. Accordingly, the compounds of the invention also have utility in methods of inhibiting apoptosis in a cell, a tissue, and/or an organ (e.g., a transplant tissue or organ or a cell, tissue, or organ in a subject), wherein the cell, tissue or organ has experienced an ischemia or other condition or disorder that results in excessive or unwanted apoptosis. The methods comprise contacting the cells, tissue, and/or organ with, or administering to the subject, an effective amount of a compound of formula (I).

Subjects can be selected for treatment who are at risk of a first or subsequent ischemic event. For example, such subjects include, but are not limited to, those with known hypercholesterolemia, EKG changes associated with risk of ischemia, sedentary lifestyle, angiographic evidence of partial coronary artery obstruction, echocardiographic evidence of myocardial damage, or any other evidence of a risk for a future or additional ischemic event (for example a myocardial ischemic event, such as a myocardial infarction (MI), or a neurovascular ischemia, such as a cerebrovascular accident (CVA)). In some embodiments, subjects are selected for treatment who are at risk of future ischemia, but who have no present evidence of ischemia, such as electrocardiogramges associated with ischemia (for example, peaked or inverted T-waves or ST segment elevations or depression in an appropriate clinical context), elevated CKMB, or clinical evidence of ischemia, including crushing substernal chest pain or arm pain, shortness of breath and/or diaphoresis.

Compounds of formula (I) also can be administered prior to procedures in which myocardial ischemia is at risk of occurring, for example an angioplasty or other surgeries, such as coronary artery bypass graft surgery. In other embodiments, a compound of formula (I) can be administered to a subject at demonstrated risk for an ischemic event. The selection of a subject with such a status can be performed by a variety of methods, some of which are noted hereinabove. For example, a subject with one of more of an abnormal EKG not associated with active ischemia, prior history of myocardial infarction, elevated serum cholesterol, and the like, would be at risk for an ischemic event. Thus, an at-risk subject could be selected by physical testing or eliciting the potential subject's medical history to determine whether the subject has any indications of risk for an ischemic event. If risk is demonstrated based on the indications discussed above, or any other indications that one skilled in the art would appreciate, then the subject would be considered at demonstrated risk for an ischemic event.

Ischemia/reperfusion may damage tissues other than those of the myocardium and the presently disclosed subject matter includes methods for treating or preventing such damage. In one variation, the method finds use in reducing injury from ischemia/reperfusion in the tissue of the brain, liver, gut, kidney, bowel, or in any other tissue.

Selecting a person at risk for non-myocardial ischemia could include a determination of the indicators used to assess risk for myocardial ischemia. Other factors, however, may indicate a risk for ischemia/reperfusion in other tissues. For example, surgery patients often experience surgery-related ischemia. Thus, subjects scheduled for surgery could be considered at risk for an ischemic event. The following risk factors for stroke (or a subset of these risk factors) would demonstrate a subject's risk for ischemia of brain tissue: hypertension, cigarette smoking, carotid artery stenosis, physical inactivity, diabetes mellitus, hyperlipidemia, transient ischemic attack, atrial fibrillation, coronary artery disease, congestive heart failure, past myocardial infarction, left ventricular dysfunction with mural thrombus, and mitral stenosis. Further, complications of untreated infectious diarrhea in the elderly can include myocardial, renal, cerebrovascular, and intestinal ischemia. Alternatively, subjects could be selected based on risk factors for ischemic bowel, kidney, or liver disease. For example, treatment would be initiated in elderly subjects at risk of hypotensive episodes, such as surgical blood loss. Thus, subjects presenting with such an indication would be considered at risk for an ischemic event. Also included is a method of administering a compound of formula (I) to a subject who has any one or more of the conditions listed herein, such as diabetes mellitus or hypertension. Other conditions that may result in ischemia, such as cerebral arteriovenous malformation would be considered to demonstrate risk for an ischemic event.

The method of administering a compound of formula (I) to an organ to be transplanted includes administration of a compound of formula (I) prior to removal of the organ from the donor, for example through the perfusion cannulas used in the organ removal process. If the organ donor is a live donor, for example a kidney donor, the compound of formula (I) can be administered to the organ donor as described above for a subject at risk for an ischemic event. In other cases, the compound of formula (I) can be administered by storing the organ in a solution comprising compound of formula (I). For example, the compound of formula (I) can be included in the organ preservation solution, such as University of Wisconsin "UW" solution, which is a solution comprising hydroxyethyl starch substantially free of ethylene glycol, ethylene chlorohydrin, and acetone (see U.S. Pat. No. 4,798,824). Where an organ or tissue is accessible because of removal from the patient, such organ or tissue may be bathed in a medium containing the subject compositions, the subject compositions may be painted onto the organ, or may be applied in any convenient way. The methods of the presently disclosed subject matter embrace administration of the compounds to an organ to be donated (such as to prevent ischemia/reperfusion injury). Accordingly, organs that are removed from one subject for transplant into another subject may be bathed in a medium containing or otherwise exposed to a compound or composition as described herein.

C. Method for Treating a Disorder, Disease, or Condition Associated with Impaired Fe—S Cluster Biosynthesis In other embodiments, the presently disclosed subject matter provides a method for treating a disorder, disease, or condition associated with impaired Fe—S cluster biosynthesis, the method comprising administering to a subject in need of treatment thereof, a therapeutically effective amount of a compound of formula (I). In certain embodiments, the disorder, disease, or condition associated with impaired Fe—S cluster biosynthesis is selected from Friedreich's Ataxia, sideroblastic anemia, and myopathy, including myopathy with severe exercise intolerance. See Rouault and Tong, 2008. In particular embodiments, the disorder, disease, or condition associated with impaired Fe—S cluster biosynthesis comprises Friedreich's Ataxia.

D. Methods for Treating Anthracycline-Induced Cardiotoxicity

In other embodiments, the presently disclosed subject matter provides a method for treating anthracycline-induced cardiotoxicity in a subject in need of treatment thereof, the method comprising administering to the subject a therapeutically effective amount of a compound of formula (I). In certain embodiments, the subject is being treated with, has been treated with, or is expected to being treating with one or more anthracyclines. In more certain embodiments, the subject is administered a compound of formula (I) before beginning treatment with an anthracycline, during treatment with an anthracycline, or after treatment with an anthracycline. In particular embodiments, the one or more anthracyclines are selected from daunorubicin, doxorubicin, epirubicin, idarubicin, mitoxantrone, valrubicin, and combinations thereof.

In certain embodiments, the subject is being treated for cancer. In more certain embodiments, the cancer is selected from acute lymphocytic leukemia, acute myelogenous leukemia, Hodgkin's lymphoma, non-Hodgkin's lymphoma, bladder cancer, breast cancer, metastatic breast cancer, ovarian cancer, osteogenic sarcoma, Ewing sarcoma, soft tissue sarcoma, thyroid cancer, neuroblastoma, Wilm's tumor, small cell lung cancer, advanced endometrial carcinoma, metastatic hepatocellular cancer, multiple myeloma, advanced renal cell carcinoma, thymomas and thymic malignancies, uterine sarcoma, and Waldenstrom macroglobulinemia.

In certain embodiments, the subject is afflicted with or at risk of developing cardiomyopathy and/or heart failure.

E. Methods for Treating COVID-19

In other embodiments, the presently disclosed subject matter provides a method for treating COVID-19, the method comprising administering to a subject in need of treatment thereof a therapeutically effective amount of a compound of formula (I).

As used herein, the term "treating" can include reversing, alleviating, inhibiting the progression of, preventing or reducing the likelihood of the disease, disorder, or condition to which such term applies, or one or more symptoms or manifestations of such disease, disorder, or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In some embodiments, the subject is human. In other embodiments, the subject is non-human.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In other embodiments, the presently disclosed subject matter included administering a compound of formula (I) in combination with one or more therapeutic agents. In certain embodiments, the presently disclosed method of treatment further comprises administering to the subject one or more compounds of formula (I) in combination with one or more other therapeutic agents designed to minimize or mitigate ischemic injury. In particular embodiments, the one or more other therapeutic agents is selected from the group consisting of an angiotensin I-converting enzyme (ACE) inhibitor, an alpha-adrenergic blocker, a central adrenergic inhibitor, a beta-adrenergic blocker, an angiotensin II receptor blocker, a calcium channel blocker, a vasodilator, a phosphodiesterase (PDE) inhibitor, an HMG-CoA reductase inhibitor, a cholesterol-lowering agent, an antiarrhythmic agent, a digitalis drug, a nitrate, a diuretic, an anticoagulant, an antiplatelet agent, a thrombolytic agent, an antioxidant, and combinations thereof, including other agents or medical interventions for protecting the myocardium in subject afflicted with coronary artery disease.

The term "combination" is used in its broadest sense and means that a subject is administered at least two agents, more particularly a compound of formula (I) and at least one more other therapeutic agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the compounds of formula (I) described herein can be administered alone or in combination with adjuvants that enhance stability of the compounds of formula (I), alone or in combination with one or more therapeutic agents, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of a compound of formula (I) and at least one additional therapeutic agent can be varied so long as the beneficial effects of the combination of these agents are achieved. Accordingly, the phrase "in combination with" refers to the administration of a compound of formula (I) and at least one additional therapeutic agent either simultaneously, sequentially, or a combination thereof. Therefore, a subject administered a combination of a compound of formula (I) and at least one additional therapeutic agent can receive compound of formula (I) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of formula (I) and at least one additional therapeutic agent are administered simultaneously, they can be administered to the subject as separate pharmaceutical compositions, each comprising either a compound of formula (I) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of formula (I) and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index } (SI)$$

wherein:

- $Q_A$ is the concentration of a component A, acting alone, which produced an end point in relation to component A;
- $Q_a$ is the concentration of component A, in a mixture, which produced an end point;
- $Q_B$ is the concentration of a component B, acting alone, which produced an end point in relation to component B; and
- $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

As used herein, the term "inhibit," and grammatical derivations thereof, refers to the ability of a presently disclosed compound, e.g., a presently disclosed compound of formula (I), to block, partially block, interfere, decrease, or reduce the growth of bacteria or a bacterial infection. Thus, one of ordinary skill in the art would appreciate that the term "inhibit" encompasses a complete and/or partial decrease in the growth of bacteria or a bacterial infection, e.g., a decrease by at least 10%, in some embodiments, a decrease by at least 20%, 30%, 50%, 75%, 95%, 98%, and up to and including 100%.

C. Pharmaceutical Compositions and Administration

In another aspect, the present disclosure provides a pharmaceutical composition including one compound of formula (I) alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions, and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount, or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Alkylsulfenyl Thiocarbonates: Precursors to Hydropersulfides Potently Attenuate Oxidative Stress

1.1 Overview

The recent discovery of the prevalence of hydropersulfides (RSSH) species in biological systems suggests their potential roles in cell regulatory processes. The reactive and transient nature of RSSH, however, makes their study difficult, and dependent on the use of donor molecules.

The presently disclosed subject matter provides alkylsulfenyl thiocarbonates as a new class of RSSH precursors that efficiently release RSSH under physiologically relevant conditions. RSSH release kinetics from these precursors are tunable through electronic modification of the thiocarbonate carbonyl group's electrophilicity. In addition, these precursors also react with thiols to release RSSH with a minor amount of carbonyl sulfide (COS). Importantly, RSSH generation by these precursors protects against oxidative stress in H9c2 cardiac myoblasts. Furthermore, the ability of these precursors to increase intracellular RSSH levels is demonstrated.

1.2 Introduction

Alkylsulfenyl thiocarbonates (RSSC(O)OR) are an interesting class of sulfur compounds that have received relatively limited attention. In the presence of thiols, these compounds produce carbonyl sulfide (COS) likely via thiol attack at the internal sulfur atom of the disulfide to produce an unsymmetrical disulfide and a thiocarbonate intermediate, which spontaneously decomposes to release COS (Scheme 1-1a). Brois et al., 1970; Zhao et al., 2019. In the presence of a strong base like potassium tert-butoxide, RSSC(O)OR can react to form dialkyl trisulfides, presumably via the intermediacy of RSSH (Scheme 1-1b). Harpp and Granata, 1976; Harpp and Granata, 1979. To the best of our knowledge, however, hydrolysis of these compounds under physiologically relevant conditions to release RSSH has not been reported. Without wishing to be bound to any one particular theory, it is thought that enhancing the electrophilicity of the thiocarbonate carbonyl carbon in compound 1 by varying the electronic properties of the $R^2$ group would promote hydrolysis under physiological conditions (Scheme 1-1c). Additionally, modification of the $R^2$ group in compound 1 should allow the rate of hydrolysis to be tuned, thereby varying the RSSH release kinetics. It also was thought that increasing the steric hindrance at the inner sulfur atom of the precursor would be important to minimize its reaction with thiol, which precludes RSSH generation. Notably, sterically hindered RSSH also are expected to be superior substrates for trans-persulfidation reactions due to the preference of nucleophilic attack of thiols on the terminal sulfur atom.

Scheme 1-1. RSSH and COS Generation from Alkylsulfenyl Thiocarbonates.

a) Thiol-mediated COS release from alkylsulfenyl thiocarbonates $$RSSCO_2R + R'SH \longrightarrow RS{-}SR' + {}^{-}SCO_2R$$

$${}^{-}SCO_2R \longrightarrow COS + ROH$$

b) Base-medaited dialkyltrisulfide generation fom alkylsulfenyl thiocarbonates $$RSSCO_2R + R'O^{-} \longrightarrow R{-}S{-}S^{-} + R'OCO_2R$$

$$R{-}S{-}S^{-} + RSSCO_2R \longrightarrow R{-}S{-}S{-}S{-}R + {}^{-}SCO_2R$$

c) This work

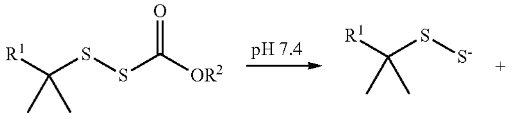

1

$CO_2$ + $R^2OH$

1.3 Results and Discussion

1.3.1 Synthesis of Alkylsulfenyl Thiocarbonates

To test this hypothesis, precursors 1a-f were synthesized via treatment of N-acetyl-penicillamine methyl ester (2) with chlorocarbonylsulfenyl chloride to obtain intermediate 3, which was then immediately treated with various para-substituted phenols 4a-f (Scheme 1-2; see Section 1.5 for synthetic and analytical details).

Scheme 1-2. Synthesis of Alkylsulfenyl Thiocarbonates 1a-f with Overall Yields.

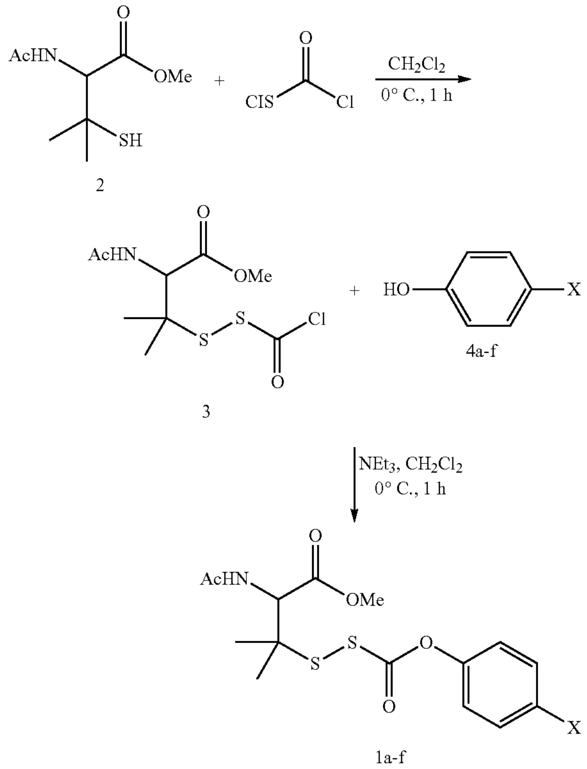

2

3

4a-f 1a-f

X = H, 1a, 64%
= $CH_3$, 1b, 84%
= OMe, 1c, 86%
= F, 1d, 65%
= $CF_3$, 1e, 84%
= CN, 1f, 75%

1.3.2 RSSH Generation Studies

With these precursors in hand, RSSH generation from 1a was examined by trapping with β-(4-hydroxyphenyl)ethyl iodoacetamide (HPE-IAM) under physiological conditions. UPLC-MS analysis following incubation of 1a with 10 equiv of HPE-IAM in pH 7.4 ammonium bicarbonate buffer shows RSS-HPE-AM 5 formation (Scheme 1-3, eq. 1, and FIG. 1*a*), confirming RSSH generation. A small amount of dialkyl trisulfide 6 formation also is observed (FIG. 1*a*), suggesting that precursor 1a is a competitive trap for the initially released RSSH (Scheme 1-3, eq. 2). To minimize the reaction of released RSSH with precursor 1a, RSSH generation in the presence of the more electrophilic trap, S-methyl methanethiosulfonate (MMTS) was examined. MMTS has been reported as an alkylating reagent for identification of small molecule and protein hydropersulfides. Zheng et al., 2017; Pan and Carroll, 2013. Incubation of 1a with 10 equiv of MMTS shows RSS-S-Me 7 formation with no evidence of dialkyl trisulfide 6 (FIG. 1*b*), supporting that MMTS is a more efficient trap than HPE-IAM.

Scheme 1-3. RSSH Generation from Precursor 1a (1)

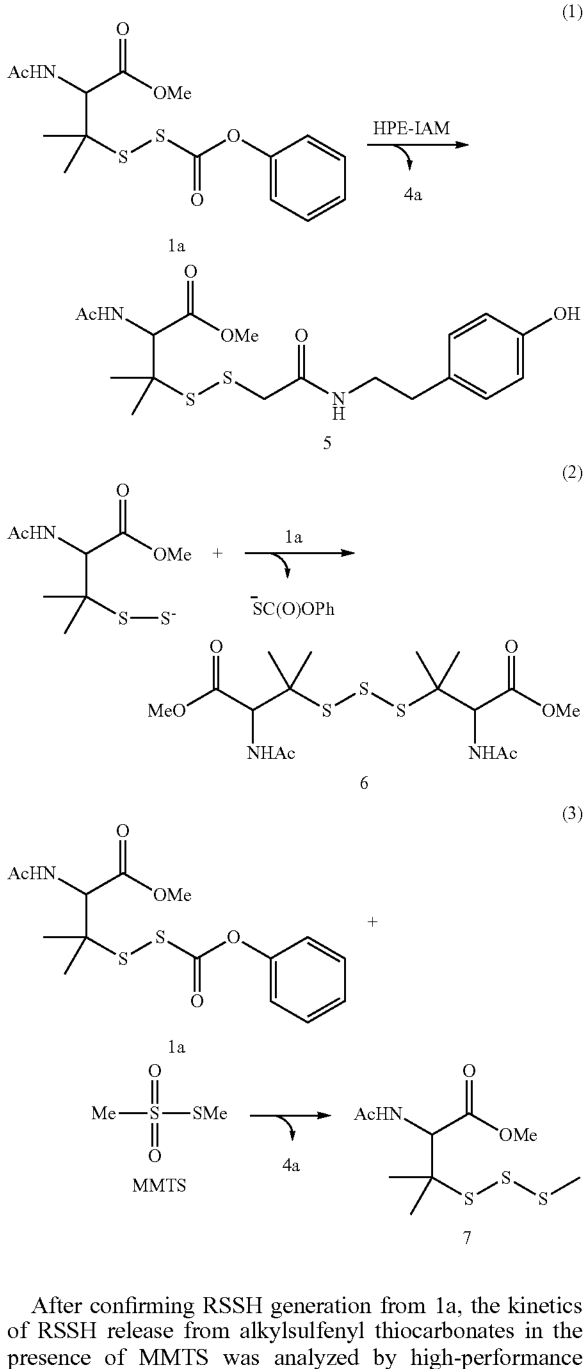

1a

5

(2)

6

(3)

1a

MMTS

7

After confirming RSSH generation from 1a, the kinetics of RSSH release from alkylsulfenyl thiocarbonates in the presence of MMTS was analyzed by high-performance liquid chromatography (HPLC). Due to the lack of a chromophore in MMTS adduct 7, the decay of the RSSH precursor and formation of the corresponding phenol byproduct was monitored. First-order rate constants were obtained by plotting the precursor decay and phenol byproduct formation as a function of time. HPLC analysis of 1a incubation with 10 equiv of MMTS in phosphate buffered saline (PBS, pH 7.4, 100 mM) shows disappearance of 1a ($k=5.39\times10^{-3}$ $min^{-1}$; $t_{1/2}$=129±2 min) with concomitant formation of phenol ($k=5.33\times10^{-3}$ $min^{-1}$; $t_{1/2}$=130±1 min)

Figure 2:
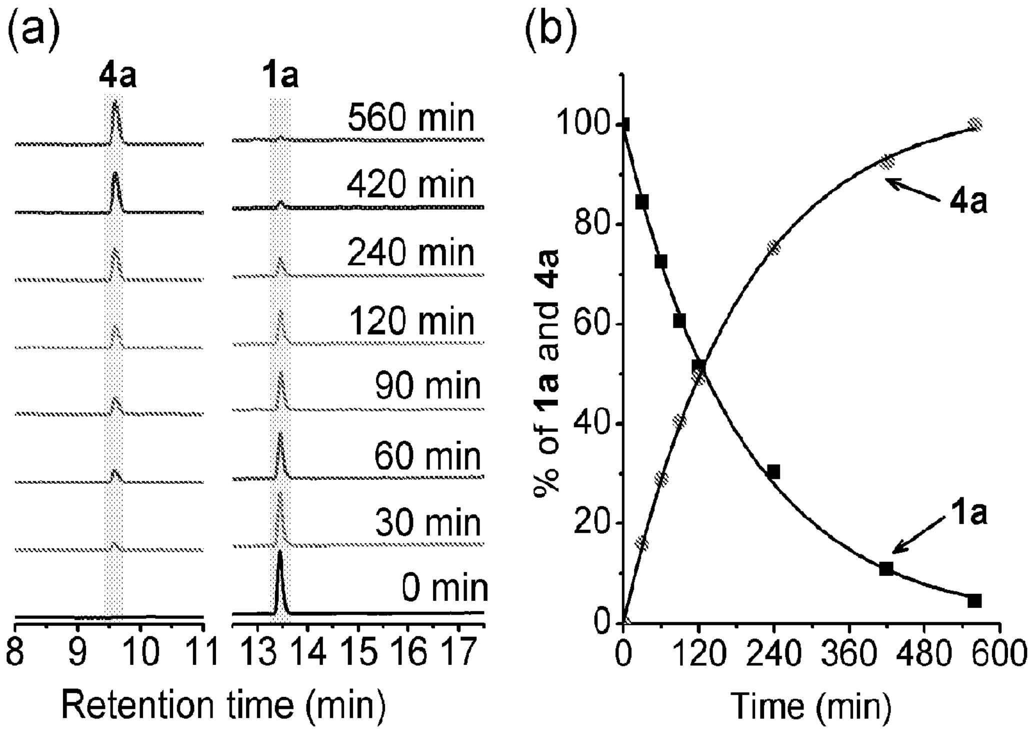

(FIG. 2). The observation of similar rate constants for both 1a decay and phenol (4a) formation indicates a rapid reaction of relased RSSH with MMTS, and that these observed rate constants indicate the RSSH release rate. Importantly, 92% of the byproduct phenol 4a is observed. In addition, the effect of pH on the kinetics of RSSH release also was examined. As expected, the rate of 1a hydrolysis is enhanced at pH 8.0 ($t_{1/2}$=37±3 min) and is slowed significantly at pH 6.0 ($t_{1/2}$=1599±48 min), supporting the proposed base catalyzed hydrolysis to release RSSH.

The RSSH release kinetics for precursors containing a variety of para-substituted phenols were then compared. It was hoped to decrease the rate of RSSH release through the introduction of electron-donating groups. Indeed, a small decrease in the RSSH release rate from 1b, equipped with a 4-Me substituent (137±4 min) (Table 1) was observed. Similarly, precursor 1c, equipped with a 4-OMe substituent, shows a half-life 147±2 min, suggesting a minor effect of electron donating groups on RSSH release rate. It also was found that electron withdrawing groups enhance the rate of RSSH release. For example, 4-F substituted precursor 1d releases RSSH with a half-life of 96±3 min. Similarly, 4-$CF_3$ substituted precursor 1e, and 4-CN substituted precursor 1f generate RSSH with a half-life of 56±3 min and 28±1 min, respectively. Importantly, UPLC-MS analysis of 1a-f following incubation with MMTS shows adduct 7 formation as the exclusive product (FIGS. 11-15†), and HPLC analysis confirms phenol by-product 4a-f formation in excellent yields (Table 1). Taken together, these results indicate that the RSSH release kinetics of alkylsulfenyl thiocarbonates can be tuned through electronic modulation of the thiocarbonate carbonyl carbon in precursor 1.

TABLE 1

Half-lives for Precursors 1a-f and Phenol 4a-f Yields

| Precursor | X | $t_{1/2}$ (min)[a] | ArOH | 4a-f yield (%) |
|---|---|---|---|---|
| 1a | 4-H | 129 ± 2 | 4a | 92 ± 2 |
| 1b | 4-$CH_3$ | 137 ± 4 | 4b | 93 ± 4 |
| 1c | 4-OMe | 147 ± 2 | 4c | 92 ± 1 |
| 1d | 4-F | 96 ± 3 | 4d | 96 ± 6 |
| 1e | 4-$CF_3$ | 56 ± 3[b] | 4e | 97 ± 1 |
| 1f | 4-CN | 28 ± 1 | 4f | 97 ± 2 |

[a]RSSH precursors (100 μM) were incubated in the presence of MMTS (1 mM) in pH 7.4 PBS containing DTPA at 37° C.
[b]Reduced aqueous solubility required this experiment to be carried out in PBS with 50% acetonitrile. Reported data represent averages ± SD (n = 3).

To further explore the substrate scope, O-benzyl substituted RSSH precursor 8 was synthesized (Scheme 1-4). Significantly slower RSSH release ($t_{1/2}$=2235±94 min) was observed, indicating slow hydrolysis which is likely due to reduced electrophilicity of the thiocarbonate carbonyl carbon (O-benzyl substituent in 8 vs. O-phenyl in precursors 1a-f).

Scheme 1-4 RSSH generation from O-benzyl substituted RSSH precursor 8

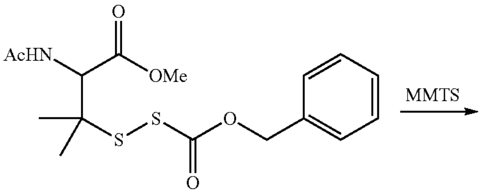

8

-continued

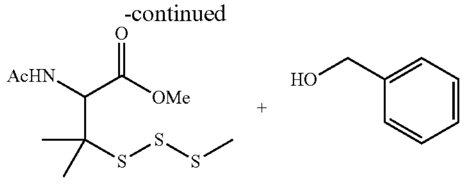

7

1.3.3 RSSH Generation in the Presence of Thiol

Next, the ability of alkylsulfenyl thiocarbonate 1a to release RSSH in the presence of thiols was examined. It was thought that if thiol attacks at the carbonyl carbon of the thiocarbonate moiety, RSSH and/or RSSH-derived polysulfides, along with S-alkyl-thiocarbonate 9a should be observed (Scheme 1-5, eq. 1). Alternatively, thiol can attack at the internal sulfur atom of the disulfide to produce unsymmetrical disulfide 10 and thiocarbonate intermediate 11a, which can rapidly decompose to release COS and phenol (Scheme 1-5, eqs. 2 and 4). If formed, COS will be hydrolyzed to $H_2S$ in biological systems by the ubiquitous enzyme carbonic anhydrase (CA). Chengelis and Neal, 1980.

Initially, the decomposition of 1a was analyzed in the presence of 5 equiv of N-acetylcysteine (NAC) in PBS (pH 7.4) by HPLC. Rapid decomposition of 1a is observed in the presence of NAC ($t_{1/2}$=0.64±0.11 min) (Table. 3), indicating a rapid reaction between NAC and 1a. To investigate the mechanism, this reaction was monitored by UPLC-MS. As shown in FIG. 3, disappearance of the peak attributed to 1a is observed with concomitant formation of symmetrical dialkyl polysulfides (cyan highlight, $R^1SS_nSR^1$, n=1-4), presumably formed by the decomposition of RSSH through disproportionation (Scheme 1-5, eqs. 5 and 6). Additionally, a small amount of unsymmetrical dialkyl polysulfide (pink highlight, $R^1SS_nSR^2$, n=0-3) is observed, likely formed via NAC reaction with symmetrical dialkyl polysulfides (Scheme 1-5, eq. 7). As expected, a new peak at 5.65 min corresponding to N-acetyl cysteine-thiocarbonate 9a also is observed, confirming thiol attack at the perthiocarbonate carbonyl carbon of 1a to release RSSH. Due to the unstable nature of RSSH under these experimental conditions, the yield of the by-product 9a was measured as an indication of RSSH yield. The observation of RSSH-derived polysulfides formation as major products led us to anticipate the efficient formation of by-product 9a. Incubation of 1a with 5 equiv of N-acetylcysteine methyl ester, however, shows only 53% formation of 9a. The lower observed yield of 9a is likely due to its further reaction with RSSH under these conditions. This hypothesis is supported by UPLC-MS data, where appearance of a new peak was observed at 5.2 min with m/z=427.0659 (FIG. 3). This peak is assigned to by-product 12, potentially formed by RSSH reaction with 9a as shown in Scheme 1-5, eq. 8. Furthermore, disappearance of 12 also is observed, likely due to further reaction with RSSH producing dialkyl trisulfide and COS (Scheme 1-5, eq. 9).

Scheme 1-5 Proposed Mechanism of RSSH and COS Generation from 1a in the Presence of Thiol.

(1)

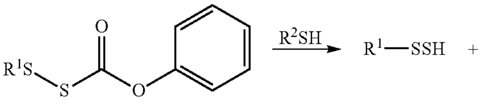

1a

-continued

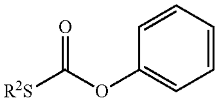

9a

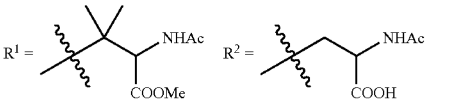

(2)

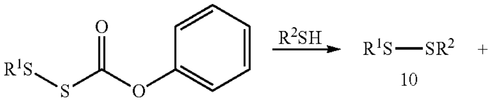

1a 10

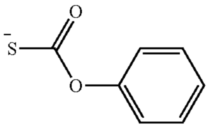

11a (3)

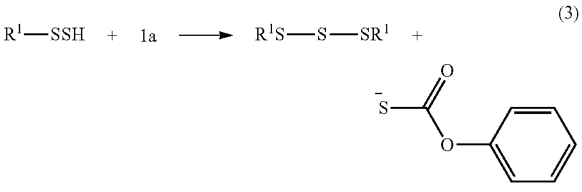

11a (4)

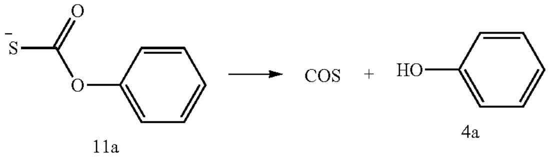

11a 4a (5)

$$2\,R^1SS^- \rightleftharpoons R^1S-(S)_n-SR^1 + H_2S$$

(6)

$$n\,R^1SS^- + R^1S-(S)_n-SR^1 \rightleftharpoons R^1S-(S)_{n+1}-SR^1 +$$

n $R^1$SH
2

(7)

$$n\,R^2SH + R^1S-(S)_n-SR^1 \rightleftharpoons R^1S-(S)_n-SR^2 +$$

n $R^1$SH
2

(8)

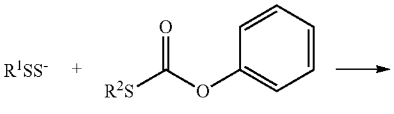

9a

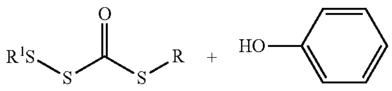

12 4a

-continued (9)

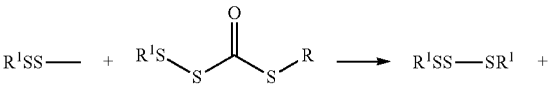

12

COS + RSH

COS generation from 1a was analyzed in the presence of NAC by membrane inlet mass-spectrometry (MIMS), a technique used for detection of dissolved hydrophobic gases in aqueous solutions. Hoch and Kok, 1963; Cline et al., 2011. For comparison, analogous experiments were conducted with the primary alkyl RSSH precursor 13 (Scheme 1-6). Thiol is expected to react with 13 selectively at the disulfide's internal sulfur atom producing unsymmetrical disulfide and thiocarbonate intermediate 9c, which subsequently decomposes to release COS (Scheme 1-6). Comparison of COS release from 1a in the presence of NAC shows only approximately 20% COS production with respect to that observed for precursor 13 (FIG. 4*a*). Under these conditions, the observed COS signal is likely a result of both NAC and initially released RSSH reaction with 1a to produce thiocarbonate intermediate 11a (Scheme 1-5, eqs. 2 and 3). Taken together, these results demonstrate that 1a predominantly produces RSSH, even in the presence of thiols. COS release from precursors 1b-f in the presence of NAC also was examined. As shown in FIG. 4*a*, similar COS generation is observed for all precursors indicating electron donating/withdrawing groups do not have a major effect on COS release rates. The reactivity of these precursors toward GSH also was measured. As expected, a slightly faster COS release is observed in the presence of GSH ($pK_a$=8.83) compared with NAC ($pK_a$=9.52) (FIG. 4*b*), presumably due to a higher concentration of the glutathione thiolate under these conditions.

Scheme 1-6. Proposed Mechanism of 13 Reaction with Thiol.

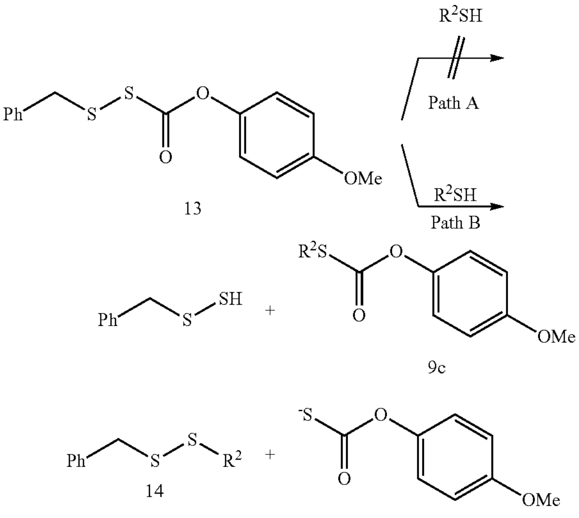

13 9c 14 9c

Reaction of O-benzyl substituted precursor 8 with NAC also was examined. As expected, a rapid decomposition of 8 is observed in the presence of thiol ($t_{1/2}$=4.0±0.7 min vs.

2235 min in the absence of NAC). With respect to 1a, 8 decomposes about six times slower in the presence of thiol. Similarly, slower COS generation is observed from precursor 8 in the presence of thiol compared to 1a (FIG. 7). Whether the reduced electrophilicity of the carbonyl carbon of precursor 8 favors thiol attack at the disulfide, which would preclude RSSH generation, also was examined. UPLC-MS analysis, however, shows $R^1SS_nSR^1$ (n=1-4) and $R^1SS_nSR^2$ (n=0-3) formation, indicating that 8 releases RSSH even in the presence of thiol. Thus, the results presented here confirm that alkylsulfenyl thiocarbonate thiolysis can be achieved under physiological conditions to release RSSH.

1.3.4 RSSH Protection Against Oxidative Stress

Oxidative stress has been implicated in the etiologies of many cardiovascular diseases. Dhalla et al., 2000; D'Oria et al., 2020. Oxidative stress usually arises from overproduction of reactive oxygen species (ROS). ROS constitutes both oxygen free radicals, such as superoxide, hydroxyl radicals, and peroxyl radicals, and non-radicals, such as hydrogen peroxide, and hypochlorous acid. It has been proposed that RSSH generation can be an endogenous cellular protectant in response to oxidative stress. Álvarez et al., 2017. Furthermore, it appears likely that the proposed mechanism of protection can be augmented pharmacologically with the addition of RSSH donor species.

To test this hypothesis, RSSH-mediated cellular protection against oxidative-stress was evaluated. First, the cytotoxicity of 1a on H9c2 cardiac myoblasts was examined using the Sytox viability assay, which measures cell membrane integrity. Jones and Singer, 2001. Both precursor 1a and its by-product phenol show no toxicity toward H9c2 cells up to 100 mM (FIG. 8). The cytoprotective effects of 1a was then measured against oxidative stress. As expected, treatment of H9c2 cells with hydrogen peroxide (200 μM) results in reduced cell viability (FIG. 5*a*), measured using the CCK-8 viability assay, which measures cellular reducing capacity. Interestingly, pre-treating myoblasts with precursor 1a for 4 h results in a dose-dependent decrease of $H_2O_2$-induced toxicity (FIG. 5*a*). Remarkably, pre-treatment with only 5 μM 1a for 8 h also shows protection against 200 μM of $H_2O_2$, demonstrating the potency of these newly developed alkylsulfenyl thiocarbonate RSSH precursors against oxidative stress. Under similar conditions, the phenol by-product shows no protective effect against $H_2O_2$-mediated toxicity, indicating that the protection is due to RSSH. The cytoprotective effect of 1a was also independently measured using the Sytox viability assay due to the potential background reduction of CCK-8 by reactive sulfur species leading to artifactual viability measurements. Tominaga et al., 1999. As shown in FIG. 5*b*, 1a consistently shows protective effects against $H_2O_2$-mediated toxicity. The protective effects against oxidative stress warrant future investigation as the potency of 1a suggests cytoprotective properties beyond direct scavenging of free-radical products derived from $H_2O_2$. Taken together, these results demonstrate the potential therapeutic benefit of RSSH donors in the context of oxidative stress and suggest that precursors that increase intracellular RSSH levels are potentially useful agents against oxidative stress-induced diseases.

1.3.5 Intracellular RSSH Release

Increased intracellular RSSH levels resulting from incubation with 1a utilizing SSP4, a fluorescent probe that has been used to detect of intracellular sulfane sulfur, Chen et al., 2013; Marutani et al., 2014, also was tested. Sulfane sulfur refers to a sulfur atom with six valence electrons and no charge. Biologically important sulfane sulfur compounds include RSSH, polysulfides ($RS_nSH$ or $RSS_nSR$, n≥1), inorganic polysulfides ($HSS_nH$, n≥1), and elemental sulfur ($S_8$). Briefly, cells were incubated with SSP4 in the presence of cetrimonium bromide (CTAB) for 20 min and then washed with serum-free media before 1a is introduced. A significant increase of the SSP4 fluorescence signal was not observed following treatment with 50 mM 1a due to the low amount of RSSH released at this concentration falling below the detection limit of the probe (FIG. 6). Dose-dependent increases in fluorescence intensity, however, are observed for 100 and 200 mM 1a over a period of 3 h. Since the SSP4 probe is known to react with a variety of sulfane sulfur species, the fluorescence signal observed upon treatment of 1a is likely due to RSSH and/or other sulfane sulfur species that might be present in the equilibrium with RSSH (e.g., Scheme 1-5). Thus, it is thought that the cytoprotective effects of 1a are attributed to increasing sulfane sulfur pools within the cultured cells.

1.4 General Information

Analytical thin layer chromatography (TLC) was performed on silica gel on TLC Al foils with fluorescent indicator F254 plates (Sigma-Aldrich). Visualization was accomplished with UV light (254 nm) or staining with $KMnO_4$. Starting materials, solvents, and reagents were received from commercial sources (Sigma-Aldrich, Oakwood Chemical, and TCI), unless otherwise noted and were used without purification. Deuterated solvents (Cambridge Isotope Laboratories) were used for NMR spectroscopic analyses. NMR spectra were obtained on a Bruker 400 MHz NMR spectrometer. In the case of $^1H$ NMR in $CDCl_3$, chemical shifts are reported relative to tetramethylsilane (δ=0). The other spectra are referenced internally according to residual solvent signals of deuterated chloroform (13° C. NMR; δ=77.16 ppm), and DMSO-$d_6$ ($^1H$ NMR; δ=2.50 ppm, and $^{13}C$ NMR; δ=39.52 ppm). High-resolution mass spectra were obtained on a Waters Acquity Q-ToF MS/MS instrument. The kinetics of hydropersulfide release was monitored using a high-performance liquid chromatography (HPLC, Agilent 1100 series) system with a Phenomenex C-18 reverse phase column (250 mm×4.6 mm, 5 μm). UPLC-MS analysis was carried out with a Waters Acquity/Xevo-G2 UPLC-MS system equipped with ACQUITY UPLC BEH C18 column (2.1 mm×50 mm, 1.7 μm). The mass signals for products of RSSH trapping with S-methylmethanethiosulfonate (MMTS) were obtained via deconvolution using MassLynx 4.1 software. In addition to the protonated molecule $[M+H]^+$, $[M+Na]^+$ adducts also were observed during ESI-MS analysis. The pH measurements were performed using a Fisher Scientific Accumet AB15 pH-meter.

1.5 General Procedure for Synthesis of Alkylsulfenyl Thiocarbonates 1a-f

A solution of chlorocarbonylsulfenyl chloride (1.53 mmol, 1.05 equiv) in $CH_2Cl_2$ (5 mL) was added dropwise to a solution of N-acetyl penicillamine methyl ester (1.46 mmol, 1 equiv) in $CH_2Cl_2$ (10 mL) at 0° C. under nitrogen atmosphere. The reaction mixture was stirred at 0° C. for 1 h. The volatiles were removed under reduced pressure to obtain methyl-2-acetamido-3-((chlorocarbonyl)disulfaneyl)-3-methylbutanoate, which was used for the next step without further purification. To a mixture of para-substituted phenols 4a-f (1.46 mmol, 1 equiv) and triethylamine (1.61 mmol, 1.1 equiv) in $CH_2Cl_2$ (10 mL), a solution of methyl- 2-acetamido-3-((chlorocarbonyl)disulfaneyl)-3-methylbutanoate (1.46 mmol, 1 equiv) in $CH_2Cl_2$ (5 mL) was added dropwise at 0° C. The resulting mixture was stirred at 0° C. until completion of the reaction (analyzed by TLC). The mixture was diluted with water and extracted with $CH_2Cl_2$ (10 mL×3). The combined organic layer was washed with brine, dried over $Na_2SO_4$, and concentrated under vacuum. The residue was purified by flash column chromatography on silica gel to afford the desired hydropersulfide precursors 1a-f.

Methyl 2-acetamido-3-methyl-3-((phenoxycarbonyl)disulfaneyl)butanoate (1a)

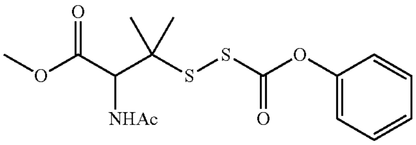 [SMILES: COC(=O)C(NC(C)=O)C(C)(C)SSC(=O)Oc1ccccc1]

White solid (293 mg, 60%); $^1$H NMR (400 MHZ, $CDCl_3$) δ 7.42-7.34 (m, 2H), 7.29-7.25 (m, 1H), 7.20-7.17 (m, 2H), 6.63 (d, J=9.2 Hz, 1H), 4.72 (d, J=9.0 Hz, 1H), 3.77 (s, 3H), 2.03 (s, 3H), 1.51 (s, 3H), 1.42 (s, 3H); $^{13}$C NMR (101 MHZ, $CDCl_3$) δ 170.4, 170.2, 169.5, 151.6, 129.7, 126.6, 121.0, 58.7, 53.5, 52.5, 26.3, 25.3, 23.2; HRMS (ESI) calcd. for $C_{15}H_{19}NO_5S_2$ ($[M+H]^+$358.0777, found: 358.0779.

Methyl 2-acetamido-3-methyl-3-(((p-tolyloxy)carbonyl)disulfaneyl)butanoate (1b)

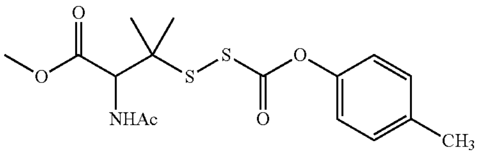

White solid (454 mg, 84%); $^1$H NMR (400 MHZ, $CDCl_3$) δ 7.18 (d, J=8.2 Hz, 2H), 7.06 (d, J=8.5 Hz, 2H), 6.65 (d, J=8.9 Hz, 1H), 4.71 (d, J=8.9 Hz, 1H), 3.77 (s, 3H), 2.35 (s, 3H), 2.03 (s, 3H), 1.51 (s, 3H), 1.41 (s, 3H); $^{13}$C NMR (101 MHZ, $CDCl_3$) δ 170.5, 170.3, 169.7, 149.5, 136.5, 130.2, 120.7, 58.8, 53.5, 52.5, 26.4, 25.5, 23.2, 21.0; HRMS (ESI) calcd. for $C_{16}H_{21}NO_5S_2$ ($[M+H]^+$372.0934, found: 372.0934.

Methyl 2-acetamido-3-(((4-methoxyphenoxy)carbonyl)disulfaneyl)-3-methylbutanoate (1c)

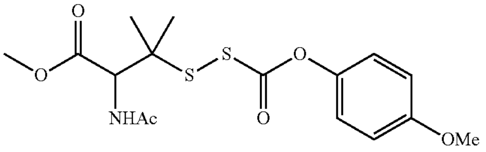 [SMILES: COC(=O)C(NC(C)=O)C(C)(C)SSC(=O)Oc1ccc(OC)cc1]

White solid (407 mg, 86%); $^1$H NMR (400 MHZ, $CDCl_3$) δ 7.10 (d, J=9.2 Hz, 2H), 6.89 (d, J=9.2 Hz, 2H), 6.65 (d, J=8.9 Hz, 1H), 4.71 (d, J=8.9 Hz, 1H), 3.80 (s, 3H), 3.76 (s, 3H), 2.03 (s, 3H), 1.50 (s, 3H), 1.41 (s, 3H); $^{13}$C NMR (101 MHz, $CDCl_3$) δ 170.4, 170.2, 169.8, 157.9, 145.2, 121.9, 114.7, 58.7, 55.7, 53.5, 52.5, 26.4, 25.4, 23.2; HRMS (ESI) calcd. for $C_{16}H_{21}NO_6S_2$ ($[M+H]^+$388.0883, found: 388.0880.

Methyl 2-acetamido-3-(((4-fluorophenoxy)carbonyl)disulfaneyl)-3-methylbutanoate (1d)

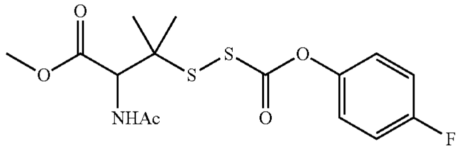 [SMILES: COC(=O)C(NC(C)=O)C(C)(C)SSC(=O)Oc1ccc(F)cc1]

White solid (363 mg, 65%); $^1$H NMR (400 MHZ, $CDCl_3$) δ 7.18-7.14 (m, 2H), 7.12-7.03 (m, 2H), 6.60 (d, J=8.9 Hz, 1H), 4.72 (d, J=9.0 Hz, 1H), 3.77 (s, 3H), 2.03 (s, 3H), 1.50 (s, 3H), 1.41 (s, 3H); $^{13}$C NMR (101 MHZ, $CDCl_3$) δ 170.5, 170.2, 169.7, 160.65 (d, J (CF)=245.5 Hz), 147.4 (d, J (CF)=3.0 Hz), 122.6 (d, J (CF)=8.5 Hz), 116.4 (d, J (CF)=23.7 Hz), 58.6, 53.6, 52.5, 26.4, 25.3, 23.2; HRMS (ESI) calcd for $C_{15}H_{18}FNO_5S_2$ ($[M+H]^+$376.0683, found: 376.0684.

Methyl 2-acetamido-3-methyl-3-(((4-(trifluoromethyl)phenoxy)carbonyl)disulfaneyl)butanoate (1e)

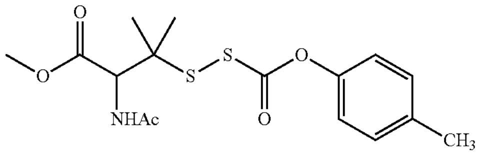

White solid (524 mg, 84%); $^1$H NMR (400 MHZ, $CDCl_3$) δ 7.67 (d, J=8.6 Hz, 2H), 7.33 (d, J=8.6 Hz, 2H), 6.58 (d, J=8.8 Hz, 1H), 4.75 (d, J=9.1 Hz, 1H), 3.77 (s, 3H), 2.04 (s, 3H), 1.50 (s, 3H), 1.42 (s, 3H); $^{13}$C NMR (101 MHZ, $CDCl_3$) δ 170.5, 170.2, 169.3, 153.8, 129.4, 129.0, 128.7, 128.4, 127.2, 125.1, 121.6, 58.5, 53.7, 52.5, 26.3, 25.2, 23.2; HRMS (ESI) calcd. for $C_{16}H_{18}F_3NO_5S_2$ ($[M+H]^+$426.0651, found: 358.0.651.

Methyl 2-acetamido-3-(((4-cyanophenoxy)carbonyl)disulfaneyl)-3-methylbutanoate (1f)

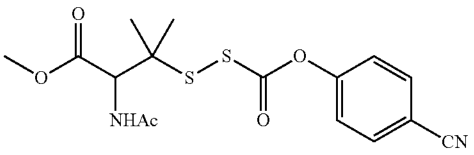 [SMILES: COC(=O)C(NC(C)=O)C(C)(C)SSC(=O)Oc1ccc(C#N)cc1]

White solid (317 mg, 75%); $^1$H NMR (400 MHZ, $CDCl_3$) δ 7.71 (d, J=8.9 Hz, 2H), 7.35 (d, J=8.9 Hz, 2H), 6.53 (d, J=9.0 Hz, 1H), 4.75 (d, J=9.0 Hz, 1H), 3.77 (s, 3H), 2.04 (s, 3H), 1.50 (s, 3H), 1.42 (s, 3H); $^{13}$C NMR (101 MHZ, $CDCl_3$) δ 170.5, 170.2, 169.0, 134.0, 122.2, 118.0, 110.6, 58.4, 53.8, 52.5, 26.2, 25.0, 23.2; HRMS (ESI) calcd. for $C_{16}H_{18}N_2O_5S_2$ ($[M+H]^+$383.0730, found: 383.0731.

Methyl 2-acetamido-3-(((benzyloxy)carbonyl)disulfaneyl)-3-methylbutanoate (8)

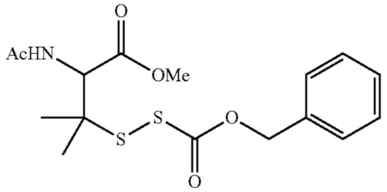 [SMILES: COC(=O)C(NC(C)=O)C(C)(C)SSC(=O)OCc1ccccc1]

This compound was prepared according to the procedure used for precursors 1a-f synthesis. White solid (65 mg, 12%); $^1$H NMR (400 MHZ, $CDCl_3$) δ 7.46-7.37 (m, 5H), 6.69 (d, J=8.4 Hz, 1H), 5.41-5.23 (m, 2H), 4.65 (d, J=8.9 Hz, 1H), 3.73 (s, 3H), 2.03 (s, 3H), 1.45 (s, 3H), 1.36 (s, 3H); $^{13}$C NMR (101 MHz, $CDCl_3$) δ 170.44, 170.39, 170.3, 134.6, 129.1, 128.9, 128.8, 71.1, 58.9, 53.2, 52.5, 26.3, 25.5, 23.2; HRMS (ESI) calcd. for $C_{16}H_{21}N_2O_5S_2$ ($[M+H]^+$372.0934, found: 372.0939.

Methyl N-acetyl-S-(phenoxycarbonyl)cysteinate (9a)

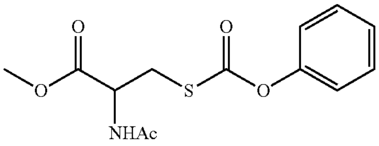 [SMILES: COC(=O)C(CSC(=O)Oc1ccccc1)NC(C)=O]

To a stirred solution of N-acetyl cysteine methyl ester (1 g, 5.64 mmol) in dichloromethane (10 mL), phenylchloroformate (1.33 g, 8.46 mmol) and triethylamine (571 mg, 5.64 mmol) was added at 0° C. The resulting mixture was allowed to stir at room temperature for 12 h. The reaction was quenched with saturated aq. $NH_4Cl$ (20 mL), and the resulting mixture was extracted with EtOAc (20 mL×3). The organic layer was washed with water (20 mL) and brine (20 mL) sequentially. The combined organic phases were dried over anhydrous $Na_2SO_4$, filtered, and concentrated under reduced pressure. Purification by column chromatography afforded compound 9a (769 mg, 46%) as a white solid. $^1$H NMR (400 MHZ, $CDCl_3$) δ 7.40-7.36 (m, 2H), 7.27-7.25 (m, 1H), 7.14-7.12 (m, 2H), 6.47 (d, J=7.5 Hz, 1H), 4.91 (ddd, J=7.6, 5.8, 4.8 Hz, 1H), 3.76 (s, 3H), 3.44 (ddd, J=20.3, 14.4, 5.3 Hz, 2H), 2.03 (s, 3H); $^{13}$C NMR (101 MHZ, $CDCl_3$) δ 170.7, 170.1, 169.7, 151.2, 129.6, 126.4, 121.1, 52.9, 52.0, 33.2, 23.1; HRMS (ESI) calcd. for $C_{13}H_{15}NO_5S$ ($[M+H]^+$298.0744, found: 298.0751.

SS-benzyl O-(4-methoxyphenyl)carbono(dithioperoxoate) (13)

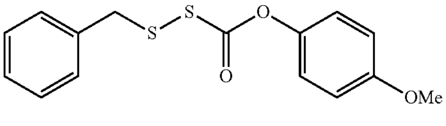 [SMILES: COc1ccc(OC(=O)SSCc2ccccc2)cc1]

A solution of chlorocarbonylsulfenyl chloride (1.05 g, 8.05 mmol) in $CH_2Cl_2$ (5 mL) was added dropwise to a solution of benzyl mercaptan (1 g, 8.05 mmol) in $CH_2Cl_2$ (10 mL) at 0° C. under nitrogen atmosphere. The reaction mixture was stirred at 0° C. for 1 h. The mixture was added dropwise to a mixture of 4-methoxyphenol (670 mg, 5.40 mmol) and N,N-diisopropylethylamine (1.05 g, 8.05 mmol) in $CH_2Cl_2$ (10 mL) at 0° C. The resulting mixture was stirred at 0° C. for 1 h. The mixture was quenched with water and extracted with $CH_2Cl_2$ (10 mL×3). The combined organic layer was washed with brine, dried over $Na_2SO_4$, and concentrated under vacuum. The residue was purified by flash column chromatography on silica gel to afford the compound 13 (1.37 g, 83%) as a colorless oil. $^1$H NMR (400 MHZ, $CDCl_3$) δ 7.37-7.26 (m, 5H), 7.03 (d, J=9.2 Hz, 2H), 6.87 (d, J=9.2 Hz, 2H), 4.05 (s, 2H), 3.79 (s, 3H); $^{13}$C NMR (101 MHZ, $CDCl_3$) δ 168.9, 157.8, 145.2, 135.7, 129.7, 128.8, 128.0, 121.9, 114.6, 55.7, 43.3.

1.6 RSSH Generation from 1a in the Presence of β-(4-hydroxyphenyl)ethyl iodoacetamide (HPE-IAM)

RSSH precursor 1a and HPE-IAM were dissolved in DMSO to afford a 10 mM and 100 mM stock, respectively. Briefly, HPE-IAM (30 μL, 100 mM) was added in pH 7.4 ammonium bicarbonate buffer (50 mM, 2.94 mL) containing DTPA (100 mM) as metal chelator. The mixture was preincubated for 10 min at 37° C. Precursor 1a (30 μL, 10 mM) was added into the mixture and incubated at 37° C. for 2 h. An aliquot of the reaction mixture (500 μL) was withdrawn and quenched with 500 μL of 1% formic acid solution and analyzed by UPLC-MS as follows: Mobile phase: 0-1 min 90% water+0% ACN+10% of 0.1% formic acid (v/v) in water; 1-7.5 min gradient up to 10% water+80% ACN+10% of 0.1% formic acid (v/v) in water; 7.5-8.4 min 10% water+80% ACN+10% of 0.1% formic acid (v/v) in water; 8.4-8.5 min gradient up to 90% water+0% ACN+10% of 0.1% formic acid (v/v) in water, 8.5-10 min 90% water+0% ACN+10% of 0.1% formic acid (v/v) in water. Flow rate=0.3 mL/min. These studies were conducted at least in triplicate and representative spectra are presented.

Figure 9:
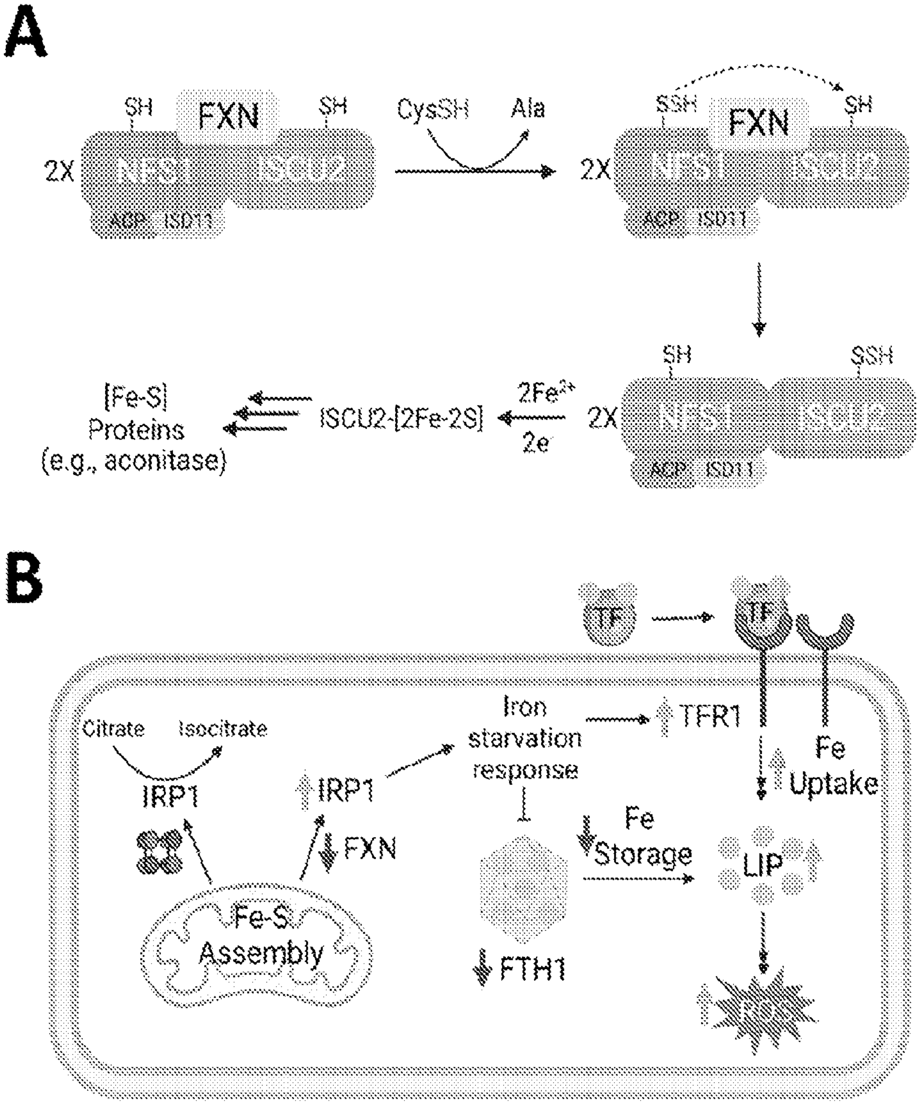

1.7 HRMS Spectra of RSS-HPE-AM and Dialkyl Trisulfide Formed During Incubation of 1a with HPE-IAM HRMS spectra of RSS-HPE-AM and dialkyl trisulfide formed during incubation of 1a with HPE-IAM are shown in FIG. 7, FIG. 8, and FIG. 9.

1.8 RSSH Generation from 1a-f in the Presence of S-Methyl Methanethiosulfonate (MMTS)

In general, RSSH precursors 1a-f and MMTS were dissolved in DMSO to afford a 10 mM and 100 mM stock, respectively unless stated otherwise. Briefly, MMTS (30 μL, 100 mM) was added in pH 7.4 ammonium bicarbonate buffer (50 mM, 2.94 mL) containing DTPA (100 μM) as metal chelator. The resulting solution was pre-incubated at 37° C. for 10 min. Precursor 1a-f (30 μL, 10 mM) were independently added into the mixture and incubated at 37° C. An aliquot of the reaction mixture (500 μL) was withdrawn and quenched with 500 μL of 1% formic acid solution and analyzed using UPLC-MS.

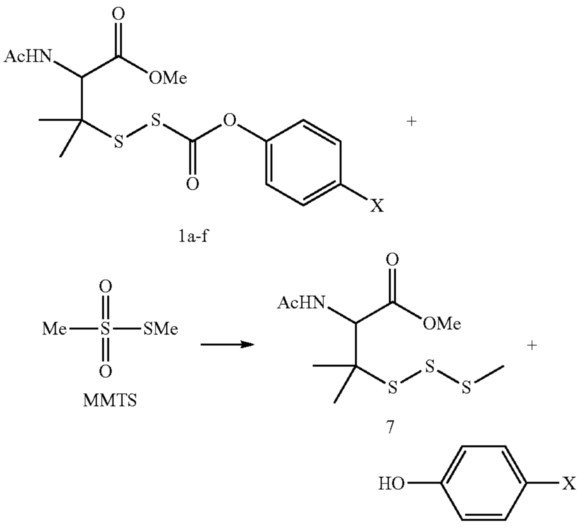

1a-f

MMTS

7

4a-f

1.9 HRMS Spectra of RSS-S-Me 7 Formed During Incubation of 1a-f with MMTS

HRMS spectra indicate that RSS-S-Me 7 is formed during incubation of 1a-f with MMTS (not shown).

1.10 Kinetics of RSSH Release from Precursors 1a-f and 8 Monitored by HPLC

MMTS (100 μL, 50 mM) was added in pH 7.4 phosphate buffer saline (4.85 mL) containing the DTPA (100 μM) as metal chelator. This solution was preincubated for 10 min at 37° C. and then precursor 1a-f or 8 (50 μL, 10 mM) were independently added into the mixture (total volume=5 mL). The resulting solution was incubated at 37° C. At different time points, an aliquot of 300 μL was taken and quenched with 300 μL 0.1% formic acid solution. These samples were stored at 0° C. until HPLC analysis was performed. The sample (20 μL) was injected into a high-performance liquid chromatography (HPLC) equipped with Phenomenex C-18 reverse phase column (250 mm×4.6 mm, 5 μm). HPLC Method: mobile phase A ($H_2O$) and mobile phase B (ACN), flow rate: 1 mL/min, run time: 21 min, the gradient elution method: 10% to 70% B from 0 to 10 min, 70% to 90% B from 10 to 21 min. The elution was monitored by a UV detector at 240 and 275 nm. First-order rate constants were obtained by plotting the precursor decay and phenol by-product formation as a function of time.

1.11 Decomposition of 1a and 8 in the Presence of N-Acetyl Cysteine Methyl Ester To a solution of N-acetyl cysteine methyl ester (500 μM) in pH 7.4 phosphate buffer saline (100 mM) containing DTPA (100 μM), precursor 1a or 8 (100 μM) was added. The resulting mixture was incubated at 37° C. At different time points, an aliquot of the reaction mixture (500 μL) was withdrawn and transferred to pre-cooled 0.1% formic acid (500 μL) and analyzed using HPLC. First-order rate constants were obtained by plotting the precursor decay as a function of time.

1.12 RSSH Generation from 1a in the Presence of N-Acetyl Cysteine Analyzed by UPLC-MS To a solution of N-acetyl cysteine (500 μM) in pH 7.4 ammonium bicarbonate buffer (50 mM) containing DTPA (100 μM), precursors 1a (100 μM) was added. The resulting mixture was incubated at 37° C. An aliquot (200 μL) of reaction mixture was withdrawn at specified time points and quenched with 1% formic acid (200 μL). These samples were stored at 0° C. until UPLC-MS analysis was performed. See FIGS. S10-S22.

1.13 Rssh Generation from 8 in the Presence of N-Acetyl Cysteine Analyzed by UPLC-MS To a solution of N-acetyl cysteine (500 μM) in pH 7.4 ammonium bicarbonate buffer (50 mM) containing DTPA (100 μM), precursors 8 (100 μM) was added. The resulting mixture was incubated at 37° C. An aliquot (200 μL) of reaction mixture was withdrawn at specified time points and quenched with 1% formic acid (200 μL). These samples were stored at 0° C. until UPLC-MS analysis was performed. See FIGS. S23-S33.

(1)

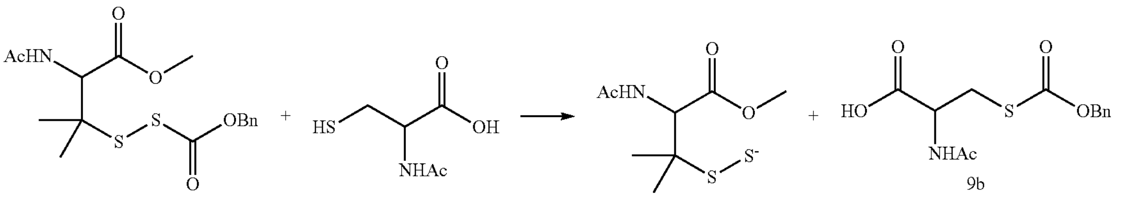

8

9b (2)

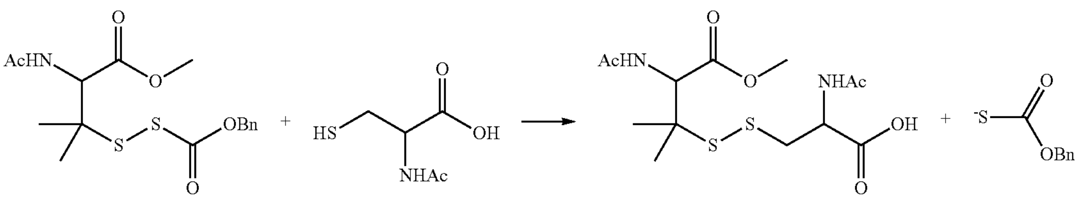

8

'S2

-continued (3)

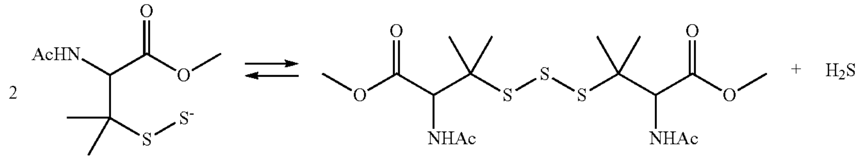

(4)

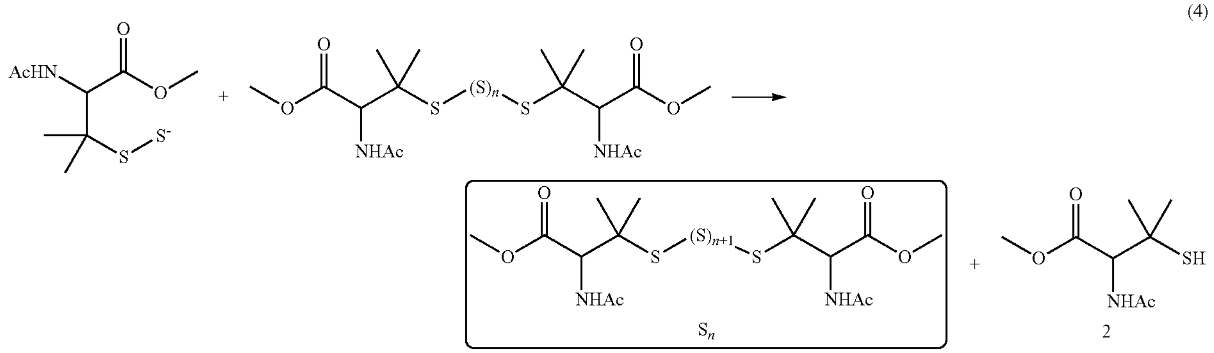

$S_n$

2

(5)

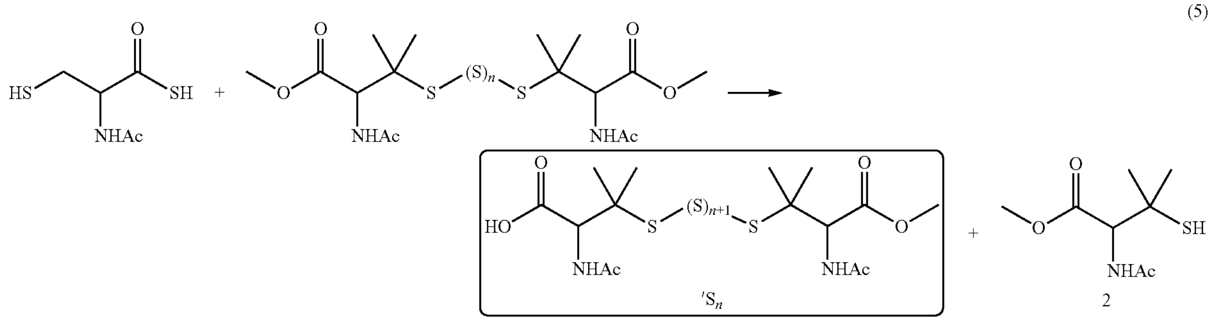

$'S_n$

2

1.14 Decomposition of Control Compound 13 in the Presence of N-Acetyl Cysteine (1)

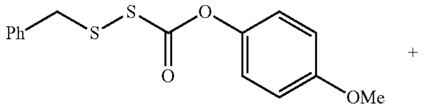

13

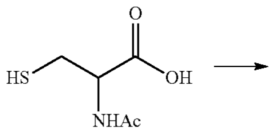

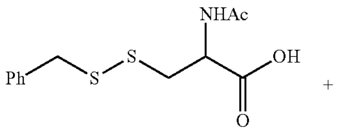

14

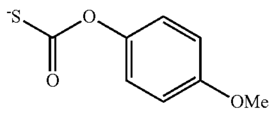

11c

-continued (2)

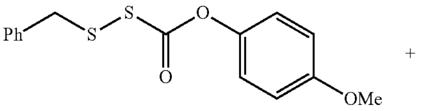

13

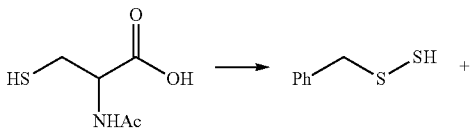

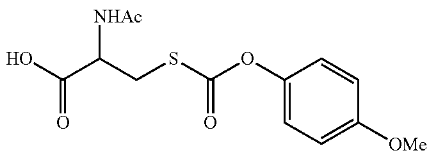

9c

UPLC-MS analysis of decomposition of 13 in the presence of N-acetyl cysteine shows exclusive unsymmetrical disulfide 14 formation, indicating that NAC selectively reacts at the disulfide bond (eq. 1). Alternatively, thiol can react at the carbonyl carbon to produce BnSSH and S-alkyl thiocarbonate 9c (eq. 2). Evidence of 9c formation under these conditions, however, was not observed.

1.15 Analysis of COS Release from RSSH Precursors in the Presence of Thiols Using MIMS COS was analyzed using a Hiden HPR-40 MIMS system with a sample cell and membrane probe that have been optimized to detect gases dissolved in aqueous solution as described previously. Cline et al., 2011. Stock solutions of N-acetyl-cysteine (25 mM) and glutathione (25 mM) were prepared in DI water. RSSH precursors stock solutions (5 mM) were prepared in DMSO. These solutions were degassed by purging with nitrogen for 10 min. Typically, 20 mL phosphate buffer solution (10 mM) was added to the sample cell, degassed, and purged with a continuous flow of argon for 25 min. N-acetyl cysteine (200 μL, 25 mM) or glutathione (200 μL, 25 mM) and RSSH precursor (200 μL, 5 mM) were then injected using a gas tight syringe and ion current at m/z 60 ($COS^+$) were collected (source pressure was approximately $1\times10^{-7}$ to $5\times10^{-7}$ Torr). See FIG. 7.

1.16 Culture of Cells

H9c2 embryonic rat heart myoblasts were obtained from the American Type Culture Collection. Cells were grown in Dulbecco's minimal essential medium (DMEM), supplemented with fetal bovine serum (FBS) 10%, penicillin 100 U/mL and streptomycin 100 μg/mL. They were propagated in T75-flasks, split before reaching 70-80% confluence (usually every day or every second day), and used within 11 passages. Cells were passaged to tissue culture treated 96-well microtiter plates at the specified density in 180 μL volumes and incubated for 24 h.

1.17 Cytotoxicity Study of 1a

Cells were seeded at a density of $1\times10^4$ cells/well. After 24 h, the media was replaced and compound added in 20 μL volumes using DMSO:$H_2O$ (<0.01% DMSO) as the vehicle. Cells were incubated for an additional 24 h before media was removed. Then, 100 μL of media containing 3 μM Sytox Green nucleic acid stain (Invitrogen) was added and the cells were incubated for 2 h before fluorescence readings were obtained at $485_{Ex}/538_{Em}$ (Step 1). Finally, an additional 100 μL of media containing 3 μM Sytox and 0.2% Triton X-100 was added to permeabilize all cells and incubated for 1 h before fluorescence values measured (Step 2). The relative % cells surviving was calculated as a 100% minus the ratio of the fluorescence value of Step 1 over Step 2 (% cells surviving=100%−($FL_{538}$ (Step 1)/$FL_{538}$ (Step 2)). See FIG. 8.

1.18 H9c2 Cell Protection by Precursor 1a from $H_2O_2$-Mediated Oxidative Stress Cell Counting Kit-8 (CCK-8) (Tominaga et al., 1999)

Cells were seeded at a density of $5\times10^3$ cells/well. After 24 h, precursor 1a or by-product 4a was added at 20 μL volumes using DMSO:$H_2O$ (<0.01% DMSO as the vehicle). Cells were incubated for 2 h before media was removed and the cells gently washed with PBS (pH 7.4). Then, 180 μL of fresh media and 20 μL $H_2O_2$ diluted into $H_2O$ were added and cells were incubated for an additional 2 h. At the completion of $H_2O_2$ exposure, each well is carefully washed 3 times with PBS (pH 7.4) before adding 100 μL of media, without-FBS, containing 10% v/v CCK-8 (Dojindo) and incubated for 3 h prior to obtaining absorbance values at 450 nm. The relative % viability was calculated as 100 times the ratio of the $Abs_{450}$ (pre-treated, $H_2O_2$-exposed) over $Abs_{450}$ (vehicle-treated, non $H_2O_2$-exposed).

1.19 Sytox Green Nucleic Acid Stain (Hofgaard et al., 2006)

Cells were seeded at a density of $1\times10^4$ cells/well. After 24 h, precursor 1a or by-product 4a is added in 20 μL volumes using DMSO:$H_2O$ (<0.01% DMSO). Cells were incubated for 2 h before media was removed and the cells gently washed with PBS (pH 7.4). Then, 180 μL of fresh media and 20 μL $H_2O_2$ diluted in $H_2O$ were added before cells were incubated for an additional 1 h. After removing this media, 100 μL of media containing 3 μM Sytox Green nucleic acid stain was added, and the cells incubated for 2 h before fluorescence readings were obtained at $485_{Ex}/538_{Em}$ (Step 1). Finally, an additional 100 μL of media containing 3 μM Sytox and 0.2% Triton X-100 was added to permeabilize all cells and incubated for 1 h before fluorescence values measured (Step 2). The relative % cells surviving was calculated as a 100% minus the ratio of the fluorescence value of Step 1 over Step 2 (% cells surviving=100%−($FL_{538}$ (Step 1)/$FL_{538}$ (Step 2)). Fluorescence values for vehicle-treated, non-$H_2O_2$-exposed wells were treated as background cell death and this value is added to the % cell survival for each subsequent group.

1.20 Intracellular Sulfane Sulfur Detection Using the SSP4 Probe (Chen et al., 2013)

Cells were seeded at a density of $1.5\times10^4$ cells/well. After 24 h, the media is removed, and the cells are washed two times with fresh serum-free media. Then, 20 μM SSP4 and 500 μM CTAB are introduced to the cells in a 100 μL volume of serum-free media for 20 minutes. The SSP4/CTAB solution is removed, and the cells are washed two times with fresh serum-free media. Finally, 100 μL of serum-free media containing 50, 100, or 200 μM of 1a is added to the wells and incubated at 37° C. The fluorescence readings were obtained at $482_{Ex}/515_{Em}$.

1.21 Summary

The presently disclosed subject matter provides a new strategy for efficient RSSH generation based on the hydrolysis of alkylsulfenyl thiocarbonates under physiologically relevant conditions. RSSH generation from these precursors can be tuned by modifying the thiocarbonate carbonyl group's electrophilicity. These alkylsulfenyl thiocarbonates also generate RSSH in the presence of thiol. As a proof-of-principle of possible protective effects associated with RSSH, the potential benefit of these donors in the context of oxidative stress in H9c2 cardiac myoblasts has been demonstrated. Furthermore, these precursors also increase intracellular sulfane sulfur levels in H9c2 cells. It is thought that this series of RSSH precursors may be used as a research tool for delineating RSSH cell signalling mechanisms.

Example 2

Hydropersulfides (RSSH) Improve Iron-Sulfur Cluster Biosynthesis in a Cellular Model of Friedreich's Ataxia 2.1 Overview Iron-sulfur (Fe—S) clusters are ubiquitous cofactors required for the function of proteins involved in a wide range of activities, including electron transport in respiratory chain complexes, regulatory sensing, and DNA synthesis/repair. Research over the past decade has revealed that impaired Fe—S cluster biogenesis is linked to several diseases, including Friedreich's Ataxia (FA). FA patients exhibit a deficiency in the protein frataxin (FXN), which is a key protein for enhanced activity of the cysteine desulfurase NFS1 and acceleration of sulfane-sulfur transfer from NFS1 to iron-sulfur cluster scaffold protein 2 (ISCU2), the site of de novo Fe—S cluster assembly. In this example, it was found that treatment of FA patient skin fibroblasts with hydropersulfides (RSSH) results in increased cell viability following hydrogen peroxide ($H_2O_2$) stress and erastin-induced ferroptosis, as well as reduction of lipid peroxidation under ferroptotic conditions. Importantly, we observe an increase in aconitase activity, a crucial Fe—S cluster protein in the Kreb's Cycle, under stress conditions. Furthermore, RSSH increases the expression of the key iron storage protein ferritin heavy chain 1 (FTH1) and decreases iron uptake protein transferrin-receptor 1 (TFR1) expression, suggesting that RSSH administration may ultimately aid in maintaining iron homeostasis.

2.2 Background

Friedrich's ataxia (FA) is an autosomal recessive progressive neurodegenerative disease caused by the expansion of triplet nucleotide GAA repeats in the first intron of the frataxin (FXN) gene. Dürr et al., 1996; Campuzano et al., 1996. The GAA expansion mutation leads to reduction in the transcription of FXN, a highly conserved mitochondrial protein involved in iron-sulfur (Fe—S) cluster biosynthesis. Johnson et al., 2005; Lill and Mühlenhoff, 2008; Gottesfeld, 2007. Fe—S clusters are redox-active protein cofactors that are essential for fundamental life processes such as energy production, metabolic conversions, DNA maintenance, and gene expression regulation. Rouault and Tong, 2008. De novo biosynthesis of Fe—S clusters occurs within the mitochondria by a multicomponent assembly complex (FIG. 9A). Rouault and Maio, 2017; Gervason et al., 2019; Rouault, 2019. A cysteine desulfurase complex comprised of the proteins, NFS1, ISD11, and ACP, catalyzes the conversion of L-cysteine to L-alanine and generates a hydropersulfide (RSSH) intermediate on a cysteine residue of NFS1. The terminal sulfur of this intermediate is then transferred to the scaffold protein ISCU2, where it is combines with ferrous iron and electrons (from a ferredoxin) to form Fe—S clusters. Once the cluster is assembled on ISCU2, it is transferred to acceptor proteins (e.g., aconitase) with the help of additional components of the mitochondrial Fe—S cluster machinery. Several studies have demonstrated the critical role of FXN in Fe—S cluster biogenesis. It stimulates cysteine desulfurase activity to produce NFS1-SSH and accelerates the sulfane sulfur transfer from this intermediate to a scaffold protein ISCU2 generating ISCU2-SSH. Gervason et al., 2019; Patra and Barondeau, 2019; Pandey et al., 2013; Cai et al, 2017; Shi et al., 2012; Puglisi and Pastore, 2018.

Dysregulated iron metabolism is a key feature of FA. FXN deficiency leads to a series of alterations in the activity and/or expression of different iron-handling proteins. Among the most relevant changes observed in FA models, is an increase in the activity of iron regulatory proteins 1 and 2 (IRP1 and IRP2). Upon Fe—S cluster dissociation, IRP1 activates an iron-starvation response (FIG. 9B). When activated, the iron-starvation response increases the labile iron pool by increasing iron absorption via upregulation of transferrin receptor 1 (TFR1) and decreasing iron storage via downregulation of ferritin heavy chain 1 (FTH1). Excessive iron accumulation increases reactive oxygen species (ROS) via the Fenton reaction, leading to mitochondrial dysfunction and ultimately cell death.

Several pre-clinical and clinical studies have indicated that oxidative damage plays an important role in FA. Lupoli et al., 2018. FA typically begins in mid-childhood and affects multiple systems, including progressive loss of voluntary muscle control and coordination, debilitating scoliosis, and ultimately heart failure leading to premature death. Pandolfo, 1999; Pandolfo, 2009. Unfortunately, there are no approved treatments for FA other than supportive care. Therapies aimed at alleviating the effects of FA are crucial to ameliorate the devastating symptoms associated with the disease and slow its progression.

Proposed therapeutic strategies to treat FA include genetic approaches to increase FXN. Ocana-Santero, 2021. One of the downstream consequences of FXN deficiency is exacerbated oxidative stress, and therefore, alleviating oxidative stress has been considered a potentially promising strategy to treat FA. Lupoli et al., 2018. Antioxidants such as idebenone and tocopherols have shown promising results in FA models; Hart et al., 2005; Di Prospero et al., 2007 however, most drugs that aim to reduce ROS production directly have thus far regrettably failed to show positive impacts during clinical trials.

Another hallmark of FA is the decline in the expression and function of nuclear factor erythroid 2-related factor 2 (Nrf2), leading to oxidative stress and mitochondrial dysfunction. Nrf2 activators such as omaveloxolone have been reported to improve mitochondrial function, restore redox balance, and reduce inflammation in models of FA. Abeti et al, 2018. Based on our current understanding of FA pathogenesis; a multi-therapy approach is likely needed to tackle the multiple pathological facets composing this disease.

Herein, we examine hydropersulfide (RSSH) donation as a new strategy to counter the multiple downstream effects of FXN deficiency in FA. RSSH are a class of reactive sulfur species intimately linked biochemically to the endogenously produced "gasotransmitter", hydrogen sulfide ($H_2S$). Gadalla and Snyder, 2010. Emerging evidence shows that many biological effects initially ascribed to H2S may instead be due to RSSH and other higher order polysulfur species (RSSnH, RSSnR, HSnH, n>1). Filipovic et al., 2018; Mustafa et al., 2009. RSSH are highly prevalent in mammalian tissues and fluids, and accumulating evidence indicates that RSSH confer substantial protection against oxidative and electrophilic stress. Ida et al., 2014. Explanations for RSSH effectiveness include their superior reductive and nucleophilic properties compared to the corresponding thiols. Park et al., 2015; Khodade et al., 2022. Thus, they are superior scavengers of toxic oxidants/electrophiles. Furthermore, RSSH in the neutral state may react with protein thiols (P-SH) resulting in protein persulfide (P-SSH) generation, which can provide protection against overoxidation. Benchoam et al, 2019; Doka et al., 2020. Perhaps most importantly, beyond being excellent chemical antioxidants, RSSH may also stimulate endogenous antioxidant defense pathways via activation of Nrf2 by persulfidation of Kelch-like ECH-associated protein 1 (KEAP-1) critical cysteine residues. Kaspar et al., 2009; Hyberson et al., 2011; Wakabayashi et al., 2004.

2.3 Results and Discussion

2.3.1 Generation of RSSH Via a Donor

RSSH are intrinsically unstable and require donor molecules for their administration and study. Khodade et al., 2002; Dillon and Matson, 2021. To this end, we have developed several precursors that efficiently release RSSH with a range of half-lives under physiologically relevant conditions. Khodade et al., 2021; Khodade et al., 2020; Khodade and Toscano, 2018. Herein, we utilize an alkylsulfenyl thiocarbonate RSSH precursor (AST) with a half-life of 129 min in pH 7.4 solution at 37° C. (Scheme 2-1). Khodade et al., 2021. Advantages of this precursor include production of a relatively stable tert-alkyl hydropersulfide that is a good substrate for protein persulfidation reactions and release of a biologically innocuous byproduct, phenol. Importantly, we have demonstrated that AST increases intracellular RSSH levels and potently protects H9c2 cardiac myoblasts against oxidative stress. Khodade et al., 2021.

Scheme 2-1. RSSH release from AST

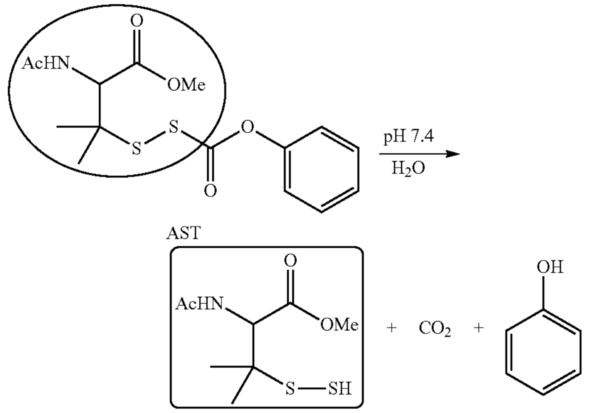

2.3.2 RSSH Ameliorates $H_2O_2$ Induced Cytotoxicity in FA Fibroblasts

Initially, we measured the cytotoxicity of AST in FA skin fibroblasts (GM04078), obtained from the Coriell Institute, to ensure that the RSSH donor itself is not cytotoxic. Precursor AST and its phenol byproduct do not show toxicity toward FA fibroblasts after 24 h of exposure at least up to 100 μM. We then measured the ability of AST to confer cytoprotection in FA fibroblasts against hydrogen peroxide ($H_2O_2$) stress. As expected, treatment of $H_2O_2$ at 75 μM for 4 h reduces cell viability by more than half (FIG. 10A). Importantly, this $H_2O_2$-mediated adverse effect was attenuated by AST. Under similar conditions, the byproduct phenol was ineffective, suggesting that the observed cytoprotection is due to RSSH.

2.3.3 RSSH Inhibits Erastin-Induced Ferroptosis in FA Fibroblasts

We next sought to determine whether AST would protect FA fibroblasts against erastin-induced cell death. Erastin is an inducer of ferroptosis, an iron-dependent form of cell death. It acts as an inhibitor of the cystine glutamate antiporter (system Xc), inhibiting the import of cystine, which leads to downstream depletion of glutathione (GSH) and ultimately to elevated ROS production. Satisfyingly, RSSH exhibited nearly complete protection against erastin-induced ferroptosis with 25 μM and 50 μM of AST (FIG. 10B). The increased viability suggests that RSSH can rescue the cell from cystine depletion and ultimately ferroptosis.

2.3.4 RSSH Scavenges Lipid Peroxides

The reduction of FXN levels in FA increases mitochondrial iron accumulation, ultimately leading to iron-dependent accumulation of lipid ROS and subsequent lipid peroxidation. Hence, we tested the ability of RSSH to attenuate lipid peroxidation in FA fibroblasts as assayed by flow cytometry. As has been reported previously, we employed C11-BODIPY (581/591) to monitor a shift in fluorescence of oxidized C11-BODIPY. We find that cells challenged with erastin at 10 mM displayed increased lipid peroxidation levels compared to the control group (FIG. 11). Dixon et al., 2012; Martinez et al., 2020. Importantly, AST (50 μM) pre-treatment for 4 h attenuated erastin-induced lipid peroxide levels. This result is consistent with AST protection against erastin-induced stress, as lipid peroxidation is a key biomarker of FA disease.

2.3.5 RSSH Restores Aconitase Activity in FA Fibroblasts

FXN deficiency results in diminished activity of various mitochondrial proteins that contain Fe—S cluster cofactors. For example, aconitase activity is affected in FA fibroblasts. Rötig et al., 1997. Aconitase catalyzes the stereospecific isomerization of citrate to isocitrate in the tricarboxylic acid cycle and its activity is highly dependent on an intact $[4Fe\text{-}4S]^{2+}$ cluster. We examined the impact of RSSH in FA fibroblasts on aconitase activity, the increase of which is reflective of preserved or augmented Fe—S cluster biosynthesis. FIG. 12A show that treatment with 75 mM $H_2O_2$ decreases aconitase activity by approximately 50%. Conversely, 4 h pretreatment of AST at varied concentrations (10, 25, 50 μM) rescues aconitase activity to levels found in control ($H_2O_2$-untreated) cells. To corroborate further that AST can effectively preserve or enhance Fe—S cluster assembly under challenging biological conditions, we conducted analogous experiments replacing $H_2O_2$ with erastin. Treatment of FA fibroblasts with erastin at 10 mM impaired aconitase activity substantially, but again, pretreatment of cells with AST attenuated this adverse effect (FIG. 12B).

Given these encouraging results, it was critical to determine whether the RSSH's positive impact on aconitase activity was due to enhanced Fe—S cluster biosynthesis or increased aconitase expression. Data shown in FIG. 13 suggests that $H_2O_2$ does not affect aconitase protein expression levels. Furthermore, prolonged AST treatment also does not alter aconitase protein expression, suggesting that RSSH administration enhances aconitase activity via increased Fe—S cluster biosynthesis. Similarly, erastin treatment either alone or in combination with AST showed no significant impact on aconitase expression levels. These results support the notion that RSSH donors can protect cells against erastin-induced ferroptosis and can rejuvenate Fe—S cluster biosynthesis.

2.3.6 RSSH Effect on Iron Metabolism as a Result of Erastin-Induced Ferroptosis Dysregulated iron metabolism is a key feature of FA. Iron homeostasis is regulated by IRPs (IRP1 and IRP2) which act by binding to RNA stem-loops known as iron-responsive elements (IREs) in target mRNAs. Under normal conditions, IRP1, occupied with an Fe—S cluster, acts as a cytosolic aconitase. However, under impaired Fe—S cluster conditions, IRP1 binds to IREs leading to upregulation of iron absorption (via increased expression of transferrin receptor 1 (TFR1)) and downregulation of iron storage (via decreased expression of ferritin heavy chain 1 (FTH1)). Considering the RSSH-induced enhancement of aconitase activity observed with AST, without wishing to be bound to any one particular theory, it was thought that this could ultimately aid in maintenance of iron homeostasis.

To test this hypothesis, we studied the effect of RSSH on TFR1 and FTH1 expression levels. We anticipated that the impacts of RSSH would result in downregulation of TFR1 and upregulation of FTH1. Immunoblot analysis shows erastin treatment upregulates TFR1 and downregulates FTH1 in FA fibroblasts, confirming its ability to impair Fe—S cluster biosynthesis. Feng et al., 2020; Park and Chung, 2019. Interestingly, pretreatment of FA fibroblasts with AST (25 and 50 μM) for 4 h leads to as low as a three-fold decrease of the TFR1 protein (FIG. 14A, FIG. 14C) and as a high as a two-fold increase of the FTH1 protein (FIG. 14B, FIG. 14D). These results suggest that RSSH treatment results in a decrease in intracellular iron overload via reduced levels of TFR1 and increases iron storage via higher levels of FTH1.

2.4 Summary

The evidence presented in this study demonstrates the use of RSSH donors as a potential therapeutic for FA and other diseases involving impaired Fe—S cluster biosynthesis. FXN enhances the cysteine desulfurase activity of the initial mitochondrial Fe—S cluster assembly and facilitates the transfer of a sulfane sulfur from NFS1 to the de novo Fe—S assembly protein ISCU2 in mammalian cells. The formation of the RSSH post-translational modification is a key step in Fe—S cluster formation. Presumably, in FA patients this step has been attenuated significantly resulting in the buildup of the labile iron pool leading to increased ROS levels (FIG. 15).

The data presented in this study affirms AST as a protective species against $H_2O_2$ stress and erastin-induced ferroptosis. The use of erastin as a stressor leads to inhibition of cystine uptake via inhibition of the glutamate-cystine antiporter system Xc. Dixon et al., 2012. The impediment of cystine uptake will presumably deplete the cell of cysteine, the key substrate for NFS1. Moreover, an iron starvation response is stimulated with depletion of Fe—S clusters, leading to further iron-induced oxidative damage. The presently disclosed data suggest that AST can decrease lipid peroxidation under ferroptotic conditions and also revive aconitase activity following $H_2O_2$ and erastin stress. We also observe an increase in FTH1, the iron storage protein, and a decrease in TFR1, the iron uptake protein. Previous studies have indicated that persulfidation on both NFS1 and ISCU2 is crucial for de novo Fe—S cluster biosynthesis. Johnson et al., 2005; Lill and Mühlenhoff, 2008; Freibert et al., 2021. While more work is necessary to gain deeper mechanistic insight, this study suggests that RSSH donors should be explored further as a novel therapeutic for FA.

Example 3

Persulfide Donors for Treating Anthracycline-Induced Cardiotoxicity

3.1 Overview

Anti-cancer therapies, including anthracyclines, such as doxorubicin (DOX), are very effective against many forms of malignancies. Disappointingly, they also can lead to progressive dose-dependent cardiomyopathy and eventually heart failure (HF). There is no current optimal strategy for preventing and/or managing this anthracycline-induced cardiotoxicity (AIC). Given the significantly large number of patients receiving DOX, this represents a substantial unmet clinical milestone.

Unremitted reactive oxygen species (ROS) emission and mitochondrial dysfunction are two main AIC stigmata. Current antioxidant-based therapies, however, continue to provide insufficient shelter against DOX-induced cardiomyopathy, while mitochondria-targeted therapies are just emerging as an appealing alternative. This example provides data supporting mitochondria-targeted hydropersulfide (RSSH) donors as a new and effective AIC treatment.

RSSH are a class of reactive sulfur species intimately linked biochemically to the "gasotransmitter", hydrogen sulfide ($H_2S$). The presently disclosed data indicate that RSSH can protect cardiac cells from DOX-induced oxidative damage via activation of endogenous antioxidant defense pathways without altering, but even enhancing DOX impact on cancer cells. Additional data suggest that this disparity is due to the dramatic difference in basal levels of reactive sulfur species between the two cell types, which, without being bound to any one particular theory, is thought to lead to reductive stress in cancer cells.

Finally, this example shows that the presently disclosed RSSH donors can outweigh dexrazoxane (DRZ), the only currently FDA-approved treatment for AIC, in terms of preserving myocyte viability following an anthracycline challenge. It is thought that mitochondria-targeted RSSH treatment will rescue left ventricular (LV) function and improve the survival of DOX-treated subjects with effects that outweigh the impacts of currently used anti-AIC therapeutics. An ideal anti-AIC treatment also should also keep its efficacy against cancer cell growth.

3.2 Background and Preliminary Data

Anti-cancer therapies, such as anthracyclines like doxorubicin (DOX), are very effective against many malignancies, Hortobágyi, 1997, but they may lead to heart failure (HF). Yeh et al., 2009. Currently, there are no optimal strategies for preventing/managing anthracycline-induced cardiotoxicity (AIC). Cancer treatments have greatly improved patients' survival. Siegel et al., 2021; Miller et al., 2019. Yet, this comes with the growing social/economic cost of adverse cardiac effects, i.e., HF.

DOX cardiotoxicity mechanisms are complex and multifactorial. Excessive reactive oxygen species (ROS) are central to AIC. Singal and Iliskovic, 1998. This surge may emanate from at least three sources: (1) the continuous redox cycling of the DOX quinone moiety; Sawyer, 2013; (2) DOX-promoted chelation of free iron that, in turn, forms iron-DOX complexes interacting with $O_2$ to produce ROS; Gammella et al., 2014; and (3) the inhibition of topoisomerase 2β (Top2β) that is heavily expressed in cardiomyocytes, fueling ROS generation. Zhang et al., 2012. Cardiomyocytes are particularly vulnerable to ROS-mediated damage owing to lower constitutive levels of antioxidant enzymes. Moris et al., 2017.

Several antioxidants (mitochondrially or non-mitochondrially targeted) have shown encouraging results at the bench, but their impact against AIC remains quite limited when tested clinically. Vincent et al., 2013. Mitochondria retain the "memory" of redox and metabolic alterations well beyond the DOX in vivo half-life, Wallace et al., 2020, rendering cancer patients more sensitive to subsequent regimens of drug therapy. Thus, these organelles have long been considered a therapeutic target for this disorder. Antioxidants, including ascorbic acid, N-acetylcysteine, carvedilol, and coenzyme Q10, have shown promising results against DOX toxicity. Cadeddu et al., 2020. Furthermore, small molecules that specifically target mitochondrial dysfunction is a promising strategy to treat AIC. For example, mitochondria-targeted TEMPO shields murine and rat cardiomyocytes against DOX injury. Rocha et al., 2016. Moreover, it significantly attenuates contractile impairment and lipid peroxidation in DOX-treated rat hearts. Monti et al., 1996. Yet, there is no evidence whether antioxidants reduce the incidence of clinical heart failure among patients undergoing anthracycline-based chemotherapy without altering the anti-neoplastic anthracycline power. Vincent et al., 2013. The presently disclosed data suggest that RSSH donors can outweigh current approaches because they protect myocytes from DOX-induced oxidative damage and also maintain or even potentiate DOX anti-cancer effects.

Currently, dexrazoxane is the only FDA-approved drug for AIC; however, certain countries have banned its use in children. Dexrazoxane (DRZ), via its active metabolite, ADR-925, chelates $Fe^{3+}$, removing iron from the iron-DOX complexes; Sterba et al., 2013, this inhibits iron-mediated lipid peroxidation, and ATPase inactivation. Vile and Winterbourn, 1990. Furthermore, DRZ inhibits cell growth by binding and inactivating ATP-bound topoisomerase II. Classen et al., 2003. Despite its effectiveness, DRZ is not devoid of side effects, such as hematological toxicity, altered liver function, and pain. Langer, 2014. The European Medicines Agency (EMA) recommended DRZ not to be used in children or adolescents owing to the possible increased risk of acute myeloid leukemia and myelodysplastic syndrome. Langer, 2014.

Hydropersulfides (RSSH) represent an unprecedented opportunity to treat AIC. $H_2S$ has emerged as a cell-signaling molecule, joining nitric oxide (NO) and carbon monoxide (CO) as endogenous "gasotransmitters." $H_2S$ is a vasorelaxant, inhibits myocardial ischemia-reperfusion injury, and slows down atherosclerosis progression. Zhang et al., 2018. Yet, $H_2S$ protection mechanisms against DOX-induced toxicity remains poorly characterized. Du et al., 2018. Post-translational modifications of redox-active cysteines (Cys-SH) into cysteine hydropersulfides (Cys-SSH) are now appreciated as critical steps of $H_2S$ signaling. Filipovic et al., 2018. The direct reaction of $H_2S$ with protein cysteine residues, however, does not occur because $H_2S$ is unreactive with thiols in their reduced state. Instead, RSSH formation occurs via the reaction of $H_2S$ with oxidized thiols, e.g., disulfides (RSSR) or sulfenic acids (RSOH). Alternatively, sulfane sulfur species like RSSH and polysulfides can modify protein cysteine residues (P-SH), generating protein hydropersulfides (P-SSH). Accordingly, $H_2S$ biological effects are now ascribed substantially to RSSH. Filipovic et al., 2018; Fukuto et al., 2018; Fukuto et al., 2020. Recently, there has been great interest in the physiological functions of these sulfur species, including cytosolic Cys-SSH and glutathione persulfide (GSSH), and sulfhydration of protein cysteine residues, i.e., conversion of P-SH to P-SSH. RSSH are highly prevalent in mammalian tissues and fluids, Fukuto et al., 2018, conferring substantial protection against oxidative and/or electrophilic stress. Ida et al., 2014. Indeed, we have recently reported that RSSH counter ROS adverse impact on isolated myocytes/whole hearts after ischemia-reperfusion injury. Khodade et al., 2020. Notably, such evidence suggests that RSSH precursors potently afford protection against oxidative- and DOX-induced cell death. Khodade et al., 2020; Khodade et al., 2021a.

Explanations for RSSH effectiveness include 1) RSSH/$RSS^-$ are superior H-atom donors and reductants compared to RSH/RS"; Fukuto et al., 2020; Chauvin et al., 2017; Everett et al., 1994. 2) RSSH are markedly more nucleophilic and acidic than their RSH counterparts, conferring protection against toxic electrophilic metabolites; Benchoam et al., 2020. 3) RSSH in its neutral state is electrophilic (unlike RSH and $H_2S$) and may react with nucleophiles, including protein thiols (P-SH), resulting in P-SSH generation, which can provide protection against overoxidation; Álvarez et al., 2017; Untereiner et al., 2016, and perhaps-most importantly-4) RSSH may stimulate endogenous antioxidant defense pathways via activation of the transcription factor nuclear factor-erythroid factor 2-related factor 2 (Nrf2) by Kelch-like ECH-associated protein 1 (KEAP-1) thiol persulfidation and promote mitochondrial biogenesis and bioenergetics via persulfidation of peroxisome proliferator-activated receptor-gamma coactivator (PGC)-1α. Murphy et al., 2019; Akaike et al., 2017.

Different basal levels of reactive sulfur species may play a prominent role in maintaining DOX efficacy against cancer while preserving myocardial function. One unique challenge in cardio-oncology is to minimize cardiac adverse effects of anti-cancer drugs such as DOX without affecting their therapeutic efficacy. Tackling this issue demands a deeper understanding of the pathobiology of myocardial cells vs. cancer cells, particularly for their redox biology and content of $H_2S$-related moieties. Concerning endogenous $H_2S$ production in cancer cells and disease progression, elevated levels of $H_2S$-generating enzymes in human breast biopsies correlate well with their respective tumor proliferation indices. Youness et al., 2021; Li et al., 2021; Erdélyi et al., 2021.

Indeed, the presently disclosed data (FIG. 16) show a cytoprotective effect with exogenous RSSH regimen after DOX treatment of cardiac cells and significantly, a potentiated anti-cancer effect. Moreover, the presently disclosed data (FIG. 18) demonstrate orders of magnitude higher $H_2S$ and sulfane sulfur levels in cancer (MDA-MB-468, MCF-7, and HepG2) vs. cardiac (H9c2) cells. These measurements are the first of their kind and point to the role of reductive stress in the observed contrasting effects.

The presently disclosed subject matter is significant because 1) there is an urgent need for safer anti-AIC therapies, particularly in children, who unfortunately are a large cancer patient population requiring anthracycline treatment; 2) current antioxidant therapies are not devoid of primary toxic effects; and 3) these studies will contribute to a better understanding of AIC pathobiology, thus opening potential avenues for the treatment of this syndrome afflicting millions of people world-wide, encompassing RSSH donors and beyond.

Example 4

Treatment of COVID-19

It has been reported that sulforaphane, an isothiocyanate (R—N═C═S) prevalent in broccoli and the like, exhibits promising antiviral activity and may have promise as a treatment for COVID-19. Ordonez, A. A., Bullen, C. K., Villabona-Rueda, A. F. et al. Sulforaphane exhibits antiviral activity against pandemic SARS-COV-2 and seasonal HCoV-OC43 coronaviruses in vitro and in mice. Commun Biol 5, 242 (2022). See International PCT Patent Application No. PCT/US2022/014267 for Methods for inhibiting coronaviruses using sulforaphane to Jones-Brando et al., which is incorporate herein by reference in its entirety.

Much of the biological activity of sulforaphane has been attributed to the in vivo production of $H_2S$, and much of the biological activity of $H_2S$ is due to hydropersulfides. Accordingly, the presently disclosed RSSH donors can be used for the treatment of COVID-19.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents form part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Abeti, R., Baccaro, A., Esteras, N., and Giunti, P. (2018) Novel Nrf2-Inducer Prevents Mitochondrial Defects and Oxidative Stress in Friedreich's Ataxia Models. 12, 1-10.

Agrimi, J.; Spalletti, C.; Baroni, C.; Keceli, G.; Zhu, G.; Caragnano, A.; Matteucci, M.; Chelko, S.; Ramirez-Correa, G. A.; Bedja, D.; Casieri, V.; Di Lascio, N.; Scalco, A.; Beltrami, A. P.; Paolocci, N.; Caleo, M.; Lionetti, V., Obese mice exposed to psychosocial stress display cardiac and hippocampal dysfunction associated with local brain-derived neurotrophic factor depletion. EBioMedicine 2019, 47, 384-401.

Ahsan, M. K.; Lekli, I.; Ray, D.; Yodoi, J.; Das, D. K., Redox Regulation of Cell Survival by the Thioredoxin Superfamily: An Implication of Redox Gene Therapy in the Heart. Antioxid. Redox. Signal. 2009, 11 (11), 2741-2758.

Akaike, T.; Ida, T.; Wei, F.-Y.; Nishida, M.; Kumagai, Y.; Alam, M. M.; Ihara, H.; Sawa, T.; Matsunaga, T.; Kasamatsu, S.; Nishimura, A.; Morita, M.; Tomizawa, K.; Nishimura, A.; Watanabe, S.; Inaba, K.; Shima, H.; Tanuma, N.; Jung, M.; Fujii, S.; Watanabe, Y.; Ohmuraya, M.; Nagy, P.; Feelisch, M.; Fukuto, J. M.; Motohashi, H., Cysteinyl-tRNA synthetase governs cysteine polysulfidation and mitochondrial bioenergetics. Nat. Comm. 2017, 8 (1), 1177.

Alisik, M.; Neselioglu, S.; Erel, O., A colorimetric method to measure oxidized, reduced and total glutathione levels in erythrocytes. J. Lab. Med. 2019, 43 (5), 269-277.

Álvarez, L., C. L. Bianco, J. P. Toscano, J. Lin, T. Akaike and J. M. Fukuto, Antioxid. Redox Signal., 2017, 27, 622-633.

Amgalan, D.; Garner, T. P.; Pekson, R.; Jia, X. F.; Yanamandala, M.; Paulino, V.; Liang, F. G.; Corbalan, J. J.; Lee, J.; Chen, Y.; Karagiannis, G. S.; Sanchez, L. R.; Liang, H.; Narayanagari, S.-R.; Mitchell, K.; Lopez, A.; Margulets, V.; Scarlata, M.; Santulli, G.; Asnani, A.; Peterson, R. T.; Hazan, R. B.; Condeelis, J. S.; Oktay, M. H.; Steidl, U.; Kirshenbaum, L. A.; Gavathiotis, E.; Kitsis, R. N., A small-molecule allosteric inhibitor of BAX protects against doxorubicin-induced cardiomyopathy. Nat Cancer 2020, 1 (3), 315-328.

Apple, M. A.; Greenberg, D. M., Inhibitory effect of DL-2-mercapto-3-hydroxypropanal on growth of transplantable cancers in mice. Cancer chemotherapy reports 1969, 53 (3), 195-8.

Arkat, S.; Umbarkar, P.; Singh, S.; Sitasawad, S. L., Mitochondrial Peroxiredoxin-3 protects against hyperglycemia induced myocardial damage in Diabetic cardiomyopathy. Free Radic Biol Med. 2016, 97, 489-500.

Artaud, I., and E. Galardon, ChemBioChem, 2014, 15, 2361-2364.

Barr, L. A., and J. W. Calvert, Circ. J., 2014, 78, 2111-2118.

Benchoam, D., Cuevasanta, E., Möller, M. N., and Alvarez, B. (2019) Hydrogen Sulfide and Persulfides Oxidation by Biologically Relevant Oxidizing Species. Antioxidants. 10.3390/antiox8020048.

Benchoam, D.; Semelak, J. A.; Cuevasanta, E.; Mastrogiovanni, M.; Grassano, J. S.; Ferrer-Sueta, G.; Zeida, A.; Trujillo, M.; Möller, M. N.; Estrin, D. A.; Alvarez, B., Acidity and nucleophilic reactivity of glutathione persulfide. J. Biol. Chem. 2020, 295 (46), 15466-15481.

Bianco, C. L., T. Akaike, T. Ida, P. Nagy, V. Bogdandi, J. P. Toscano, Y. Kumagai, C. F. Henderson, R. N. Goddu, J. Lin and J. M. Fukuto, Br. J. Pharmacol., 2019, 176, 671-683.

Bora, P., P. Chauhan, S. Manna and H. Chakrapani, Org. Lett., 2018, 20, 7916-7920.

Brois, S., J. F. Pilot and H. W. Barnum, J. Am. Chem. Soc., 1970, 92, 7629-7631.

Cadeddu Dessalvi, C.; Deidda, M.; Noto, A.; Madeddu, C.; Cugusi, L.; Santoro, C.; López-Fernández, T.; Galderisi, M.; Mercuro, G., Antioxidant Approach as a Cardioprotective Strategy in Chemotherapy-Induced Cardiotoxicity. Antioxid. Redox Signal. 2020, 34 (7), 572-588.

Cai, K., Tonelli, M., Frederick, R. O., and Markley, J. L. (2017) Human Mitochondrial Ferredoxin 1 (FDX1) and Ferredoxin 2 (FDX2) Both Bind Cysteine Desulfurase and Donate Electrons for Iron-Sulfur Cluster Biosynthesis. Biochemistry. 56, 487-499.

Campuzano, V., Montermini, L., Molto, M. D., Pianese, L., Cossee, M., Cavalcanti, F., Monros, E., Duclos, F., Monticelli, A., Zara, F., Cafiizares, J., Koutnikova, H., Bidichandani, S. I., Gellera, C., Brice, A., Trouillas, P., Michele, G. De, Filla, A., Frutos, R. De, Patel, P. I., Donato, S. Di, Mandel, J., Cocozza, S., Koenig, M., and Pandolfol, M. (1996) Friedreich's Ataxia: Autosomal Recessive Disease Caused by an Intronic GAA Triplet Repeat Expansion. Science. 271, 1423-1427.

Chaudhuri, A., Y. Venkatesh, J. Das, M. Gangopadhyay, T. K. Maiti and N. D. P. Singh, J. Org. Chem., 2019, 84, 11441-11449.

Chauvin, J.-P. R.; Griesser, M.; Pratt, D. A., Hydropersulfides: H-Atom Transfer Agents Par Excellence. J. Am. Chem. Soc. 2017, 139 (18), 6484-6493.

Chelko, S. P.; Keceli, G.; Carpi, A.; Doti, N.; Agrimi, J.; Asimaki, A.; Beti, C. B.; Miyamoto, M.; Amat-Codina, N.; Bedja, D.; Wei, A.-C.; Murray, B.; Tichnell, C.; Kwon, C.; Calkins, H.; James, C. A.; O'Rourke, B.; Halushka, M. K.; Melloni, E.; Saffitz, J. E.; Judge, D. P.; Ruvo, M.; Kitsis, R. N.; Andersen, P.; Di Lisa, F.; Paolocci, N., Exercise triggers CAPN1-mediated AIF truncation, inducing myocyte cell death in arrhythmogenic cardiomyopathy. Sci Transl Med. 2021, 13 (581), eabf0891.

Chen, W., C. Liu, B. Peng, Y. Zhao, A. Pacheco and M. Xian, Chem. Sci., 2013, 4, 2892-2896.

Chen, X.-L.; Dodd, G.; Thomas, S.; Zhang, X.; Wasserman, M. A.; Rovin, B. H.; Kunsch, C., Activation of Nrf2/ARE pathway protects endothelial cells from oxidant injury and inhibits inflammatory gene expression. Am. J. Physiol. Heart Circ. Physiol. 2006, 290 (5), H1862-H1870.

Chengelis, C. P. and R. A. Neal, Toxicol. Appl. Pharmacol., 1980, 55, 198-202.

Classen, S.; Olland, S.; Berger, J. M., Structure of the topoisomerase II ATPase region and its mechanism of inhibition by the chemotherapeutic agent ICRF-187 Proc. Natl. Acad. Sci. U.S.A. 2003, 100 (19), 10629-10634.

Cline, M. R.; Tu, C.; Silverman, D. N.; Toscano, J. P., Detection of nitroxyl (HNO) by membrane inlet mass spectrometry. Free Radical Biol. Med. 2011, 50 (10), 1274-1279.

Cuevasanta, E., M. Lange, J. Bonanata, E. L. Coitiño, G. Ferrer-Sueta, M. R. Filipovic and B. Alvarez, J. Biol. Chem., 2015, 290, 26866-26880.

D'Oria, R., R. Schipani, A. Leonardini, A. Natalicchio, S. Perrini, A. Cignarelli, L. Laviola and F. Giorgino, Oxid. Med. Cell. Longev., 2020, 2020, 5732956.

Dallons, M.; Schepkens, C.; Dupuis, A.; Tagliatti, V.; Colet, J.-M., New Insights About Doxorubicin-Induced Toxicity to Cardiomyoblast-Derived H9C2 Cells and Dexrazoxane Cytoprotective Effect: Contribution of In Vitro1H-NMR Metabonomics. Front. Pharmacol. 2020, 11.

Dhalla, N. S., R. M. Temsah and T. Netticadan, J. Hypertens., 2000, 18.

Dhanasekaran, S.; Venugopal, D.; Al-Dayan, N.; Ravinayagam, V.; Mohammed, A. A., Emerging insights into mitochondria-specific targeting and drug delivering strategies: Recent milestones and therapeutic implications. Saudi J. Biol. Sci. 2020, 27 (12), 3581-3592.

Di Prospero, N. A., Baker, A., Jeffries, N., and Fischbeck, K. H. (2007) Neurological effects of high-dose idebenone in patients with Friedreich's ataxia: a randomised, placebo-controlled trial. Lancet Neurol. 6, 878-886.

Dikalov, S.; Itani, H.; Richmond, B.; Arslanbaeva, L.; Vergeade, A.; Rahman, S. M. J.; Boutaud, O.; Blackwell, T.; Massion, P. P.; Harrison, D. G.; Dikalova, A., Tobacco smoking induces cardiovascular mitochondrial oxidative stress, promotes endothelial dysfunction, and enhances hypertension. Am J Physiol Heart Circ Physiol. 2019, 316 (3), H639-H646.

Dillon, K. M.; Carrazzone, R. J.; Wang, Y.; Powell, C. R.; Matson, J. B., Polymeric Persulfide Prodrugs: Mitigating Oxidative Stress through Controlled Delivery of Reactive Sulfur Species. ACS Macro Lett. 2020, 9 (4), 606-612.

Dillon, K. M.; Matson, J. B., A Review of Chemical Tools for Studying Small Molecule Persulfides: Detection and Delivery. ACS Chem. Biol. 2021, 16 (7), 1128-1141.

Dinkova-Kostova, A. T.; Talalay, P., NAD(P)H:quinone acceptor oxidoreductase 1 (NQO1), a multifunctional antioxidant enzyme and exceptionally versatile cytoprotector. Arch. Biochem. Biophys. 2010, 501 (1), 116-123.

Dixon, S. J., Lemberg, K. M., Lamprecht, M. R., Skouta, R., Zaitsev, E. M., Gleason, C. E., Patel, D. N., Bauer, A. J., Cantley, A. M., Yang, W. S., Morrison, B., and Stockwell, B. R. (2012) Ferroptosis: An Iron-Dependent Form of Nonapoptotic Cell Death. Cell. 149, 1060-1072.

Dóka, É., I. Pader, A. Bíró, K. Johansson, Q. Cheng, K. Ballagó, J. R. Prigge, D. Pastor-Flores, T. P. Dick, E. E. Schmidt, E. S. J. Arnér and P. Nagy, Sci. Adv., 2016, 2, e1500968.

Dóka, É., Ida, T., Dagnell, M., Abiko, Y., Luong, N. C., Balog, N., Takata, T., Espinosa, B., Nishimura, A., Cheng, Q., Funato, Y., Miki, H., Fukuto, J. M., Prigge, J. R., Schmidt, E. E., Arnér, E. S. J., Kumagai, Y., Akaike, T., and Nagy, P. (2020) Control of protein function through oxidation and reduction of persulfidated states. Sci. Adv. 6, eaax8358.

Du, S.; Huang, Y.; Jin, H.; Wang, T., Protective Mechanism of Hydrogen Sulfide against Chemotherapy-Induced Cardiotoxicity. Front. Pharmacol. 2018, 9 (32).

Dürr, A., Cossee, M., Agid, Y., Campuzano, V., Mignard, C., Penet, C., Mandel, J.-L., Brice, A., and Koenig, M. (1996) Clinical and Genetic Abnormalities in Patients with Friedreich's Ataxia. N. Engl. J. Med. 335, 1169-1175.

Erdélyi, K.; Ditrói, T.; Johansson, H. J.; Czikora, Á.; Balog, N.; Silwal-Pandit, L.; Ida, T.; Olasz, J.; Hajdú, D.; Mátrai, Z.; Csuka, O.; Uchida, K.; Tóvári, J.; Engebraten, O.; Akaike, T.; Dale, A.-L. B.; Kásler, M.; Lehtiö, J.; Nagy, P., Reprogrammed transsulfuration promotes basal-like breast tumor progression via realigning cellular cysteine persulfidation. Proc. Natl. Acad. Sci. U.S.A. 2021, 118 (45), e2100050118.

Everett, S. A.; Folkes, L. K.; Wardman, P.; Asmus, K. D., Free-Radical Repair by a Novel Perthiol: Reversible Hydrogen Transfer and Perthiyl Radical Formation. Free Radic Res. 1994, 20 (6), 387-400.

Feng, H., Schorpp, K., Jin, J., Yozwiak, C. E., Hoffstrom, B. G., Decker, A. M., Rajbhandari, P., Stokes, M. E., Bender, H. G., Csuka, J. M., Upadhyayula, P. S., Canoll, P., Uchida, K., Soni, R. K., Hadian, K., and Stockwell, B. R. (2020) Transferrin Receptor Is a Specific Ferroptosis Marker. Cell Rep. 30, 3411-3423.e7.

Feng, N.; Huke, S.; Zhu, G.; Tocchetti, C. G.; Shi, S.; Aiba, T.; Kaludercic, N.; Hoover, D. B.; Beck, S. E.; Mankowski, J. L.; Tomaselli, G. F.; Bers, D. M.; Kass, D. A.; Paolocci, N., Constitutive BDNF/TrkB signaling is required for normal cardiac contraction and relaxation. Proc Natl Acad Sci USA. 2015, 112 (6), 1880-1885.

Filipovic, M. R.; Zivanovic, J.; Alvarez, B.; Banerjee, R., Chemical Biology of H2S Signaling through Persulfidation. Chem. Rev. 2018, 118 (3), 1253-1337.

Freibert, S.-A., Boniecki, M. T., Stumpfig, C., Schulz, V., Krapoth, N., Winge, D. R., Mühlenhoff, U., Stehling, O., Cygler, M., and Lill, R. (2021) N-terminal tyrosine of ISCU2 triggers [2Fe-2S] cluster synthesis by ISCU2 dimerization. Nat. Commun. 12, 6902.

Fukuto, J. M.; Hobbs, A. J., A comparison of the chemical biology of hydropersulfides (RSSH) with other protective biological antioxidants and nucleophiles. Nitric Oxide 2021, 107, 46-57.

Fukuto, J. M.; Ignarro, L. J.; Nagy, P.; Wink, D. A.; Kevil, C. G.; Feelisch, M.; Cortese-Krott, M. M.; Bianco, C. L.; Kumagai, Y.; Hobbs, A. J.; Lin, J.; Ida, T.; Akaike, T., Biological hydropersulfides and related polysulfides—a new concept and perspective in redox biology. FEBS Lett. 2018, 592 (12), 2140-2152.

Fukuto, J. M.; Lin, J.; Khodade, V. S.; Toscano, J. P., Predicting the Possible Physiological/Biological Utility of the Hydropersulfide Functional Group Based on Its Chemistry: Similarities Between Hydropersulfides and Selenols. Antioxid. Redox Signal. 2020, 33 (18), 1295-1307.

Gadalla, M. M., and Snyder, S. H. (2010) Hydrogen sulfide as a gasotransmitter. J. Neurochem. 113, 14-26.

Gammella, E.; Maccarinelli, F.; Buratti, P.; Recalcati, S.; Cairo, G., The role of iron in anthracycline cardiotoxicity. Front. Pharmacol. 2014, 5 (25).

Gao, K.; Chi, Y.; Sun, W.; Takeda, M.; Yao, J., 5'-AMP-Activated Protein Kinase Attenuates Adriamycin-Induced Oxidative Podocyte Injury through Thioredoxin-Mediated Suppression of the Apoptosis Signal-Regulating Kinase 1-P38 Signaling Pathway. Mol. Pharmacol. 2014, 85 (3), 460-471.

Gervason, S., Larkem, D., Mansour, A. Ben, Botzanowski, T., Müller, C. S., Pecqueur, L., Le Pavec, G., Delaunay-Moisan, A., Brun, O., Agramunt, J., Grandas, A., Fontecave, M., Schünemann, V., Cianférani, S., Sizun, C., Tolédano, M. B., and D'Autréaux, B. (2019) Physiologically relevant reconstitution of iron-sulfur cluster biosynthesis uncovers persulfide-processing functions of ferredoxin-2 and frataxin. Nat. Commun. 10, 3566.

Gottesfeld, J. M. (2007) Small molecules affecting transcription in Friedreich ataxia. Pharmacol. Ther. 116, 236-248.

Greiner, R., Z. Pálinkás, K. Bäsell, D. Becher, H. Antelmann, P. Nagy and T. P. Dick, Antioxid. Redox Signal., 2013, 19, 1749-1765.

Gureev, A. P.; Shaforostova, E. A.; Popov, V. N., Regulation of Mitochondrial Biogenesis as a Way for Active Longevity: Interaction Between the Nrf2 and PGC-1α Signaling Pathways. Front. Genet. 2019, 10, 435-435.

Harpp D. N., and A. Granata, J. Org. Chem., 1979, 44, 4144-4148.

Harpp, D. N., and A. Granata, Tetrahedron Lett., 1976, 17, 3001-3004.

Hart, P. E., Lodi, R., Rajagopalan, B., Bradley, J. L., Crilley, J. G., Turner, C., Blamire, A. M., Manners, D., Styles, P., Schapira, A. H. V, and Cooper, J. M. (2005) Antioxidant Treatment of Patients With Friedreich Ataxia: Four-Year Follow-up. Arch. Neurol. 62, 621-626.

Hayden, M. R.; Goldsmith, D. J. A., Sodium Thiosulfate: New Hope for the Treatment of Calciphylaxis. Semin. Dial. 2010, 23 (3), 258-262.

Hoch, G. and B. Kok, Arch. Biochem. Biophys., 1963, 101, 160-170.

Hofgaard, J. P., K. S. Sigurdardottir and M. Treiman, Pharmacol. Res., 2006, 54, 303-310.

Hortobágyi, G. N., Anthracyclines in the Treatment of Cancer. Drugs 1997, 54 (4), 1-7.

Hull, T. D.; Boddu, R.; Guo, L.; Tisher, C. C.; Traylor, A. M.; Patel, B.; Joseph, R.; Prabhu, S. D.; Suliman, H. B.; Piantadosi, C. A.; Agarwal, A.; George, J. F., Heme oxygenase-1 regulates mitochondrial quality control in the heart. JCI Insight 2016, 1 (2).

Hybertson, B. M., Gao, B., Bose, S. K., and McCord, J. M. (2011) Oxidative stress in health and disease: The therapeutic potential of Nrf2 activation. Mol. Aspects Med. 32, 234-246.

Ibrahim, N. E.; Januzzi, J. L., Established and Emerging Roles of Biomarkers in Heart Failure. Circ. Res. 2018, 123 (5), 614-629.

Iciek, M.; Bilska-Wilkosz, A.; Górny, M., Sulfane sulfur-new findings on an old topic. Acta biochimica Polonica 2019, 66 (4), 533-544.

Ida, T.; Sawa, T.; Ihara, H.; Tsuchiya, Y.; Watanabe, Y.; Kumagai, Y.; Suematsu, M.; Motohashi, H.; Fujii, S.; Matsunaga, T.; Yamamoto, M.; Ono, K.; Devarie-Baez, N. O.; Xian, M.; Fukuto, J. M.; Akaike, T., Reactive cysteine persulfides and S-polythiolation regulate oxidative stress and redox signaling. Proc. Natl. Acad. Sci. USA 2014, 111 (21), 7606-7611.

Ishiyama, M.; Miyazono, Y.; Sasamoto, K.; Ohkura, Y.; Ueno, K., A highly water-soluble disulfonated tetrazolium salt as a chromogenic indicator for NADH as well as cell viability. Talanta 1997, 44 (7), 1299-1305.

Jiang, L.; Gong, Y.; Hu, Y.; You, Y.; Wang, J.; Zhang, Z.; Wei, Z.; Tang, C., Peroxiredoxin-1 Overexpression Attenuates Doxorubicin-Induced Cardiotoxicity by Inhibiting Oxidative Stress and Cardiomyocyte Apoptosis. Oxid. Med. Cell. Longev. 2020, 2020, 2405135.

Johnson, D. C., Dean, D. R., Smith, A. D., and Johnson, M. K. (2005) Structure, function, and formation of biological iron-sulfur clusters. Annu. Rev. Biochem. 74, 247-281.

Jones, L. J.; Singer, V. L., Fluorescence Microplate-Based Assay for Tumor Necrosis Factor Activity Using SYTOX Green Stain. Anal Biochem. 2001, 293 (1), 8-15.

Kaludercic N, Carpi A, Nagayama T, Sivakumaran V, Zhu G, Lai E W, Bedja D, De Mario A, Chen K, Gabrielson K L, Lindsey M L, Pacak K, Takimoto E, Shih J C, Kass D A, Di Lisa F, Paolocci N. Monoamine oxidase B prompts mitochondrial and cardiac dysfunction in pressure overloaded hearts. Antioxid Redox Signal. 2014 Jan. 10; 20(2):267-80.

Kang, J., S. Xu, M. N. Radford, W. Zhang, S. S. Kelly, J. J. Day and M. Xian, Angew. Chem. Int. Ed., 2018, 57, 5893-5897.

Kasamatsu, S., A. Nishimura, M. Morita, T. Matsunaga, H. Abdul Hamid and T. Akaike, Molecules, 2016, 21.

Kaspar, J. W., Niture, S. K., and Jaiswal, A. K. (2009) Nrf2: INrf2 (Keap1) signaling in oxidative stress. Free Radic. Biol. Med. 47, 1304-1309.

Khodade, V. S.; Aggarwal, S. C.; Eremiev, A.; Bao, E.; Porche, S.; Toscano, J. P., Development of Hydropersulfide Donors to Study Their Chemical Biology. Antioxid. Redox Signal. 2021b, 36 (4-6), 309-326.

Khodade, V. S.; Aggarwal, S. C.; Pharoah, B. M.; Paolocci, N.; Toscano, J. P., Alkylsulfenyl thiocarbonates: precursors to hydropersulfides potently attenuate oxidative stress. Chem. Sci. 2021a, 12 (23), 8252-8259.

Khodade, V. S.; Pharoah, B. M.; Paolocci, N.; Toscano, J. P., Alkylamine-Substituted Perthiocarbamates: Dual Precursors to Hydropersulfide and Carbonyl Sulfide with Cardioprotective Actions. J. Am. Chem. Soc. 2020, 142 (9), 4309-4316.

Khodade, V. S.; Toscano, J. P., Development of S-Substituted Thioisothioureas as Efficient Hydropersulfide Precursors. J. Am. Chem. Soc. 2018, 140 (50), 17333-17337.

Kimura, H., Molecules, 2014, 19, 16146-16157.

Koike, S.; Nishimoto, S.; Ogasawara, Y., Cysteine persulfides and polysulfides produced by exchange reactions with H2S protect SH-SY5Y cells from methylglyoxal-induced toxicity through Nrf2 activation. Redox Biol. 2017, 12, 530-539.

Kolluru, G. K.; Shen, X.; Kevil, C. G., Reactive Sulfur Species. Arterioscler. Thromb. Vasc. Biol. 2020, 40 (4), 874-884.

Kulkarni, C. A.; Fink, B. D.; Gibbs, B. E.; Chheda, P. R.; Wu, M.; Sivitz, W. I.; Kerns, R. J., A Novel Triphenylphosphonium Carrier to Target Mitochondria without Uncoupling Oxidative Phosphorylation. J. Med. Chem. 2021, 64 (1), 662-676.

Kunikata, H., T. Ida, K. Sato, N. Aizawa, T. Sawa, H. Tawarayama, N. Murayama, S. Fujii, T. Akaike and T. Nakazawa, Sci. Rep., 2017, 7, 41984.

Kurdi, M.; Sivakumaran, V.; Duhé, R. J.; Aon, M. A.; Paolocci, N.; Booz, G. W., Depletion of cellular glutathione modulates LIF-induced JAK1-STAT3 signaling in cardiac myocytes. Int J Biochem Cell Biol. 2012, 44 (12), 2106-2115.

Lagoa, R.; Gañán, C.; López-Sánchez, C.; García-Martínez, V.; Gutierrez-Merino, C., The decrease of NAD(P)H: quinone oxidoreductase 1 activity and increase of ROS production by NADPH oxidases are early biomarkers in doxorubicin cardiotoxicity. Biomarkers 2014, 19 (2), 142-153.

Langer, S. W., Dexrazoxane for the treatment of chemotherapy-related side effects. Cancer Manag. Res. 2014, 6, 357-363.

Lazo, M.; Rubin, J.; Clark, J. M.; Coresh, J.; Schneider, A. L.; Ndumele, C.; Hoogeveen, R. C.; Ballantyne, C. M.; Selvin, E., The association of liver enzymes with biomarkers of subclinical myocardial damage and structural heart disease. Journal of hepatology 2015, 62 (4), 841-7.

Leininger, K. R.; Westley, J., The Mechanism of the Rhodanese-catalyzed Thiosulfate-Cyanide Reaction: THERMODYNAMIC AND ACTIVATION PARAMETERS. J. Biol. Chem. 1968, 243 (8), 1892-1899.

Li, H.; Mani, S.; Wu, L.; Fu, M.; Shuang, T.; Xu, C.; Wang, R., The interaction of estrogen and CSE/H2S pathway in the development of atherosclerosis. Am. J. Physiol. Heart Circ. Physiol. 2017, 312 (3), H406-H414.

Li, M.; Liu, Y.; Deng, Y.; Pan, L.; Fu, H.; Han, X.; Li, Y.; Shi, H.; Wang, T., Therapeutic potential of endogenous hydrogen sulfide inhibition in breast cancer (Review). Oncol Rep 2021, 45 (5), 68.

Libiad, M.; Sriraman, A.; Banerjee, R., Polymorphic Variants of Human Rhodanese Exhibit Differences in Thermal Stability and Sulfur Transfer Kinetics*. J. Biol. Chem. 2015, 290 (39), 23579-23588.

Libiad, M.; Yadav, P. K.; Vitvitsky, V.; Martinov, M.; Banerjee, R., Organization of the Human Mitochondrial Hydrogen Sulfide Oxidation Pathway*♦. J. Biol. Chem. 2014, 289 (45), 30901-30910.

Lill, R., and Mühlenhoff, U. (2008) Maturation of Iron-Sulfur Proteins in Eukaryotes: Mechanisms, Connected Processes, and Diseases. Annu. Rev. Biochem. 77, 669-700.

Liu, C.; Zhang, F.; Munske, G.; Zhang, H.; Xian, M., Isotope dilution mass spectrometry for the quantification of sulfane sulfurs. Free Radic. Biol. Med. 2014, 76, 200-207.

Liu, W.; Porter, N. A.; Schneider, C.; Brash, A. R.; Yin, H., Formation of 4-hydroxynonenal from cardiolipin oxidation: Intramolecular peroxyl radical addition and decomposition. Free Radic Biol Med. 2011, 50 (1), 166-178.

Longen, S., F. Richter, Y. Köhler, I. Wittig, K.-F. Beck and J. Pfeilschifter, Sci. Rep., 2016, 6, 29808.

Lupoli, F., Vannocci, T., Longo, G., Niccolai, N., and Pastore, A. (2018) The role of oxidative stress in Friedreich's ataxia. FEBS Lett. 592, 718-727.

Manford, A. G.; Mena, E. L.; Shih, K. Y.; Gee, C. L.; McMinimy, R.; Martínez-González, B.; Sherriff, R.; Lew, B.; Zoltek, M.; Rodríguez-Pérez, F.; Woldesenbet, M.; Kuriyan, J.; Rape, M., Structural basis and regulation of the reductive stress response. Cell 2021, 184 (21), 5375-5390.e16.

Manford, A. G.; Rodríguez-Pérez, F.; Shih, K. Y.; Shi, Z.; Berdan, C. A.; Choe, M.; Titov, D. V.; Nomura, D. K.; Rape, M., A Cellular Mechanism to Detect and Alleviate Reductive Stress. Cell 2020, 183 (1), 46-61.e21.

Martinez, A. M., Kim, A., and Yang, W. S. (2020) Detection of Ferroptosis by BODIPY™ 581/591 C11. in Immune Mediators in Cancer: Methods and Protocols (Vancurova, I., and Zhu, Y. eds), pp. 125-130, Springer US, New York, NY, 10.1007/978-1-0716-0247-8_11.

Marutani, E., M. Sakaguchi, W. Chen, K. Sasakura, J. Liu, M. Xian, K. Hanaoka, T. Nagano and F. Ichinose, MedChemComm, 2014, 5, 1577-1583.

Meiners, B.; Shenoy, C.; Zordoky, B. N., Clinical and preclinical evidence of sex-related differences in anthracycline-induced cardiotoxicity. Biol Sex Differ. 2018, 9 (1), 38-38.

Miller, K. D.; Nogueira, L.; Mariotto, A. B.; Rowland, J. H.; Yabroff, K. R.; Alfano, C. M.; Jemal, A.; Kramer, J. L.; Siegel, R. L., Cancer treatment and survivorship statistics, 2019. CA Cancer J Clin. 2019, 69 (5), 363-385.

Mizuta, Y.; Tokuda, K.; Guo, J.; Zhang, S.; Narahara, S.; Kawano, T.; Murata, M.; Yamaura, K.; Hoka, S.; Hashizume, M.; Akahoshi, T., Sodium thiosulfate prevents doxorubicin-induced DNA damage and apoptosis in cardiomyocytes in mice. Life Sci. 2020, 257, 118074.

Monti, E.; Cova, D.; Guido, E.; Morelli, R.; Oliva, C., Protective effect of the nitroxide tempol against the cardiotoxicity of adriamycin. Free Radic. Biol. Med. 1996, 21 (4), 463-470.

Moris, D.; Spartalis, M.; Tzatzaki, E.; Spartalis, E.; Karachaliou, G.-S.; Triantafyllis, A. S.; Karaolanis, G. I.; Tsilimigras, D. I.; Theocharis, S., The role of reactive oxygen species in myocardial redox signaling and regulation. Ann Transl Med. 2017, 5 (16), 6.

Murphy, B.; Bhattacharya, R.; Mukherjee, P., Hydrogen sulfide signaling in mitochondria and disease. FASEB J 2019, 33 (12), 13098-13125.

Murphy, M. P., Targeting lipophilic cations to mitochondria. Annu. Rev. Pharmacol. Toxicol. 2008, 1777 (7), 1028-1031.

Murphy, M. P.; Hartley, R. C., Mitochondria as a therapeutic target for common pathologies. Nat. Rev. Drug. Discov. 2018, 17 (12), 865-886.

Murphy, M. P.; Smith, R. A. J., Targeting Antioxidants to Mitochondria by Conjugation to Lipophilic Cations. Annu. Rev. Pharmacol. Toxicol. 2007, 47 (1), 629-656.

Mustafa, A. K., Gadalla, M. M., Sen, N., Kim, S., Mu, W., Gazi, S. K., Barrow, R. K., Yang, G., Wang, R., and Snyder, S. H. (2009) H2S signals through protein S-sulfhydration. Sci. Signal. 2, ra72.

Nina Kaludercic, A. C., Takahiro Nagayama, Vidhya Sivakumaran, Guangshuo Zhu, Edwin W. Lai, Djahida Bedja, Agnese De Mario, Kevin Chen, Kathleen L. Gabrielson, Merry L. Lindsey, Karel Pacak, Eiki Takimoto, Jean C. Shih, David A. Kass, Fabio Di Lisa, and Nazareno Paolocci, Monoamine Oxidase B Prompts Mitochondrial and Cardiac Dysfunction in Pressure Overloaded Hearts. Antioxid Redox Signal. 2014, 20 (2), 267-280.

Ocana-Santero, G., Díaz-Nido, J., and Herranz-Martín, S. (2021) Future Prospects of Gene Therapy for Friedreich's Ataxia. Int. J. Mol. Sci. 10.3390/ijms22041815.

Ohwada, W.; Tanno, M.; Yano, T.; Ong, S.-B.; Abe, K.; Sato, T.; Kuno, A.; Miki, T.; Sugawara, H.; Igaki, Y.; Miura, T., Distinct intra-mitochondrial localizations of pro-survival kinases and regulation of their functions by DUSP5 and PHLPP-1. Biochim Biophys Acta Mol Basis Dis. 2020, 1866 (10), 165851.

Pan, J. and K. S. Carroll, ACS Chem. Biol., 2013, 8, 1110-1116.

Pandey, A., Gordon, D. M., Pain, J., Stemmler, T. L., Dancis, A., and Pain, D. (2013) Desulfurase by Exposing Substrate-binding Sites, and a Mutant Fe—S Cluster Scaffold Protein with Frataxin-bypassing Ability Acts Similarly*. J. Biol. Chem. 288, 36773-36786.

Pandolfo, M. (1999) Friedreich's ataxia: Clinical aspects and pathogenesis. Semin. Neurol. 19, 311-322.

Pandolfo, M. (2009) Friedreich ataxia: The clinical picture. J. Neurol. 256, 3-8

Paradies, G.; Paradies, V.; Ruggiero, F. M.; Petrosillo, G., Role of Cardiolipin in Mitochondrial Function and Dynamics in Health and Disease: Molecular and Pharmacological Aspects. Cells 2019, 8 (7), 728.

Park, C.-M., Weerasinghe, L., Day, J. J., Fukuto, J. M., and Xian, M. (2015) Persulfides: current knowledge and challenges in chemistry and chemical biology. Mol. BioSyst. 11, 1775-1785.

Park, C.-M.; Macinkovic, I.; Filipovic, M. R.; Xian, M., Chapter Three-Use of the "Tag-Switch" Method for the Detection of Protein S-Sulfhydration. In Meth. Enzymol., Cadenas, E.; Packer, L., Eds. Academic Press: 2015; Vol. 555, pp 39-56.

Park, E., and Chung, S. W. (2019) ROS-mediated autophagy increases intracellular iron levels and ferroptosis by ferritin and transferrin receptor regulation. Cell Death Dis. 10, 822.

Patra, S., and Barondeau, D. P. (2019) Mechanism of activation of the human cysteine desulfurase complex by frataxin. Proc. Natl. Acad. Sci. 116, 19421-19430.

Pereira, G. C.; Pereira, S. P.; Tavares, L. C.; Carvalho, F. S.; Magalhães-Novais, S.; Barbosa, I. A.; Santos, M. S.; Bjork, J.; Moreno, A. J.; Wallace, K. B.; Oliveira, P. J., Cardiac cytochrome c and cardiolipin depletion during anthracycline-induced chronic depression of mitochondrial function. Mitochondrion 2016, 30, 95-104.

Perez, C.; Daniel, K. B.; Cohen, S. M., Evaluating Prodrug Strategies for Esterase-Triggered Release of Alcohols. ChemMedChem 2013, 8 (10), 1662-1667.

Powell, C. R., K. M. Dillon, Y. Wang, R. J. Carrazzone and J. B. Matson, Angew. Chem. Int. Ed., 2018, 57, 6324-6328.

Puglisi, R., and Pastore, A. (2018) The role of chaperones in iron-sulfur cluster biogenesis. 592, 4011-4019.

Ravindran, S.; Boovarahan, S. R.; Shanmugam, K.; Vedarathinam, R. C.; Kurian, G. A., Sodium Thiosulfate Preconditioning Ameliorates Ischemia/Reperfusion Injury in Rat Hearts Via Reduction of Oxidative Stress and Apoptosis. Cardiovasc. Drugs Ther. 2017, 31 (5), 511-524.

Reichardt, P.; Tabone, M.-D.; Mora, J.; Morland, B.; Jones, R. L., Risk-benefit of dexrazoxane for preventing anthracycline-related cardiotoxicity: re-evaluating the European labeling. Future Oncol. 2018, 14 (25), 2663-2676.

Rocha, V. C. J.; França, L. S. d. A.; de Araújo, C. F.; Ng, A. M.; de Andrade, C. M.; Andrade, A. C.; Santos, E. d. S.; Borges-Silva, M. d. C.; Macambira, S. G.; Noronha-Dutra, A. A.; Pontes-de-Carvalho, L. C., Protective effects of mito-TEMPO against doxorubicin cardiotoxicity in mice. Cancer Chemother. Pharmacol. 2016, 77 (3), 659-662.

Rötig, A., de Lonlay, P., Chretien, D., Foury, F., Koenig, M., Sidi, D., Munnich, A., and Rustin, P. (1997) Aconitase and mitochondrial iron-sulphur protein deficiency in Friedreich ataxia. Nat. Genet. 17, 215-217.

Rouault, T. A. (2019) The indispensable role of mammalian iron sulfur proteins in function and regulation of multiple diverse metabolic pathways. BioMetals. 32, 343-353.

Rouault, T. A., and Maio, N. (2017) Biogenesis and functions of mammalian iron-sulfur proteins in the regulation of iron homeostasis and pivotal metabolic pathways. J. Biol. Chem. 292, 12744-12753.

Rouault, T. A., and Tong, W. H. (2008) Iron-sulfur cluster biogenesis and human disease. Trends Genet. 24, 398-407.

Sawyer, D. B., Anthracyclines and Heart Failure. N. Engl. J. Med. 2013, 368 (12), 1154-1156.

Shi, W.; Deng, H.; Zhang, J.; Zhang, Y.; Zhang, X.; Cui, G., Mitochondria-Targeting Small Molecules Effectively Prevent Cardiotoxicity Induced by Doxorubicin. Molecules 2018, 23 (6).

Shi, Y., Ghosh, M., Kovtunovych, G., Crooks, D. R., and Rouault, T. A. (2012) Both human ferredoxins 1 and 2 and ferredoxin reductase are important for iron-sulfur cluster biogenesis. Biochim. Biophys. Acta-Mol. Cell Res. 1823, 484-492.

Shioji, K.; Kishimoto, C.; Nakamura, H.; Masutani, H.; Yuan, Z.; Oka, S.-i.; Yodoi, J., Overexpression of Thioredoxin-1 in Transgenic Mice Attenuates Adriamycin-Induced Cardiotoxicity. Circulation 2002, 106 (11), 1403-1409.

Siegel, R. L.; Miller, K. D.; Fuchs, H. E.; Jemal, A., Cancer Statistics, 2021. CA Cancer J Clin. 2021, 71 (1), 7-33.

Singal, P. K.; Iliskovic, N., Doxorubicin-Induced Cardiomyopathy. N. Engl. J. Med. 1998, 339 (13), 900-905.

Sourris, K. C.; Harcourt, B. E.; Tang, P. H.; Morley, A. L.; Huynh, K.; Penfold, S. A.; Coughlan, M. T.; Cooper, M. E.; Nguyen, T.-V.; Ritchie, R. H.; Forbes, J. M., Ubiquinone (coenzyme Q10) prevents renal mitochondrial dysfunction in an experimental model of type 2 diabetes. Free Radic Biol Med. 2012, 52 (3), 716-723.

Stěrba, M.; Popelová, O.; Vávrová, A.; Jirkovský, E.; Kovaříková, P.; Geršl, V.; Simůnek, T., Oxidative stress, redox signaling, and metal chelation in anthracycline cardiotoxicity and pharmacological cardioprotection. Antioxid. Redox Signaling 2013, 18 (8), 899-929.

Sui, Y.-B.; Zhang, K.-K.; Ren, Y.-k.; Liu, L.; Liu, Y., The role of Nrf2 in astragaloside IV-mediated antioxidative protection on heart failure. Pharm Biol. 2020, 58 (1), 1201-1207.

Tocchetti, C. G.; Caceres, V.; Stanley, B. A.; Xie, C.; Shi, S.; Watson, W. H.; O'Rourke, B.; Spadari-Bratfisch, R. C.; Cortassa, S.; Akar, F. G.; Paolocci, N.; Aon, M. A., GSH or Palmitate Preserves Mitochondrial Energetic/Redox Balance, Preventing Mechanical Dysfunction in Metabolically Challenged Myocytes/Hearts From Type 2 Diabetic Mice. Diabetes 2012, 61 (12), 3094-3105.

Tominaga, H., M. Ishiyama, F. Ohseto, K. Sasamoto, T. Hamamoto, K. Suzuki and M. Watanabe, Anal. Commun., 1999, 36, 47-50.

Torres-Gonzalez, M.; Gawlowski, T.; Kocalis, H.; Scott, B. T.; Dillmann, W. H., Mitochondrial 8-oxoguanine glycosylase decreases mitochondrial fragmentation and improves mitochondrial function in H9C2 cells under oxidative stress conditions. Am J Physiol Cell Physiol. 2014, 306 (3), C221-C229.

Untereiner, A. A.; Fu, M.; Módis, K.; Wang, R.; Ju, Y.; Wu, L., Stimulatory effect of CSE-generated H2S on hepatic mitochondrial biogenesis and the underlying mechanisms. Nitric Oxide 2016, 58, 67-76.

Untereiner, A. A.; Wang, R.; Ju, Y.; Wu, L., Decreased Gluconeogenesis in the Absence of Cystathionine Gamma-Lyase and the Underlying Mechanisms. Antioxid. Redox Signal. 2015, 24 (3), 129-140.

Ventura-Clapier, R.; Garnier, A.; Veksler, V., Transcriptional control of mitochondrial biogenesis: the central role of PGC-1α. Cardiovasc. Res. 2008, 79 (2), 208-217.

Vidhya Sivakumaran, B. A. S., Carlo G. Tocchetti, Jeff D. Ballin, Viviane Caceres, Lufang Zhou, Gizem Keceli, Peter P. Rainer, Dong I. Lee, Sabine Huke, Mark T. Ziolo, Evangelia G. Kranias, John P. Toscano, Gerald M. Wilson, Brian O'Rourke, David A. Kass, James E. Mahaney, and Nazareno Paolocci, HNO Enhances SERCA2a Activity and Cardiomyocyte Function by Promoting Redox-Dependent Phospholamban Oligomerization. Antioxid Redox Signal. 2013, 19 (11), 1185-1197.

Vile, G. F.; Winterbourn, C. C., dl-N,N'-dicarboxamidomethyl-N,N'-dicarboxymethyl-1,2-diaminopropane (ICRF- 198) and d-1,2-bis(3,5-dioxopiperazine-1-yl) propane (ICRF-187) inhibition of Fe3+ reduction, lipid peroxidation, and CaATPase inactivation in heart microsomes exposed to adriamycin. Cancer Res. 1990, 50 (8), 2307-2310.

Vincent, D. T.; Ibrahim, Y. F.; Espey, M. G.; Suzuki, Y. J., The role of antioxidants in the era of cardio-oncology. Cancer Chemother. Pharmacol. 2013, 72 (6), 1157-1168.

Wakabayashi, N., Dinkova-Kostova, A. T., Holtzclaw, W. D., Kang, M.-I., Kobayashi, A., Yamamoto, M., Kensler, T. W., and Talalay, P. (2004) Protection against electrophile and oxidant stress by induction of the phase 2 response: Fate of cysteines of the Keap1 sensor modified by inducers. Proc. Natl. Acad. Sci. 101, 2040-2045.

Wallace, K. B.; Sardão, V. A.; Oliveira, P. J., Mitochondrial Determinants of Doxorubicin-Induced Cardiomyopathy. Circ. Res. 2020, 126 (7), 926-941.

Wang, H.; Fang, B.; Peng, B.; Wang, L.; Xue, Y.; Bai, H.; Lu, S.; Voelcker, N. H.; Li, L.; Fu, L.; Huang, W., Recent Advances in Chemical Biology of Mitochondria Targeting. Front. Chem. 2021, 9.

Wang, Y., K. M. Dillon, Z. Li, E. W. Winckler and J. B. Matson, Angew. Chem. Int. Ed., 2020, 59, 16698-16704.

Westley, J., Rhodanese. In Adv. Enzymol., 1973; pp 327-368.

Wu, B. B.; Leung, K. T.; Poon, E. N., Mitochondrial-Targeted Therapy for Doxorubicin-Induced Cardiotoxicity. Int J Mol Sci. 2022, 23 (3).

Xiao, W.; Loscalzo, J., Metabolic Responses to Reductive Stress. Antioxid. Redox Signal. 2019, 32 (18), 1330-1347.

Yadav, P. K., M. Martinov, V. Vitvitsky, J. Seravalli, R. Wedmann, M. R. Filipovic and R. Banerjee, J. Am. Chem. Soc., 2016, 138, 289-299.

Yang, C.-t. N. O. Devarie-Baez, A. Hamsath, X.-d. Fu and M. Xian, Antioxid. Redox Signal., 2019, 33, 1092-1114.

Yang, Y.; Zhang, H.; Li, X.; Yang, T.; Jiang, Q., Effects of PPARα/PGC-1α on the energy metabolism remodeling and apoptosis in the doxorubicin induced mice cardiomyocytes in vitro. Int J Clin Exp Pathol. 2015, 8 (10), 12216-12224.

Yeh, E. T. H.; Bickford, C. L., Cardiovascular Complications of Cancer Therapy: Incidence, Pathogenesis, Diagnosis, and Management. J Am Coll Cardiol 2009, 53 (24), 2231-2247.

Youness, R. A.; Gad, A. Z.; Sanber, K.; Ahn, Y. J.; Lee, G.-J.; Khallaf, E.; Hafez, H. M.; Motaal, A. A.; Ahmed, N.; Gad, M. Z., Targeting hydrogen sulphide signaling in breast cancer. J. Adv. Res. 2021, 27, 177-190.

Yuan, Z., Y. Zheng, B. Yu, S. Wang, X. Yang and B. Wang, Org. Lett., 2018, 20, 6364-6367.

Zarenkiewicz, J., V. S. Khodade and J. P. Toscano, J. Org. Chem., 2021, 86, 868-877.

Zhang, L.; Tew, K. D., Chapter Ten-Reductive stress in cancer. In Advances in Cancer Research, Tew, K. D.; Fisher, P. B., Eds. Academic Press: 2021; Vol. 152, pp 383-413.

Zhang, L.; Wang, Y.; Li, Y.; Li, L.; Xu, S.; Feng, X.; Liu, S., Hydrogen Sulfide (H2S)-Releasing Compounds: Therapeutic Potential in Cardiovascular Diseases. Front. Pharmacol. 2018, 9 (1066).

Zhang, S.; Liu, X.; Bawa-Khalfe, T.; Lu, L.-S.; Lyu, Y. L.; Liu, L. F.; Yeh, E. T. H., Identification of the molecular basis of doxorubicin-induced cardiotoxicity. Nat. Med. 2012, 18 (11), 1639-1642.

Zhao, X.; Zhang, J.; Tong, N.; Chen, Y.; Luo, Y., Protective Effects of Berberine on Doxorubicin-Induced Hepatotoxicity in Mice. Biol Pharm Bull 2012, 35 (5), 796-800.

Zhao, Y., Matthew M. Cerda and M. D. Pluth, Chem. Sci., 2019, 10, 1873-1878.

Zheng, Y.; Yu, B.; Ji, K.; Pan, Z.; Chittavong, V.; Wang, B., Esterase-Sensitive Prodrugs with Tunable Release Rates and Direct Generation of Hydrogen Sulfide. Angew. Chem. Int. Ed. Engl. 2016, 55 (14), 4514-4518.

Zheng, Y.; Yu, B.; Li, Z.; Yuan, Z.; Organ, C. L.; Trivedi, R. K.; Wang, S.; Lefer, D. J.; Wang, B., An Esterase-Sensitive Prodrug Approach for Controllable Delivery of Persulfide Species. Angew. Chem., Int. Ed. 2017, 56 (39), 11749-11753.

Zhu, C.; Xuan, X.; Che, R.; Ding, G.; Zhao, M.; Bai, M.; Jia, Z.; Huang, S.; Zhang, A., Dysfunction of the PGC-1a-mitochondria axis confers adriamycin-induced podocyte injury. Am. J. Physiol. Renal Physiol. 2014, 306 (12), F1410-F1417.

Zhu, W.; Shou, W.; Payne, R. M.; Caldwell, R.; Field, L. J., A mouse model for juvenile doxorubicin-induced cardiac dysfunction. Pediatr Res. 2008, 64 (5), 488-494.

Zielonka, J.; Joseph, J.; Sikora, A.; Hardy, M.; Ouari, O.; Vasquez-Vivar, J.; Cheng, G.; Lopez, M.; Kalyanaraman, B., Mitochondria-Targeted Triphenylphosphonium-Based Compounds: Syntheses, Mechanisms of Action, and Therapeutic and Diagnostic Applications. Chem. Rev. 2017, 117 (15), 10043-10120.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

(I)

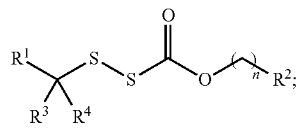

wherein:

n is 0 or 1;

$R^1$ is

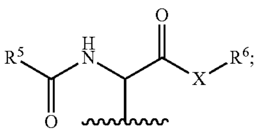

wherein $R^5$ and $R^6$ are each independently $C_1$-$C_4$ substituted or unsubstituted alkyl and substituted or unsubstituted aryl; X is O or NH $R^2$ is substituted or unsubstituted aryl;

$R^3$ and $R^4$ are each independently H or $C_1$-$C_4$ substituted or unsubstituted alkyl; and pharmaceutically acceptable salts thereof.

2. The compound of claim 1, wherein the compound of formula (I) is:

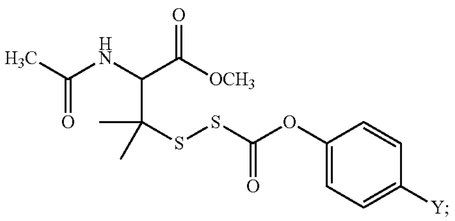

wherein Y is selected from the group consisting of H, $C_1$-$C_4$ alkyl, $C_1$-$C_4$ alkoxyl, NRR' where R and R' are each independently H or $C_1$-$C_4$ substituted or unsubstituted alkyl, —$CF_3$, halogen, and cyano.

3. The compound of claim 2, wherein the compound of formula (I) is selected from the group consisting of:

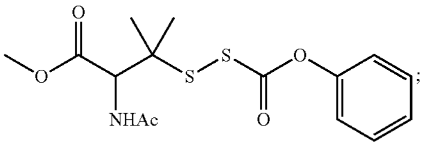
;

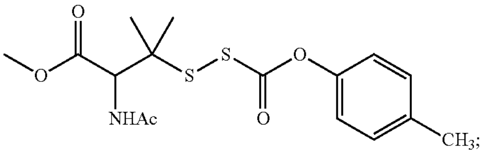

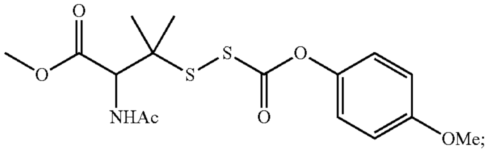

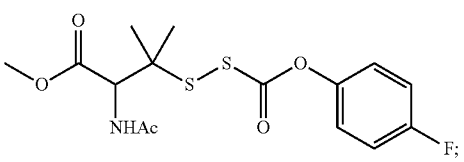

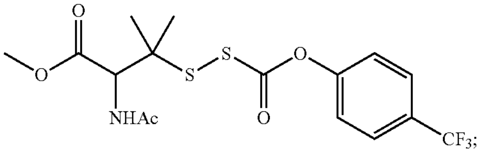
and

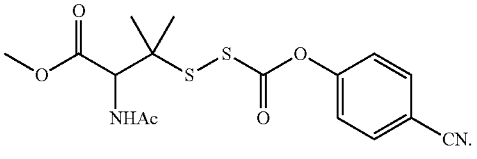

4. The compound of claim 1, wherein the compound of formula (I) is:

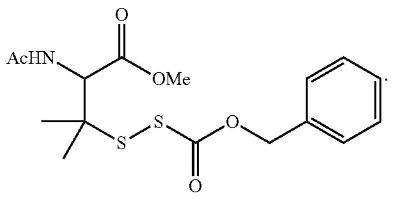 [SMILES: COC(=O)C(NC(C)=O)C(C)(C)SSC(=O)OCc1ccccc1]

5. A pharmaceutical composition comprising a compound of claim 1 and a pharmaceutically acceptable carrier.

6. A kit comprising a compound of claim 1 and instructions for use.

7. A method for treating a disorder, disease, or condition associated with oxidative stress in a subject in need of treatment thereof, the method comprising administering to the subject a therapeutically effective amount of a compound of formula (I) of claim 1.

8. The method of claim 7, wherein the disorder, disease, or condition associated with oxidative stress comprises ischemia/reperfusion injury.

9. The method of claim 8, wherein the treating comprises preventing, reducing the occurrence of or severity of, or protecting against ischemia/reperfusion injury.

10. The method of claim 8, wherein the subject is at risk of an ischemia/reperfusion injury or an ischemic event.

11. The method of claim 10, wherein the risk of an ischemia/reperfusion injury or an ischemic event includes a therapeutic intervention.

12. The method of claim 11, comprising administering a compound of formula (I) to the subject before the therapeutic intervention.

13. The method of claim 8, wherein the compound of formula (I) is administered to the subject after ischemia.

14. The method of claim 13, wherein the compound of formula (I) is administered to the subject after ischemia, but before reperfusion.

15. The method of claim 8, wherein the ischemia/reperfusion injury comprises myocardial ischemia/reperfusion injury.

16. A method for preventing or reducing ischemia/reperfusion injury to an organ to be transplanted, the method comprising administering to or contacting the organ with a therapeutically effective amount of a compound of formula (I) of claim 1.

17. The method of claim 16, comprising administering a compound of formula (I) to a transplant donor prior to harvesting the organ therefrom.

18. A method for treating a disorder, disease, or condition associated with impaired Fe-S cluster biosynthesis, the method comprising administering to a subject in need of treatment thereof, a therapeutically effective amount of a compound of formula (I) of claim 1.

19. The method of claim 18, wherein the disorder, disease, or condition associated with impaired Fe-S cluster biosynthesis is selected from Friedreich's Ataxia, sideroblastic anemia, and myopathy.

20. The method of claim 19, wherein the disorder, disease, or condition associated with impaired Fe-S cluster biosynthesis is Friedreich's Ataxia.

21. A method for treating anthracycline-induced cardiotoxicity in a subject in need of treatment thereof, the method comprising administering to the subject a therapeutically effective amount of a compound of formula (I) of claim 1.

22. The method of claim 21, wherein the subject is being treated with, has been treated with, or is expected to being treating with one or more anthracyclines.

23. The method of claim 21, wherein the subject is administered a compound of formula (I) before beginning treatment with an anthracycline, during treatment with an anthracycline, or after treatment with an anthracycline.

24. The method of claim 22, wherein the one or more anthracyclines are selected from daunorubicin, doxorubicin, epirubicin, idarubicin, mitoxantrone, valrubicin, and combinations thereof.

25. The method of claim 21, wherein the subject is being treated for cancer.

26. The method of claim 25, wherein the cancer is selected from acute lymphocytic leukemia, acute myelogenous leukemia, Hodgkin's lymphoma, non-Hodgkin's lymphoma, bladder cancer, breast cancer, metastatic breast cancer, ovarian cancer, osteogenic sarcoma, Ewing sarcoma, soft tissue sarcoma, thyroid cancer, neuroblastoma, Wilms' tumor, small cell lung cancer, advanced endometrial carcinoma, metastatic hepatocellular cancer, multiple myeloma, advanced renal cell carcinoma, thymomas and thymic malignancies, uterine sarcoma, and Waldenstrom macroglobulinemia.

27. The method of claim 21, wherein the subject is afflicted with or at risk of developing cardiomyopathy and/or heart failure.

28. A method for treating COVID-19, the method comprising administering to a subject in need of treatment thereof a therapeutically effective amount of a compound of formula (I) of claim 1.

* * * * *